(12) United States Patent
Endo et al.

(10) Patent No.: US 6,339,165 B1
(45) Date of Patent: Jan. 15, 2002

(54) FATTY ACID ESTERS COMPOSITION OF A POLYGLYCERINE, AND A PROCESS FOR THE PREPARATION THEREOF

(75) Inventors: Toshio Endo, Ohtake; Terumasa Daito, Sakai, both of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/722,527

(22) Filed: Nov. 28, 2000

Related U.S. Application Data

(62) Division of application No. 08/618,504, filed on Mar. 19, 1996.

(30) Foreign Application Priority Data

| Aug. 11, 1995 | (JP) | 7-227073 |
| Aug. 21, 1995 | (JP) | 7-233180 |
| Dec. 6, 1995 | (JP) | 7-344844 |
| Jan. 18, 1996 | (JP) | 8-6743 |
| Jan. 22, 1996 | (JP) | 8-8372 |
| Jan. 22, 1996 | (JP) | 8-8373 |
| Jan. 25, 1996 | (JP) | 8-10831 |
| Jan. 25, 1996 | (JP) | 8-10832 |
| Feb. 1, 1996 | (JP) | 8-16343 |
| Feb. 1, 1996 | (JP) | 8-16344 |
| Feb. 1, 1996 | (JP) | 8-16345 |
| Feb. 5, 1996 | (JP) | 8-18579 |
| Feb. 5, 1996 | (JP) | 8-18580 |
| Feb. 5, 1996 | (JP) | 8-18581 |
| Feb. 8, 1996 | (JP) | 8-22642 |
| Feb. 8, 1996 | (JP) | 8-22643 |
| Feb. 8, 1996 | (JP) | 8-22644 |
| Feb. 8, 1996 | (JP) | 8-22645 |

(51) Int. Cl.$^7$ .................................. D07C 55/00
(52) U.S. Cl. ................ 554/227; 516/27; 516/28; 516/29
(58) Field of Search .................. 516/27, 28, 29; 554/227

Primary Examiner—Deborah D. Carr
(74) Attorney, Agent, or Firm—Morgan & Finnegan, L.L.P.

(57) ABSTRACT

Disclosed are a fatty acid esters composition of a polyglycerine containing more than 70% of a fatty acid monoester which is defined by a specified analysis method, a process for the preparation thereof, a process for the preparation of a highly-purified fatty acid esters composition of a polyglycerine, and a highly-purified fatty acid esters composition of a polyglycerine having an oxirane oxygen concentration of below 100 ppm which is defined by a specified analysis method.

The fatty acid esters compositions of a polyglycerine are useful as additives for a variety of food-stuffs, additives for a variety of thermoplastic resins, and as additives for a variety of cosmetics or detergents.

12 Claims, 27 Drawing Sheets

| | | | | | | |
|---|---|---|---|---|---|---|
| System Serial# | :226 | | | System Program# | :1 | |
| Chromatogram Memory # | :226 | | | DP Program # | :0 (%Calc Area) | |
| Data Acquisition CH | :CH1 (Mode: CH1&CH2) | | | Time Range | : 0.00-144.39 min (0.010 min) | |

Analysis Name :
Sample Name :ML-10
Sample Attribution :UNK
Sample No. :1
Sample Volume :10
Sample Comment :
No. of Inject :1/1
Data Acquisition Date :Sat Mar 2 09:35:33 1996
DP. Index :
Amount of sample : ---
Amount of Int.Std :(1) --- (2) --- (3) ---
Scale Factor :(DP. Prog.) 1.000000e+00 (Samp. Tab) ---

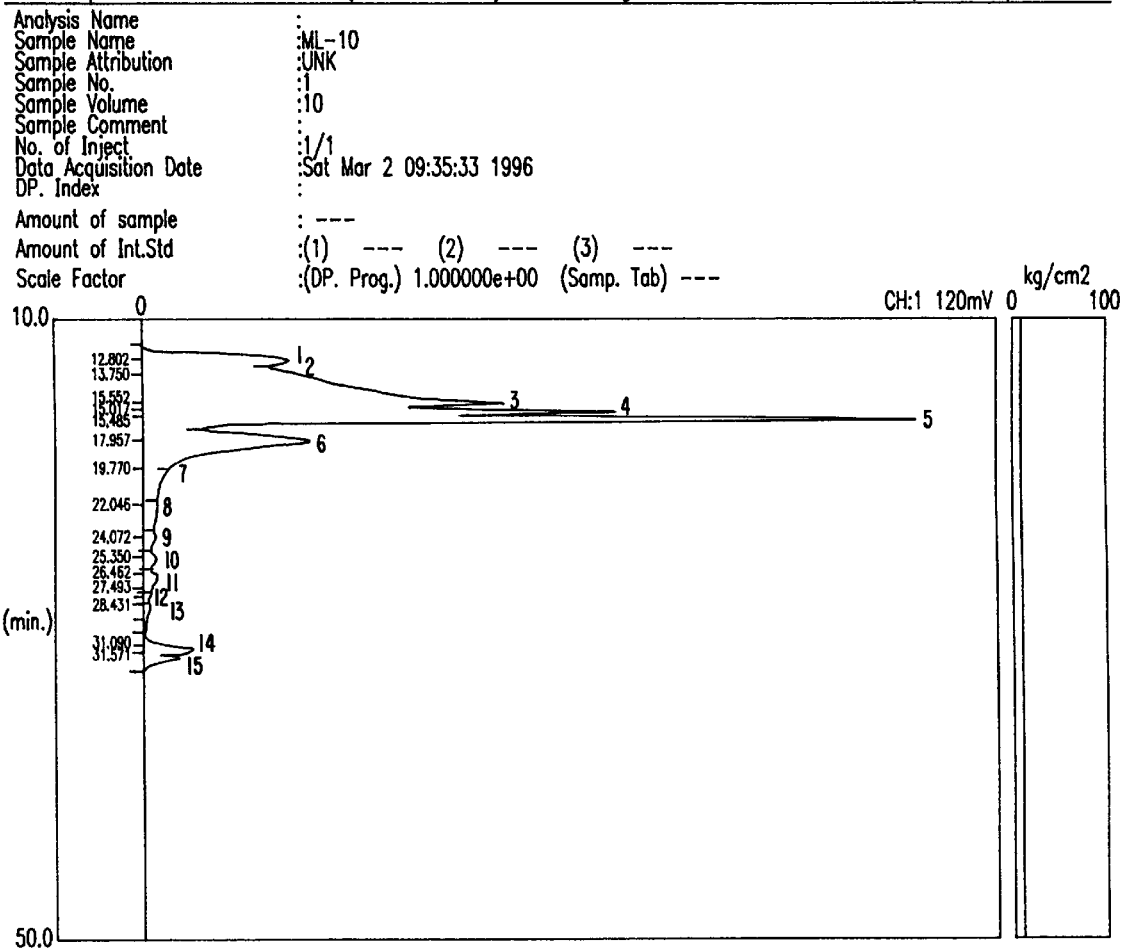

Calculation Results(Peaks not identified) / Peak : 15

| ID# | Name | Time (min) | Samp. Attr. | Grp. ID# | Area (uV*sec) | Height (uV) | Area% |
|---|---|---|---|---|---|---|---|
| 1 | | 12.802V | - | - | 893966 | 21224 | 7.0496 |
| 2 | | 13.750S | - | - | 3457756 | 22186 | 27.2672 |
| 3 | | 15.552V | - | - | 1167167 | 51411 | 9.2040 |
| 4 | | 16.017V | - | - | 1474564 | 66787 | 11.6281 |
| 5 | | 16.485V | - | - | 2756958 | 109541 | 21.7408 |
| 6 | | 17.957V | - | - | 1787905 | 23585 | 14.0991 |
| 7 | | 19.770S | - | - | 297432 | 3357 | 2.3455 |
| 8 | | 22.046V | - | - | 166171 | 1801 | 1.3104 |
| 9 | | 24.072V | - | - | 92322 | 1440 | 0.7280 |
| 10 | | 25.350V | - | - | 73752 | 1607 | 0.5816 |
| 11 | | 26.462V | - | - | 91729 | 1680 | 0.7234 |
| 12 | | 27.493V | - | - | 17473 | 646 | 0.1378 |
| 13 | | 28.431V | - | - | 25372 | 714 | 0.2001 |
| 14 | | 31.090V | - | - | 240299 | 6747 | 1.8949 |
| 15 | | 31.571V | - | - | 138164 | 4766 | 1.0895 |
| | Total | | | | 12681030 | 317492 | 100.0000 |

FIG. 24

| | | | | | | |
|---|---|---|---|---|---|---|
| System Serial# | :227 | | System Program# | :1 | | |
| Chromatogram Memory # | :227 | | DP Program # | :0 (%Calc Area) | | |
| Data Acquisition CH | :CH1 (Mode: CH1&CH2) | | Time Range | : 0.00–185.01 min (0.010 min) | | |

Analysis Name :
Sample Name :ML-750
Sample Attribution :UNK
Sample No. :1
Sample Volume :10
Sample Comment :
No. of Inject :1/1
Data Acquisition Date :Sat Mar 2 12:02:57 1996
DP. Index :
Amount of sample : ---
Amount of Int.Std :(1) --- (2) --- (3) ---
Scale Factor :(DP. Prog.) 1.000000e+00 (Samp. Tab) ---

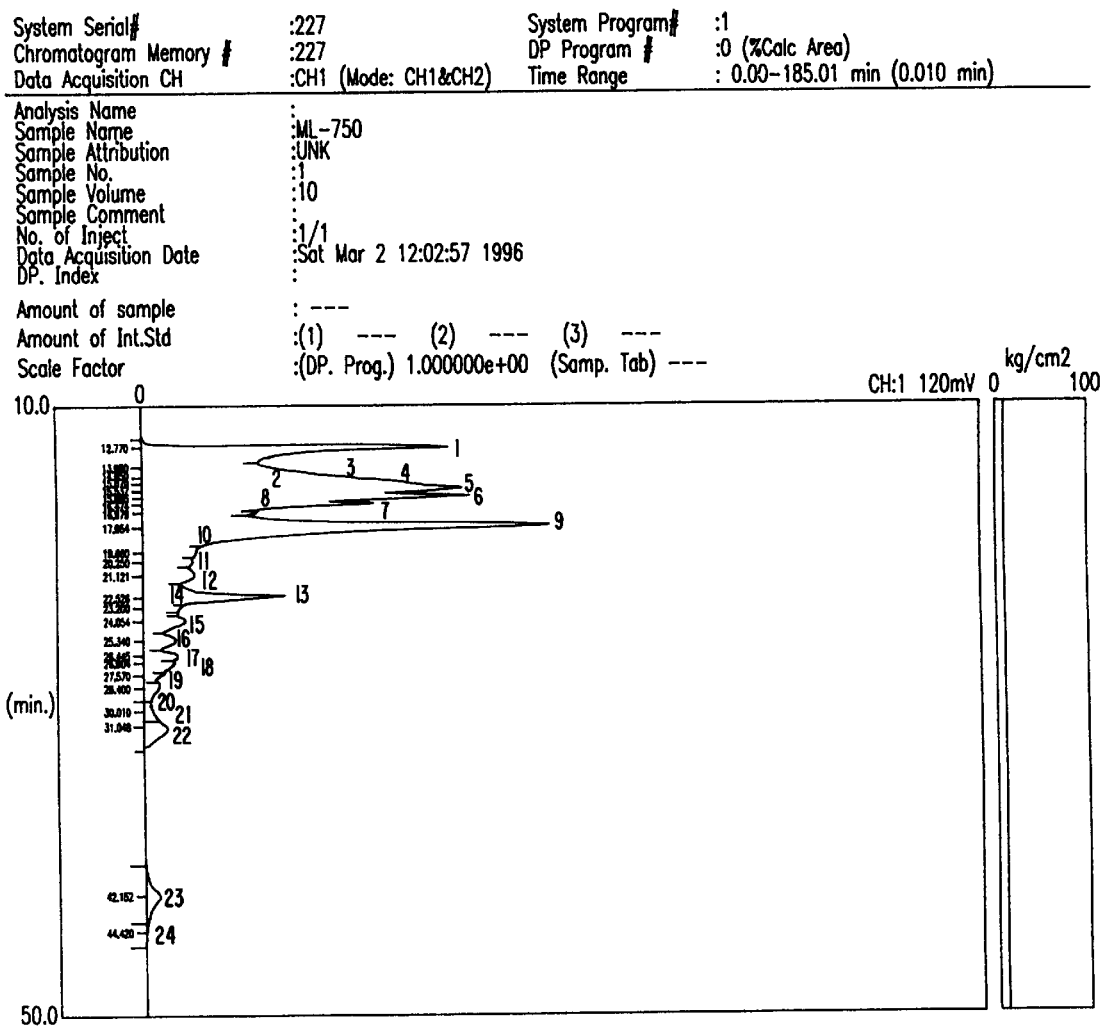

Calculation Results(Peaks not identified) / Peak : 24

| D# | Name | Time (min) | Samp. Attr. | Grp. ID# | Area (uV*sec) | Height (uV) | Area% |
|---|---|---|---|---|---|---|---|
| 1 | | 12.776V | – | – | 1861094 | 43951 | 12.5461 |
| 2 | | 13.990S | – | – | 961653 | 18694 | 6.4828 |
| 3 | | 14.650S | – | – | 771585 | 29159 | 5.2015 |
| 4 | | 15.070S | – | – | 667991 | 36665 | 4.5031 |
| 5 | | 15.537V | – | – | 1354534 | 46619 | 9.1313 |
| 6 | | 15.995V | – | – | 1207014 | 47550 | 8.1368 |
| 7 | | 16.474V | – | – | 900398 | 33645 | 6.0698 |
| 8 | | 16.979V | – | – | 387630 | 17053 | 2.6131 |
| 9 | | 17.954V | – | – | 3175720 | 58684 | 21.4084 |
| 10 | | 19.660S | – | – | 384969 | 7918 | 2.5952 |
| 11 | | 20.250S | – | – | 255817 | 7391 | 1.7245 |
| 12 | | 21.121V | – | – | 412036 | 7560 | 2.7776 |
| 13 | | 22.526V | – | – | 913582 | 21029 | 6.1587 |
| 14 | | 23.200S | – | – | 135553 | 5556 | 0.9138 |
| 15 | | 24.054V | – | – | 312403 | 5990 | 2.1060 |
| 16 | | 25.340V | – | – | 237815 | 4590 | 1.6032 |

FIG. 25

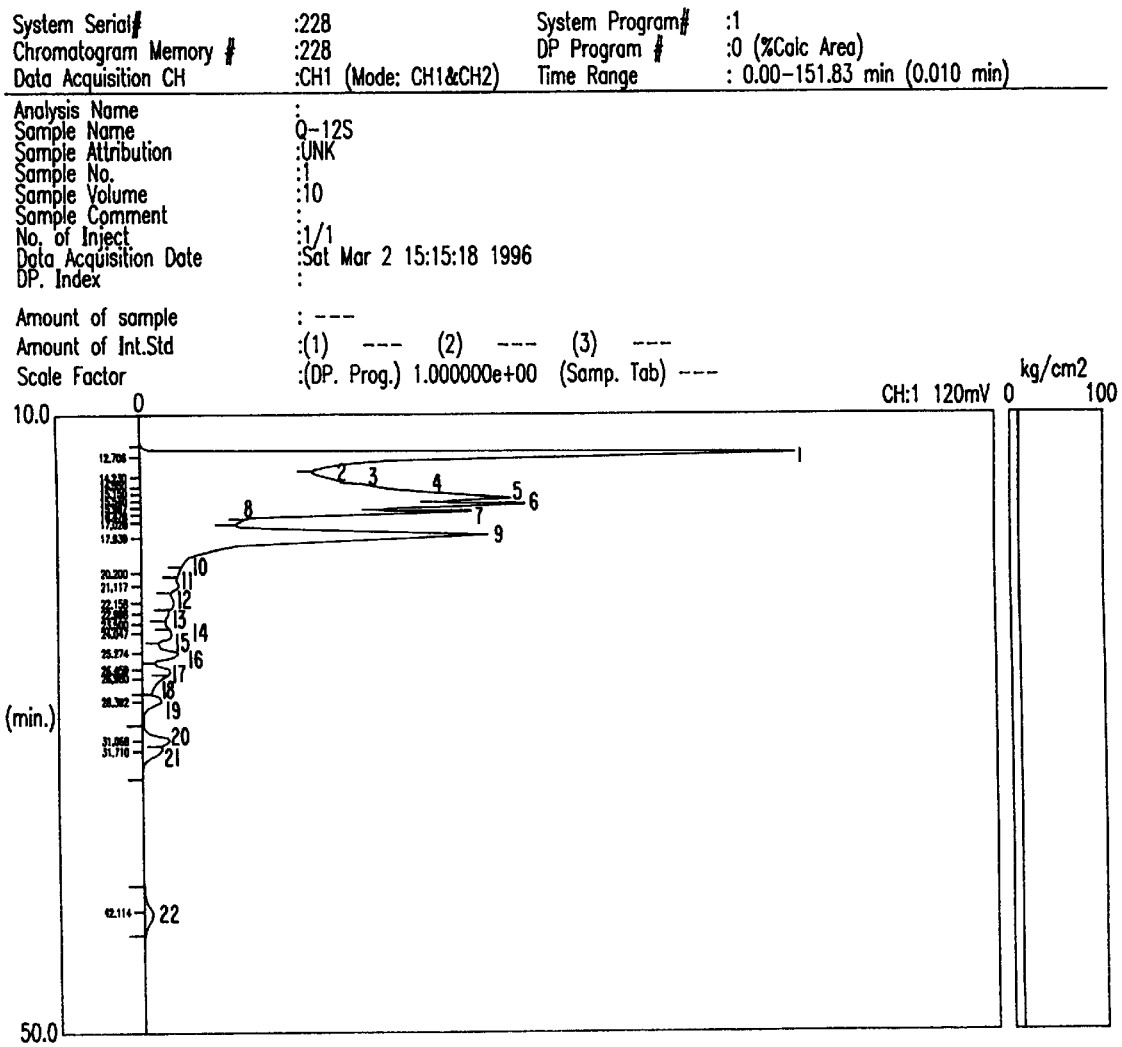

FIG. 26

| System Serial# | :228 | System Program# | :1 |
|---|---|---|---|
| Chromatogram Memory # | :228 | DP Program # | :0 (%Calc Area) |
| Data Acquisition CH | :CH1 (Mode: CH1&CH2) | Time Range | : 0.00-151.83 min (0.010 min) |

Analysis Name :
Sample Name : Q-12S
Sample Attribution : UNK
Sample No. : 1
Sample Volume : 10
Sample Comment :
No. of Inject : 1/1
Data Acquisition Date : Sat Mar 2 15:15:18 1996
DP. Index :

Amount of sample : ---
Amount of Int.Std :(1) --- (2) --- (3) ---
Scale Factor :(DP. Prog.) 1.000000e+00 (Samp. Tab) ---

CH:1 120mV 0 ——— 100 kg/cm2

Calculation Results(Peaks not identified) / Peak : 22

| D# | Name | Time (min) | Samp. Attr. | Grp. ID# | Area (uV*sec) | Height (uV) | Area% |
|---|---|---|---|---|---|---|---|
| 1 |  | 12.706V | – | – | 3641717 | 91447 | 23.7598 |
| 2 |  | 14.230S | – | – | 1084715 | 26987 | 7.0770 |
| 3 |  | 14.650S | – | – | 790158 | 31273 | 5.1553 |
| 4 |  | 15.150S | – | – | 678692 | 40738 | 4.4280 |
| 5 |  | 15.540V | – | – | 1562518 | 51703 | 10.1944 |
| 6 |  | 15.997V | – | – | 1293065 | 54198 | 8.4364 |
| 7 |  | 16.478V | – | – | 1201119 | 46400 | 7.8365 |
| 8 |  | 17.020S | – | – | 250851 | 13141 | 1.6366 |
| 9 |  | 17.939V | – | – | 2837634 | 48581 | 18.5137 |
| 10 |  | 20.200S | – | – | 163761 | 5254 | 1.0684 |
| 11 |  | 21.117V | – | – | 294660 | 5196 | 1.9225 |
| 12 |  | 22.158V | – | – | 263277 | 4437 | 1.7177 |
| 13 |  | 22.996V | – | – | 122904 | 3406 | 0.8019 |
| 14 |  | 23.600S | – | – | 101852 | 3098 | 0.6645 |
| 15 |  | 24.047V | – | – | 138841 | 4092 | 0.9058 |
| 16 |  | 25.274V | – | – | 229138 | 5046 | 1.4950 |

FATTY ACID ESTERS COMPOSITION OF A POLYGLYCERINE, AND A PROCESS FOR THE PREPARATION THEREOF

Divisional of application Ser. No. 08/618,504 filed Mar. 19, 1996.

FIELD OF THE INVENTION

The present invention relates to a fatty acid esters composition of a polyglycerine containing more than 70% of a fatty acid monoester and a process for the preparation thereof.

Furthermore, the present invention relates to a highly-purified fatty acid esters composition of a polyglycerine and a process for the preparation thereof.

Still further, the present invention relates to the use of the fatty acid esters compositions of a polyglycerine for an additive for food-stuffs.

In addition, the present invention relates to a resin composition containing the fatty acid esters compositions of a polyglycerine.

Besides, the present invention relates to compositions for cosmetics or detergents containing the fatty acid esters compositions of a polyglycerine.

In more detail, the present invention relates to a fatty acid esters composition of a polyglycerine having an excellent emulsifying ability. The fatty acid esters compositions of a polyglycerine are useful as an additive for food-stuffs, an additive for thermoplastic resins, and an additive for cosmetics or detergents, etc.

BACKGROUND OF THE INVENTION

In recent, fatty acid esters of a polyglycerine are permitted as an additive such as an emulsifier for food-stuffs, and demands in a market are getting increased. The fatty acid esters compositions of a polyglycerine have been usually employed in a variety of fields, particularly such as foods, as an emulsifier or an agent for adjusting a viscosity because esters having a wide range of HLB values can be obtained by the combinations of polyglycerines having various molecular weight with fatty acids having various chain length which are starting materials, and it exhibits a higher stability in an acidic range.

As processes for preparing the fatty acid esters composition of a polyglycerine, there are exemplified; (1) an esterification reaction of a polyglycerine with a fatty acid, (2) a transesterifications reaction of a polyglycerine with a fatty acid ester, (3) a transesterification reaction of a polyglycerine with an oil and fatty acid, (4) an addition polymerization reaction of glycidol to a monoglyceride of a fatty acid, and (5) an addition polymerization reaction of glycidol to a fatty acid, etc. Of the above-described reactions, the processes (2) and (3) are problematic in the reactivity and the processes have many limitations in quality and purity of the fatty acid ester of a polyglycerine.

The process (1) is described in JAOCS (Journal of American Oil Chemists' Society), Vol. 58, page 878 (1981), in which there is carried out the esterification reaction of a polyglycerine with a fatty acid in the presence of alkali catalysts to obtain a fatty acid ester of the polyglycerine.

Furthermore, Japanese Patent Unexamined Publications (Kokai) No. 41007/1994 discloses similar processes.

The process (5) is described in Japanese Patent Unexamined Publications (Kokai) No. 65705/1976, in which there is prepared a fatty acid monoester of glycerine. However, the Publication states that there is obtained a carboxylic acid-1-monoglyceride having the polymerization degree of glycerine of 1 with a high percentage in the presence of an inert solvent, that is, it corresponds to a compound having n of average 1 in the above-described chemical formula [1]. Notwithstanding, there is not mentioned a fatty acid esters composition of a polyglycerine at all in the Publication.

As processes in which the addition polymerization reaction of glycidol is employed, there are exemplified the addition polymerization reaction [Japanese Patent Examined Publication (Kokoku) No. 55254/1989, Japanese Patent Examined Publication (Kokoku) No. 11532/1992, Japanese Patent Examined Publication (Kokoku) No. 1291/1993] of glycidol to glycerine to obtain a polyglycerine employed in the processes (1) to (3), the preparation of a polyglycerine [Japanese Patent Examined Publication (Kokoku) No. 69621/1992] by a hydrolysis reaction after the addition polymerization reaction of glycidol to a fatty acid, and the preparation of polyglycerine monoalkylether or the preparation of polyglycerine monoalkylthioether [U.S. Pat. Nos. 3,821,372, 3,966,398, and 4,087,466], etc.

However, in the preparation process of a polyglycerine by a hydrolysis reaction after the addition polymerization reaction of glycidol to a fatty acid described in Japanese Patent Examined Publication (Kokoku) No. 69621/1992, low fatty acids (a carbon number of 2 to 6) are employed as fatty acids to prepare polyglycerines, and a fatty acid ester of a polyglycerine is not mentioned at all.

Heretofore, a fatty acid monoester of a polyglycerine has been prepared by the above-described process (1). In the process, it is pointed out that a polyglycerine having reactive hydroxyl groups of 4 to 10 on an average is employed as a starting polyglycerine, as a result, a resulting product contains an unreacted polyglycerine, poly-substituted fatty acid esters such as diester, triester, and tetraester, etc. other than the desired fatty acid monoester of a polyglycerine [N. Garti, et al, Journal of American Oil Chemists' Society, 58, 317–319 (1982)].

Furthermore, even in the process (4) in which glycidol is addition polymerized to a fatty acid monoglyceride, a purity of a reaction product remarkably depends upon the starting fatty acid monoglyceride [c.f. U.S. Pat. No. 4,515,775]. Particularly, in the case when there is employed a fatty acid monoglyceride obtained by the reaction of glycerine with a fatty acid as a starting material, the starting material contains unreacted glycerine as well as in the above-described process (1), resulting in that a fatty acid monoester of a polyglycerine obtained by the addition polymerization of glycidol contains only approximately 40% of the fatty acid monoester, and the residue of approximately 60% is composed of unreacted glycerine and poly-substituted fatty acid esters [Shigeru Tsuda, Monoglyceride, page 67(1985), Maki Book Store].

As described above, there remain a large amount of unreacted polyglycerine and poly-substituted fatty acid esters in the fatty acid monoester of a polyglycerine employed until now. In the case when such the fatty acid monoester is employed as surfactants or emulsion stabilizers in food industries, it results in decrease of surface tension, decrease of dispersibility, decrease of foaming ability, and decrease of stability in emulsifying.

As a process for removing the unreacted polyglycerine, Japanese Patent Unexamined Publication (Kokai) No. 23837/1988 discloses a process in which the unreacted polyglycerine is removed by a liquid separation process using a mixed solvent composed of at least one of water-soluble organic solvents or water and at least one of water-insoluble organic solvents.

Furthermore, Japanese Patent Unexamined Publication (Kokai) No. 81252/1991 discloses a process that the unreacted polyglycerine is removed by an adsorption method in which a solution of a reaction product in esterification is brought into contact with an alkyl-silylated silicagel.

Still further, Japanese Patent Unexamined Publication (Kokai) No. 41007/1994 discloses an extracting process in which the unreacted polyglycerine is removed by employing a water-soluble organic solvent such as n-butyl alcohol, n-propanol, or dioxane, etc. together with water or an aqueous solution containing a salting agent such as lithium, sodium, potassium or ammonium salts of an organic acid or an inorganic acid such as sulfuric acid or phosphoric acid.

And also, Japanese Patent Unexamined Publication (Kokai) No. 228052/1994 discloses an extracting process in which the unreacted polyglycerine is removed by employing methylethylketone together with water.

However, the process is Japanese Patent Unexamined Publication (Kokai) No. 23837/1988 includes a problem in uses for food-stuff from a viewpoint of safety because of aromatic hydrocarbons such as benzene and toluene which are described as examples of the water-insoluble organic solvents. Furthermore, in the process, the reacting molar ratio of a fatty acid to a polyglycerine is limited within 1, and there is not described the effectiveness in the reaction molar ratio exceeding 1.

Still further, in the case of a toluene/methanol system, it is observed that a large amount of a fatty acid ester of polyglycerine having a high HLB value moves to methanol phase containing water even in the reaction ratio below 1 and, further, unreacted polyglycerine cannot be sufficiently removed, resulting in that there are problems in industrial preparation.

In addition, the separation process disclosed in the Kokai No. 81252/1991 includes disadvantages that operations costs are expensive and operations are troublesome.

Besides, even though according to the prior arts including the processes disclosed in the Kokai No. 41007/1994 and 228052/1994, although the unreacted polyglycerine can be removed, poly-substituted esters of polyglycerine cannot be removed.

As described hereinabove, in the case when there is prepared a fatty acid esters composition of a polyglycerine according to the above-described processes (4) and (5) in which glycidol is employed, preparation of polyglycerine can be prevented. However, there is a problem that a small amount of unreacted glycidol remains in the fatty acid esters composition of a polyglycerine.

Even a small amount, unreacted residual glycidol itself does not exhibit emulsifying ability, and unpreferably causes a remarkable decrease of surface tension, dispersibility, foaming ability, and stability in emulsifying in products including the fatty acid esters composition of a polyglycerine.

In order to remove a small amount of unreacted glycidol from the composition, there requires molecular distillation which is not economical and not preferred from a viewpoint of industrial applications. It is to be noted that glycidol is another name of an epoxy alcohol.

In view of the above-described background, there has been expected a fatty acid esters composition of a polyglycerine containing high contents of a fatty acid monoester which exhibits an improved surface tension, dispersibility, foaming ability, and stability in emulsifying during uses as an emulsifying stabilizer in the fields of surface active agents, food-stuffs, cosmetics, and detergents.

Furthermore, the fatty acid esters composition of a polyglycerine containing high contents of a fatty acid monoester in the present invention effectively acts as a plasticizer, an improver of a wetting ability for hydrophobic resins, an improver of a printing property, an anti-static agent, a releasing agent, or an anti-clouding agent, etc. for a variety of resins which include a polyvinyl chloride resin, a styrene-based resin, a methylmethacrylate-based resin, and a polyacetal resin.

For example, a polyvinyl chloride resin has been widely employed as a wrapping film or a bottle for food-stuffs, cosmetics, detergents, and other miscellaneous goods, materials for printing such as a calendar and a poster because of its excellent rigidity, transparency, moldability, printing ability.

In particular, uniaxially or biaxially oriented films are employed as a shrinkable wrapping and a shrinkable label because of the excellence in rigidity, a gloss, dimensional stability in storage, and a shrinkable property.

However, similarly to other resins, a polyvinyl chloride resin has a disadvantage that static electricity is very readily charged, resulting in that it gives an unpleasant feeling to human bodies and it readily catches dusts in air.

Accordingly, there is often carried out a process for preventing static electricity.

The process for preventing static electricity includes mixing an anti-static agent together with a thermal stabilizer, a reinforcing material, and a slipping agent, etc. in the case of molding a polyvinyl chloride resin, or coating an anti-static agent after molding.

As the anti-static agent for vinyl chloride resins, there have been conventionally employed a fatty acid ester of glycerine, a fatty acid ester or sorbitan, a non-ionic surface active agent of a higher alcohol, and an anionic surface active agent such as a sodium alkylbenzene sulfonate and a sodium alkylsulfonate. However, mixing of the anti-static agents cannot sufficiently give an effect for preventing static electricity to films having thin thickness such as thermally shrinkable oriented films, and transparency of the films is occasionally decreased.

On the other hand, coating of the anti-static agents after molding has disadvantages that an effect for preventing static electricity is often decreased by rubbing or evaporation with a long lapse of time, and further films themselves readily cause blocking.

In JP Kokai No. 1861/1994, although there is disclosed the use of a fatty acid esters composition of a polyglycerine for an anti-static agent, the composition contains a large amount of a residual polyglycerine and poly-substituted esters, unpreferably resulting in that an effect for emulsifying and preventing static electricity is remarkably small, whereby, a large amount of the composition has to be employed.

Meanwhile, a styrene-based resin is excellent in transparency, non-toxic, non-deodorant, and water-resistant.

However, there has been a problem that it is brittle in spite of exhibiting strength and rigidity. Recently, the brittleness in a styrene-based resin has been improved, whereby, the styrene-based resin has been used as films for food-stuffs.

Particularly, the styrene-based resin films have a variety of problems in the use as films for wrapping food-stuffs because of non-affinity for water.

In the case when the styrene-based resin films are used for wrapping food-stuffs and stored at low temperatures, moisture in the food-stuffs such as vegetables or meat forms drops of water over the films. There is a problem that the drops of water adversely affect transparency of the films, unpreferably resulting in that the food-stuffs in wrapping cannot be visually identified, and it is not only visually unpreferred, but also it gives a bad feeling.

In order to solve the problem, there has been thought out a process for improving surface properties of the films.

As the process for improving surface properties of the films, there are known processes that an anti-clouding agent is coated on the films or mixed in preparing the films.

Although the coating process of the anti-clouding agent provides an excellent anti-clouding effect for a short period after coating, anti-clouding effect becomes decreased by rubbing with a long time of lapse.

On the other hand, the mixing process of the anti-clouding agent can provide the films with an excellent anti-clouding effect for a long period after mixing.

As the anti-clouding agent for the styrene-based resin films, there are known (1) fatty acid esters of glycerine (JP Kokoku No. 4147/1963 and JP Kokoku No. 26532/1997), (2) fatty acid esters of polyethyleneglycol (disclosed in JP Kokoku No. 21112/1964), and (3) fatty acid monoesters of polyglycerine (JP Kokai No. 157558/1986), etc.

However, in the case when the fatty acid esters of glycerine of (1) and the fatty acid esters of polyethyleneglycol of (2) are employed as the anti-clouding agent for the styrene-based resin films, a large amount of those must be employed in order to provide an aimed anti-clouding effect, resulting in that mixing is difficult.

In the case when the fatty acid monoesters of polyglycerine of (3) is employed as the anti-clouding agent for the styrene-based resin films, although an anti-clouding effect at ordinary temperatures is excellent, an anti-clouding effect at low temperatures is poor, and further miscibility and transparency are poor, resulting in being not appropriate to wrapping for food-stuffs at low temperatures.

It is to be noted that the fatty acid monoesters of polyglycerine of the above-described (3) are prepared by the esterification of polyglycerine with a fatty acid and the purification by molecular distillation or solvent extraction, which is different from a fatty acid esters composition of polyglycerine in the present invention prepared by the addition polymerization reaction of glycidol to a fatty acid.

Anti-clouding agent for the styrene-based resin films to be employed for wrapping food-stuffs has to be excellent in a low temperature property, a high temperature property, a recovery property, and durability, etc. Particularly, it attaches importance to an anti-clouding effect at a low temperature atmosphere for a long time of period.

In order to make durability of an anti-clouding effect at low temperatures exhibit, an anti-clouding agent to be mixed must exhibit moderate miscibility with the styrene-based resins at low temperatures.

An anti-clouding agent exhibiting a poor miscibility readily moves to the surface of the film, and it oozes out of the film, unpreferably resulting in causing blocking of the films in spite of the presence of the anti-clouding effect.

On the other hand, an anti-clouding agent exhibiting an excessive miscibility does not readily move to the surface of the film, unpreferably resulting in not exhibiting the anti-clouding effect. Accordingly, an anti-clouding agent must exhibit a well-balanced miscibility with resins.

As a conventional anti-clouding agent for the styrene-based resins has an excessive miscibility with the resins, it is involved inside the resins, resulting in that there has been required a large amount ranging from 7 to 8% by weight.

The problems can be solved by the use of the fatty acid esters composition of a polyglycerine containing high contents of a fatty acid monoester in the present invention.

Furthermore, although an article molded from the styrene-based resin is particularly excellent in transparency, there is a problem that it readily accumulates static electricity induced by friction, and it does not readily disappear, unpreferably resulting in that dust in air is drawn.

In order to prevent the accumulation of static electricity, surface active agents have been mixed in the resin, or silicone-based compounds have been coated on the surface of the molded article.

However, there are problems that a small amount of the surface active agents do not sufficiently provide an anti-static effect and, unpreferably, a large amount of the surface active agents adversely affect transparency of the resin, and coating process of silicone-based compounds onto the surface of the molded article results in increasing costs of production.

The problems can be solved by the use of the fatty acid esters composition of a polyglycerine containing high contents of a fatty acid monoester in the present invention.

In the meantime, a methylmethacrylate-based resin is widely employed in a variety of fields which supply parts for automobiles such as a cover for a variety of meters, optical parts such as photo-magnetic disks and lenses, and a cover for an illuminating lamp, etc., because of its excellence in transparency, weatherability, and mechanical properties, etc.

The molded particles are usually prepared by an injection molding and a compression molding. Particularly, the optical parts such as photo-magnetic disks and lenses are molded by compression molding with a precise mold, and a molded article is exceedingly tightly in contact with the mold, whereby, release of the molded article from the mold becomes insufficient, resulting in making a productivity lower.

Therefore, it is proposed that a variety of releasing agents are employed in molding a methylmethacrylate-based resin.

For example, JP Kokai No. 73754/1086 discloses a methylmethacrylate resin in which there are mixed higher fatty acid esters, polyvalent alcohols, higher alcohols, higher fatty acids, amides of higher fatty acids, and metal salts of higher fatty acids as releasing agents.

However, a releasing property is insufficient, and the releasing agents move to the surface of molded articles, unpreferably resulting in that the surface of the mold becomes dirty, and commercial values remarkably decrease by coloration of the molded article.

The additive which is the fatty acid esters composition of a polyglycerine of the present invention can provide a methylmethacrylate-based resin having an excellent releasing property in spite of a small amount of use.

In the meantime, a polyacetal resin which is one of engineering plastics has been exceedingly widely employed in a variety of fields which supply parts for automobiles or home electric appliances, etc., because of its excellence in physical properties such as mechanical properties and electric properties, moldability, and chemical properties such as chemical resistance and thermal stability.

However, as a polyacetal resin unprocessed is poor in a printing property by a variety of inks, it has been used after a treatment by corona discharge.

However, in the case when it is molded, for example, as a shutter for a disk or a magnetic tape cartridge, as the shutter itself is thin in thickness, bending or deformation is unpreferably caused by a long time treatment or high-voltage treatment in corona discharge, resulting in incapability of practically using.

In view of the situations, there has been expected a material on which inks can be printed even by a short time treatment or low-voltage treatment in corona discharge.

Although a process of a primer coating is known as a process for improving a printing property, the primer process requires solvents, unpreferably resulting in being problematic from viewpoint of environmental pollution.

In JP Kokai No. 195155/1985, there is disclosed a process in which a polyacetal resin is mixed with 0.01–3 parts by weight of hindered amines together with 0.01–4 parts by weight of a specific benztriazole-based ultraviolet absorbent in order to improve weatherability.

However, a printing property cannot be sufficiently improved by the process, and further, durability of the printing property is almost not improved.

Furthermore, in JP Kokai No. 128740/1982, there is disclosed a process in which a polyacetal resin is mixed with 0.01–5 parts by weight of a fatty acid esters composition of a polyglycerine and/or polyalkyleneglycol-alkylether.

However, even a printing property cannot be sufficiently improved by the process because the fatty acid esters composition of a polyglycerine is not prepared by the above-described glycidol process (5).

Still further, in JP Kokai No. 14709/1994, there is disclosed a process in which a polyacetal resin is mixed with 0.01–3% by weight of a hindered amine compound together with an effective amount (as an anti-static agent) a fatty acid ester of a polyvalent alcohol.

However, even a printing property cannot be sufficiently improved by the process, and further, durability of the printing property is almost not improved.

In addition, in JP Kokai No. 41583/1986, there is disclosed a process in which a polyacetal resin having the thickness of less than 2000 microns in skin layer.

However, even a printing property cannot also be satisfactorily improved by the process, and further, durability of the printing property is not occasionally improved.

The problems in the polyacetal resin can be solved by the use of the fatty acid esters composition of a polyglycerine containing high contents of a fatty acid monoester in the present invention.

In addition, there is a problem that polyacetal resins or a article molded therefrom do not exhibit a sufficient wetting property to water and a liquid containing water such as water-soluble inks, and blood, etc.

Wide applications of the polyacetal resins demand a variety of special characteristics as materials. One of the special characteristics is an improved wetting property to inks, etc.

Wetting property is prescribed in JIS K6768 in which it is defined as a condition that liquid coated on the surface of a solid is not repelled.

As a method for measuring the wetting property, there is known a method measuring contact angle, and small contact angle represents easiness of wetting.

Wetting property is required in a variety of molded articles. For example, in an ink jet nozzle in a printer for a personal computer, wetting property of the nozzle edge surface is required in order to constantly control the direction jetting ink, resulting in improving quality of printing.

Furthermore, in a carrier for a biosensor, improved wetting property of a sample liquid is required in order to elevate a sensitivity of measurement.

As methods for improving wetting property, there have been put into practice plasma treatments, chemical treatments, and surface coating by paints. However, the methods include a disadvantage of inferior efficiency in production because a highly-controlled technology is required in order to guarantee a constant quality in surface treatment.

As methods for improving wetting property in a polyacetal resin, although JP-A-257499/1994 discloses a method in which there is mixed an additive such as polyethylene glycol for improving wetting property, the method is insufficient.

Although JP-A-293856/1994 discloses a method in which there is mixed a fatty acid esters composition of a polyglycerine for improving wetting property, a large amount of the composition must be employed in the method because a large amount of unreacted polyglycerine resins in the composition.

Furthermore, a polyalkyleneglycol or a fatty acid esters composition of a polyvalent alcohol is also insufficient from viewpoint of improving wetting property, as shown in Comparative Examples of the present invention which are described later.

Still further, a large amount of a compound improving wetting property occasionally tends to adversely affect to mechanical properties and moldability.

In addition, a polyacetal resin is used as a resin composition by mixing a hindered phenol-based compound, inorganic fibers having short length and other additives, in order to prepare small or precise parts having thin thickness for precision instruments such as a watch, a printer, and a desk top electronic calculator, etc., because of being excellent in mechanical properties and dimensional stability.

As the inorganic fibers having short length, there are exemplified fiberglass and fibrous potassium titanate.

However, the fiberglass has the average fiber diameter ranging from 6 to 13 microns and the average fiber length ranging from 20 to 3000 microns. Accordingly, diameter and length are too thick and too long, resulting in being incapable of employing, for example, as gears for watch having the thickness of 50 or 60 microns.

On the other hand, the fibrous potassium titanate has the average fiber diameter ranging from 0.2 to 2 microns and the average fiber length ranging from 10 to 100 microns.

Accordingly, although the fibrous potassium titanate can be employed as the gears, it often causes a problem of gate plugging in a molding die.

Recently, micro-fibrous titanium oxide has been employed as substitutes for fiberglass and fibrous potassium titanate.

For example, JP-A-113465/1989 teaches that micro fibrous titanium oxide is employed to prepare a resin composition with which there can be formed molded articles having excellent strength and gloss of the surface.

However, the polyacetal resin composition in which micro-fibrous titanium oxide is mixed has a drawback that releasing property from a molding die is poor.

The poorness results in a poor profile property of the surface in a molded article and a stain in a molding die.

Particularly, as the molding die for the precise parts is small, cleaning of the stain requires a long maintenance time, resulting in falling productivity.

The problems can be solved by the use of only a small amount of the fatty acid esters composition of a polyglycerine having high contents of a fatty acid monoester in the present invention.

In the meantime, a fatty acid esters composition of a polyglycerine has been widely used as an additives for cosmetics, toiletries, and detergents.

As a specific example of cosmetics, a water-in-oil type-emulsified composition for cosmetics is used as an agent for keeping moisture on human skin because outer layer is composed of oil components, resulting in being capable of preventing dryness in the human skin.

It is to be noted that a water-in-oil type-emulsified composition for cosmetics is prepared by mixing a water-soluble high viscous compound such as glycerine, oils and/or waxes, water, and an emulsifier, etc.

As it does not have an affinity to water or sweat, properties are not diminished by those, preferably resulting in that the properties are durable for a long time of period.

Furthermore, an affinity to an oily makeup is high, resulting in that can be preferably employed as an excellent cleansing for the purpose of removing the oily makeup.

However, there are disadvantages that a water-in-oil type-emulsified composition for cosmetics unpreferably gives an oily or sticky feel when it is applied on human skin because outer layer is composed of oil components.

In order to solve the disadvantages, a water-in-oil type-emulsified composition for cosmetics containing a large amount of water has been numerously investigated, for example, as described in JP-B-26366/1985, JP-A-302935/1988, and JP-A-160709/1994.

However, the water-in-oil type-emulsified composition for cosmetics containing a large amount of water is not suitable for the purpose of removing the oily makeup because of high content of water. Furthermore, the water-in-oil type-emulsified composition for cosmetics containing a large amount of water is not thinly extended.

In the JP-A-160709/1994, it is described that a large amount of silicone oils which are slippery are employed as oil components for outer layer formed by a water-in-oil type-emulsified composition, and further viscosity of the composition is controlled within 20000 cps, whereby, thinness and an oily or sticky feel is improved.

Still further, sorbitan fatty acid esters composition or glycerine fatty acid esters composition which is a lipophilic emulsifier has been employed in the presence or absence of metal soaps of higher fatty acids for preparing the water-in-oil type-emulsified composition for cosmetics. In addition, there are recently employed organic compound-modified clays composition or mixed emulsifiers containing alpha-monoglyceryl ether.

However, in the case when the composition or emulsifiers are employed with a large amount of oils, viscosity thereof exceedingly lowers, resulting in that there cannot be readily obtained a water-in-oil type-emulsified composition for cosmetics having an excellent feel in use and excellent stability for a long time of period.

Besides, there is disclosed a water-in-oil type-emulsified composition for cosmetics having an excellent stability for a long time of period in JP-A-128135/1994 in which a fatty acid esters composition of a polyglycerine is employed. However, the composition is prepared by an esterification reaction of a polyglycerine with a fatty acid which in the preparation process No. (1) described hereinabove.

As described hereinabove, the composition prepared by an esterification reaction of a polyglycerine with a fatty acid has problems.

The problems in the water-in-oil type-emulsified composition for cosmetics can be solved by the use of the fatty acid esters composition of a polyglycerine containing high contents of a fatty acid monoester in the present invention.

As a specific example of cosmetics, a transparent liquid composition for cosmetics has been used as an agent for keeping moisture on human skin, cosmetics for bathroom, cosmetics for cleansing, cosmetics for a massage, cosmetics for a facial pack, cosmetics for hairs, and a base material for medicines, etc.

It is to be noted that a transparent liquid composition for cosmetics is prepared by mixing an non-ionic surface active agent, at least one of water-soluble compound having at least two hydroxyl groups, oils, and water, etc.

The transparent liquid composition for cosmetics usually contains oily components and plasticizers or emulsifiers which are usually non-ionic surface active agents.

It is known that the non-ionic surface active agents are relatively safe for human skin. Recently, the use of a fatty acid esters composition of a polyglycerine is proposed similarly to a fatty acid esters composition of sucrose instead of the non-ionic surface active agents from viewpoint of irritating skin.

However, a conventional fatty acid esters composition of polyglycerine is poorer in a solubilizing and emulsifying properly compared to non-ionic surface active agents having polyoxyethylene chains. Particularly, it is difficult to solubilize a large amount of oily components in water which is a base material, and as a composition for cosmetics is highly viscous, there has been a disadvantage that a feel in use is not heavy.

The problems in the transparent liquid composition for cosmetics can be solved by the use of the fatty acid esters composition of a polyglycerine containing high contents of a fatty acid monoester in the present invention.

As a specific example of cosmetics, a gel-like emulsified composition for cosmetics has been used as cosmetics for cleansing and cosmetics for a massage, etc.

It is to be noted that a gel-like emulsified composition for cosmetics is usually prepared by mixing glycerine, oils, a polyvalent alcohol except glycerine, and an emulsifier, etc.

It has been conventionally difficult to prepare a gel-like emulsified composition for cosmetics having a stability because of characteristic properties thereof. In order to prepare a gel-like emulsified composition having a stability, it has been uncommonly tried to make the composition itself high viscous at the sacrifice of a special characteristic and a feel in use.

Furthermore, although a gel-like emulsified composition for cosmetics has been numerously investigated with development of a hydrophilic fatty acid esters composition of a polyglycerine, there is a problem that a conventional fatty acid esters composition of a polyglycerine exhibits an unpleasant feel in use which is a poor spreadability because of its sticky property.

As a method for solving the problem, for instance, JP-A-224507/1992 discloses an instance that there are employed a fatty acid esters composition of polyoxyethylenesorbit and/or a fatty acid esters composition of polyoxyethyleneglycerine together with a fatty acid esters composition of diglycerine instead of a hydrophilic fatty acid esters composition of a polyglycerine, and JP-A-4911/1993 and JP-A-4912/1993 disclose instances that there are employed natural surface active agents.

However, the compositions are insufficient from a viewpoint of safety, there has been expected the development of a fatty acid esters composition of a polyglycerine having excellent safety, an excellent feel in use, and a special characteristic for a gel-like emulsified composition.

The expectation can be attained by the fatty acid esters composition of a polyglycerine containing high contents of a fatty acid monoester in the present invention.

The problems in the gel-like emulsified composition for cosmetics can be solved by the use of the fatty acid esters composition of a polyglycerine containing high contents of a fatty acid monoester in the present invention.

As a specific example of cosmetics, a composition for tooth paste contains a foaming agent in order to give a refreshing feel, a dispersing and emulsifying function, and a foaming function, and a surface active agent is employed for giving functions.

It is to be noted that a composition for tooth paste is usually prepared by mixing an abrasive such as secondary hydrated calcium phosphate, water-soluble compounds having high molecular weight such as a carboxymethyl cellulose, a wetting agent such as glycerine, and medicinal components, etc.

The surface active agent to be employed for giving functions is an essential component. The refreshing feel is teeth-brushing is enhanced by a decrease of surface tension owning to mixing it. Furthermore, the effect is enhanced by accelerating dispersion and permeation of the medicinal components owing to mixing it. Still further, the surface active agent sensuously gives stability by foaming in use.

As the composition for tooth paste is used in mouth, not only the surface active agent to be employed must possess excellent ability for decreasing surface tension and excellent ability for foaming, but also taste and odor must be satisfactorily acceptable.

Therefore, there have been conventionally employed anion surface active agents not having taste and odor such as a sodium alkylsulphate, sodium acylsalkosinate, alpha-olefin sulphonate, and a monoglyceride composed of sodium sulphate and a coconut oil, etc.

However, the anionic surface active agents have disadvantages that mucous membrane in mouth is irritated, tastes of foods are charged after using, and an effect by enzymes to be mixed as medicinal components in tooth paste is decreased. Furthermore, safeness has recently become problematic.

In view of situations, anionic surface active agents have advantages of milder irritation to skin and mucous membrane compared to anionic surface active agents. Furthermore, the anionic surface active agents have an advantage of not decreasing the effect by enzymes, and a fatty acid, esters composition of sucrose and a fatty acid esters composition of a polyglycerine are narrowly approved as surface active agents for food processing.

Therefore, a fatty acid esters composition of sucrose and a fatty acid esters composition of a polyglycerine are proposed as surface active agents for mixing in tooth paste.

However, a fatty acid esters composition of sucrose and a conventional fatty acid esters composition of a polyglycerine have disadvantages that those do not sufficiently foam in use, and an effect as tooth paste and a feel in use are exceedingly poor. It is only known that monolaurate of sucrose and monomyristate of sucrose were mixed (G. L. Fosol and P. Rovesti, (International Symposium on Sugarester) Maison de la Chimie Paris, Jun. 8, 1960).

The problems in the composition for tooth paste can be solved by the use of the fatty acid esters composition of a polyglycerine containing high contents of a fatty acid monoester in the present invention.

As a specific example of cosmetics, a cleaning agent composition is widely used in a variety of fields. Particularly, a cleaning agent composition importantly acts in food industries, In the food industries, it is used for cleaning foods themselves, starting materials for food processing, apparatuses for foods processing, and containers such as bottles or cans.

In the food industries, safeness of a cleaning agent composition is severely demanded because it possibly remains in apparatuses, containers, and foods themselves to be cleaned, resulting in that it is taken together with foods or beverages in human body.

Particularly, as a cleaning agent composition for the food industries is often used for foods themselves, there have been used a fatty acid esters composition of sucrose and a fatty acid esters composition of glycerine which are also additives for foods from viewpoint of safeness (Journal of Food Sanitation, vol. 18, No. 3, page 217).

Furthermore, JP-A-158090/1994 discloses that there is used a mixture composed of a monoglyceride composition of a polycarboxylic acid ester and a fatty acid esters composition of glycerine which are ionic surface active agents as a cleaning agent composition. However, the cleaning agent composition in the Journal and the mixture in the JP are not sufficient in cleaning ability.

The problems in the cleaning agent composition can be solved by the use of the fatty acid esters composition of a polyglycerine containing high contents of a fatty acid monoester in the present invention.

The cleaning agent composition of the present invention is harmless for human body and strong in cleaning ability, and it can be preferably used as a cleaning agent composition for foods, starting materials for foods, apparatuses for foods processing, and bottles, containers, and cans in food industries.

As a specific example of cosmetics, a foaming composition for cleaning is widely used as a cleaning agent in cosmetic fields and a detergent for a kitchen or bathroom.

For example, hair washing with a shampoo requires rinsing by water or warmed water after washing. However, in the case when a person cannot have a bath or cannot wash with water because of an injury, or in a place being incapable of using water, it is difficult to clean hair.

Therefore, there is proposed a wiping type cleaning agent which does not require rinsing.

Specifically, there are exemplified an aerosol type water-based cleaning composition in JP-B-47960/1982, a foaming hair cleaning agent in JP-A-289023/1986, a foaming hair cleaning agent for wiping a shampoo in JP-A-205011/1987, a dry hair cleaning method and an agent therefor in JP-A-14711/1988, and an aerosol type shampoo composition in JP-A-190813/1988, etc.

However, conventional compositions in which an electrolyte-based surface active agent is employed are not sufficient in stimulation to head skin and hair by only wiping, and spray-type conventional compositions in which a non-electrolyte-based surface active agent is employed are not satisfied because cleaning agents are scattered beyond necessary portions, and foam-type conventional compositions in which a non-electrolyte-based surface active agent is employed are not satisfied in cleaning ability and refreshing feeling because a mixing amount of alcohols is limited in order to prepare a foam type one.

Furthermore, JP-A-100435/1994 discloses that a non-electrolyte-based surface active agent such as a fatty acid esters composition of a polyglycerine is employed in combination with a higher alcohol to prepare a foaming composition for cleaning containing a large amount of the higher alcohol.

However, the conventional fatty acid esters composition of a polyglycerine is not prepared by the glycidol process (5) as described hereinabove. Accordingly, the content of a fatty acid monoester is low in the composition, resulting in that the foaming composition for cleaning does not satisfactorily exhibit sufficient stability for a long time of period, a cleaning effect, and a refreshing feel.

The problems in the foaming composition for cleaning can be solved by the use of the fatty acid esters composition of a polyglycerine containing high contents of a fatty acid monoester in the present invention.

As a result of an intensive investigation by the present inventors, the present invention has been completed.

SUMMARY OF THE INVENTION

It is an object of the present invention to provide a fatty acid esters composition of a polyglycerine containing more than 70% of a fatty acid monoester and a process for the preparation thereof.

It is another object of the present invention to provide a highly-purified fatty acid esters composition of a polyglycerine and a process for the preparation thereof.

It is other object of the present invention to provide the use of a fatty acid esters composition of a polyglycerine as an additive for food-stuffs, thermoplastic resins, cosmetics, and detergents.

A first aspect of the present invention relates to a fatty acid esters composition of a polyglycerine containing more than 70% of a fatty acid monoester represented by general formula (1) described below:

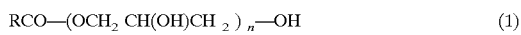

$$RCO-(OCH_2\ CH(OH)CH_2)_n-OH \quad (1)$$

wherein R is an alkyl group, an alkenyl group, or a hydroxyl group-substituted alkyl group which have a carbon number ranging from 6 to 21, and n is an integer of at least 4, based on a peak area ratio detected using an ultraviolet ray absorption detector tin a high performance liquid chromatographic analysis method.

A second aspect of the present invention relates to a process for the preparation of a fatty acid esters composition of a polyglycerine which comprises the reaction of a fatty acid represented by general formula (2) described below:

$$RCOOH \quad (2)$$

wherein R is an alkyl group, an alkenyl group, or a hydroxyl group-substituted alkyl group which have a carbon number ranging from 6 to 21, with glycidol in the presence of a phosphoric acid-based acidic catalyst.

A third aspect of the present invention relates to a process for the preparation of a highly-purified fatty acid esters composition of a polyglycerine which comprises the steps;

(a) allowing to react a fatty acid with glycidol to obtain a fatty acid esters composition of a polyglycerine, (b) removing water after adding water into said fatty acid esters composition of a polyglycerine, and then heating.

A fourth aspect of the present invention relates to a highly-purified fatty acid esters composition of a polyglycerine having an oxirane oxygen concentration of below 100 ppm, said oxirane oxygen concentration is defined by the titration method defined in Cd. 9-57 of Journal of American Oil Chemists' Society, or having a ratio of below 0.01%, said ratio is a peak area value of a chemical shift between 2.7 ppm and 2.8 ppm assigned by methylene proton derived from an oxirane group with respect to a peak area value of a chemical shift between 3.4 ppm and 4.4 ppm assigned by methylene proton and methine proton derived from a polyglycerine with a proton NMR.

A fifth aspect of the present invention relates to the use of a fatty acid esters composition of a polyglycerine in the first aspect or a highly-purified fatty acid esters composition of a polyglycerine in the fourth aspect for an additive for food-stuffs.

A sixth aspect of the present invention relates to a resin composition which comprises a fatty acid esters composition of a polyglycerine in the first aspect or a highly-purified fatty acid esters composition of a polyglycerine in the fourth aspect, and a thermoplastic resin.

A seventh aspect of the present invention relates to a water-in-oil type-emulsified composition for cosmetic which comprises glycerine, oils and/or waxes, water, and a fatty acid esters composition of a polyglycerine in the first aspect or a highly-purified fatty acid esters composition of a polyglycerine in the fourth aspect.

An eighth aspect of the present invention relates to a transparent liquid composition for a cleansing which comprises at least one of an non-ionic surface active agent, at least one of water-soluble compound having at least two hydroxyl groups, oily components, water, and a fatty acid esters composition of a polyglycerine in the first aspect or a highly-purified fatty acid esters composition of a polyglycerine in the fourth aspect, a highly-purified fatty acid esters composition of a polyglycerine in the fourth aspect or a highly-purified fatty acid esters composition of a polyglycerine in the fourth aspect, and an agent for spraying said mixture.

A ninth aspect of the present invention relates to a gel-like emulsified composition for cosmetic which comprises glycerine, liquid oily components, a polyvalent alcohol except glycerine, and a fatty acid esters composition of a polyglycerine in the first aspect or a highly-purified fatty acid esters composition of a polyglycerine in the fourth aspect.

A tenth aspect of the present invention relates to a composition for tooth paste which comprises an abrasive, a caking material, a wetting agent, and a fatty acid esters composition of a polyglycerine in the first aspect or a highly-purified fatty acid esters composition of a polyglycerine in the fourth aspect.

An eleventh aspect of the present invention relates to a cleaning agent composition which comprises (a) a polycarboxylic acid ester of a monoglyceride or a salt thereof represented by general formula (3)

$$R1-COO-CH_2-CHOZ1-CH_2OZ2 \quad (3)$$

wherein R1 is an alkyl or alkenyl group having a carbon number ranging from 7 to 17, either Z1 or Z2 is a residual group of a polycarboxylic acid or salt thereof, and another hydrogen atom or a residual group of a polycarboxylic acid or salt thereof, (b) a fatty acid esters composition of a polyglycerine as set forth in claim 1 or a highly-purified fatty acid esters composition of a polyglycerine as set forth in claim 14, (c) organic or inorganic builders, (d) fluidity improvers, and additionally (e) thickening agents, (f) perfumes, (g) coloring agents, (h) sterilizers, (i) enzymes, and (j) anti-inflammatory agents.

A twelfth aspect of the present invention relates to a foaming composition for cleaning which comprises a mixture composed of at least one of a lower monovalent alcohol having a carbon number ranging from 1 to 3, water, at least one of a higher alcohol having a carbon number ranging from 12 to 22, and a fatty acid esters composition of a polyglycerine in the first aspect or a highly-purified fatty acid esters composition of a polyglycerine in the fourth aspect.

BRIEF DESCRIPTION OF THE DRAWINGS

FIG. 10 is a chart obtained by HPLC relating to commercially supplied fatty acid esters composition of a polyglycerine employed in Comparative Example 11.

FIG. 24 is a chart obtained by HPLC relating to PGMLEC obtained in Example 28.

FIG. 25 is a chart obtained by HPLC relating to a commercially supplied fatty acid esters composition of a polyglycerine employed in Comparative Example 16.

FIG. 26 is a chart obtained by HPLC relating to a commercially supplied fatty acid esters composition of a polyglycerine employed in Comparative Example 17.

DETAILED DESCRIPTION OF THE INVENTION

Figure 1:
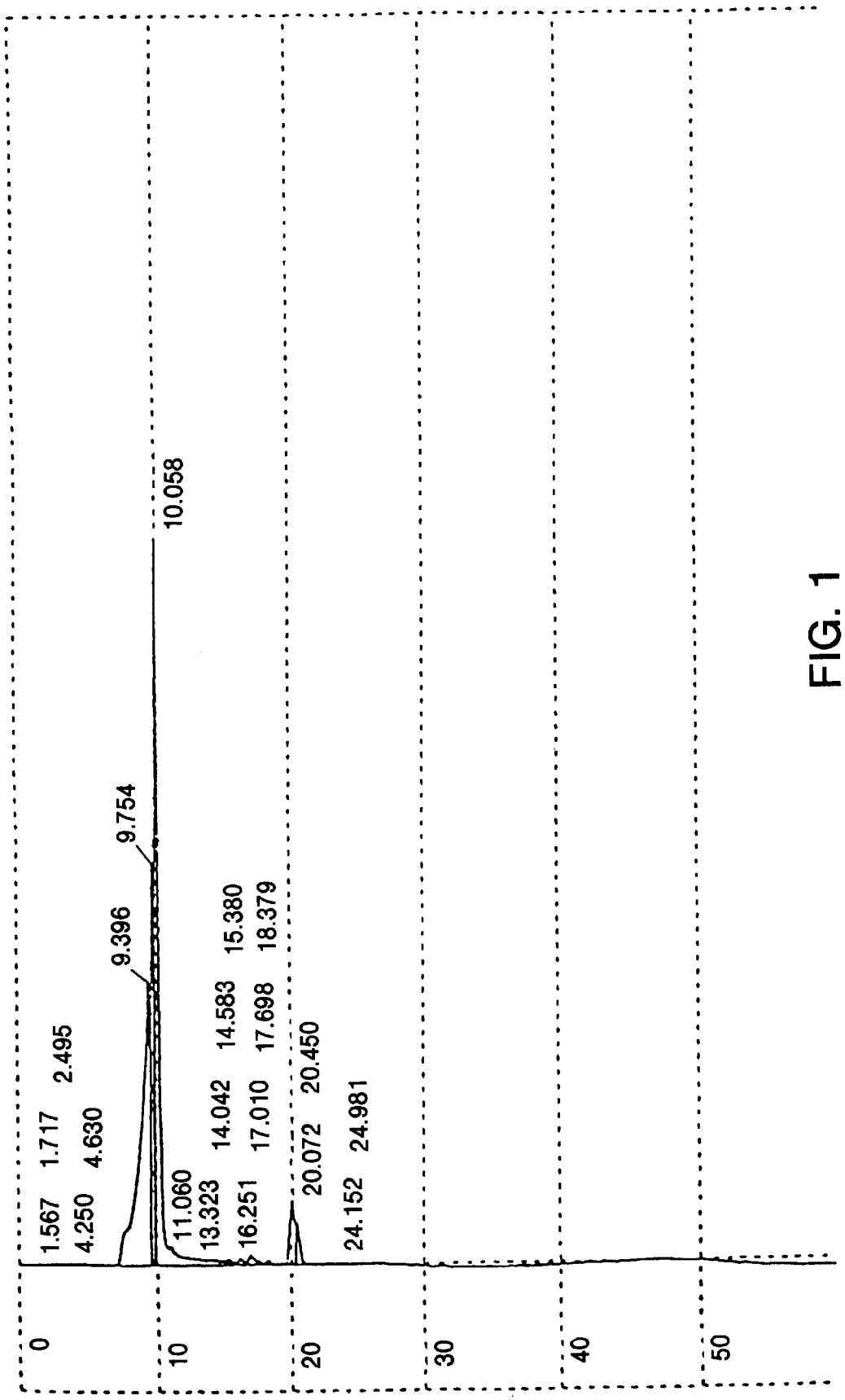
FIG. 1 is a chart obtained by a high performance liquid chromatography analysis (HPLC) relating to a lauric acid esters composition of a polyglycerine obtained in Example 1.

The present invention will be described hereinafter in more detail.

According to a first aspect of the present invention, there is provided a fatty acid esters composition of a polyglycerine containing more than 70% of a fatty acid monoester represented by general formula (1) described below:

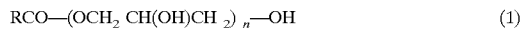

$$RCO-(OCH_2\ CH(OH)CH_2)_n-OH \qquad (1)$$

wherein R is an alkyl group, an alkenyl group, or a hydroxyl group-substituted alkyl group which have a carbon number ranging from 6 to 21, and n is an integer of at least 4, based on a peak area ratio detected using an ultraviolet ray absorption detector in a high performance liquid chromatographic analysis method.

According to a second aspect of the present invention, there is provided a process for the preparation of a fatty acid esters composition of a polyglycerine which comprises the reaction of a fatty acid represented by general formula (2) described below:

$$RCOOH \qquad (2)$$

wherein R is an alkyl group, an alkenyl group, or a hydroxyl group-substituted alkyl group which have a carbon number ranging from 6 to 21, with glycidol in the presence of a phosphoric acid-based acidic catalyst.

The fatty acid esters composition of a polyglycerine containing more than 70% of a fatty acid monoester represented by the general formula (1) of the first aspect of the present invention can be prepared by the process of the second aspect of the present invention.

As the fatty acid represented by the general formula (2, there are employed fatty acids having a carbon number ranging from 7 to 22 which may be a saturated or unsaturated acid, a linear aliphatic or branched acid and, further a substituted fatty acid in which hydroxyl groups are substituted for carbon chains. As an example of the fatty acids, there are specifically exemplified caproic acid, caprylic acid, 2-ethylhexanoic acid, capric acid, lauric acid, isotridecanoic acid, myristic acid, palmitic acid, palmitoreic acid, stearic acid, isostearic acid, oleic acid, linoleic acid, behenic acid, erucic acid, licinoleic acid, hydroxystearic acid, etc., which may be employed solely or in combination. The fatty acid may be employed solely or in combination.

It is to be noted that glycidol is another name of an epoxy alcohol which has the chemical structure of

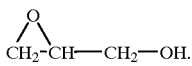

The fatty acid is allowed to react with glycidol in the presence of a phosphoric acid-based acidic catalyst.

The phosphoric acid-based acidic catalyst to be essentially employed in the present invention includes phosphoric acids or esters thereof. Specifically, there are exemplified phosphoric acids such as phosphoric acid, phosphoric anhydride, polyphosphoric acid, orthophosphoric acid, metaphosphoric acid, pyrophosphoric acid, triphosphoric acid, and tetraphosphoric acid, acidic esters of phosphoric acid such as methyl acid phosphate, ethyl acid phosphate, isopropyl acid phosphate, butyl acid phosphate, and 2-ethylhexyl acid phosphate, etc.

Furthermore, there an be also employed monoester compound, diester compound, and an admixture thereof. Of those, phosphoric acid and acidic esters of phosphoric acid are preferably employed. The catalyst may be employed solely or in combination.

The catalysts are employed in an amount ranging from 0.01 to 10% by weight, preferably from 0.1 to 5% by weight based on the fatty acid.

In the case when the amount is below 0.01% by weight, the reaction rate is low and, on the contrary, even in the case when the amount exceeds 10% by weight, the reaction rate is not promoted and, it is not only meaningless, but also addition polymers of glycidol itself preferably by-produce depending upon the catalysts which act as initiators.

The reaction is carried out by charging the fatty acid into a reaction vessel and adding the catalyst, followed by gradually adding glycidol. The reaction is carried out in temperatures ranging from 50 to 180° C., preferably from 70 to 160° C., and more preferably from 120 to 140° C.

In the case when the temperature is below 50° C. the reaction rate is slow and, on the contrary, in the case when it exceeds 180° C., products remarkably color, and in the case of exceeding 230° C., glycidol decomposes and side reactions are unpreferably caused. In order to prevent elevation of the temperatures, there can be employed a solvent having a low-boiling point which is inert to glycidol.

Furthermore, the reaction is preferably carried out under a nitrogen gas atmosphere which may be optionally pressurized.

The reaction may be carried out by a batch type or continuous type process.

The reaction solar ratio of glycidol do the fatty acid ranged from 1 to 100, preferably from 1 to 50 and, more preferably from 1 to 10.

In the case when the ratio is below 1, the fatty acid unreacted unpreferably remains in a reaction product and, on the contrary, in the case when the ratio exceeds below 100, there cannot be obtained a desired fatty acid esters composition of a polyglycerine.

Although solvents may be employed in the reaction, it is preferred that solvents are not employed in the use as additives for foods.

Examples of the solvents include an aromatic hydrocarbon such as benzene, toluene, and xylene, a halogenated toluene such as trifluorotoluene, an aliphatic ketone having a carbon number ranging from 3 to 9 such as methylisopropyl ketone, methylisobutylketone, diethylketone, and diisobutylketone, etc.

Furthermore, there can be employed ethers such as diisopropylether, etc. The solvent may be employed solely or in combination. In the case when the solvent is employed, it is employed in an amount of 2 times by weight at most based on the total weight of starting materials.

According to the above-described process, there can be obtained a fatty acid esters composition of a polyglycerine having a high polymerization degree. The fatty acid esters composition of a polyglycerine is an admixture composed of a monoester compound, a diester compound, and a triester compound.

The fatty acid esters composition of a polyglycerine of the present invention contains more than 70% of a fatty acid monoester represented by the general formula (1) described hereinabove.

In order to define the content of a fatty acid monoester compound in a fatty acid esters composition of a polyglycerine, there is employed a high performance liquid chromatographic analysis method (hereinafter, referred to as HPLC).

In the HPLC analysis method, a peak area ratio is detected using an ultraviolet (UV) ray absorption detector. The analytical condition may be selected from the following three conditions.

Analytical condition No. 1:
Column; 2 pieces (connected in series) of Wakosil 5C18 manufactured by Wako Jun-yaku Ltd. or equivalent, which is a reversed phase distribution column (an ODS column) having an octadecyl group as a functional group
Column size; 4.6 mm phi×250 mmL
Eluent for development; Methanol
Flow rate of the eluent; 0.05 to 1.0 ml/min (eg. 0.75 ml/min)
Column oven temperature; 30 to 60° C. (eg. 40° C.)
Wave length in UV ray absorption detector; 210 nm
Sample concentration; 1 to 50% (eg. 5% in methanol solution)
Sample volume; 0.1 to 20 micro liter (eg. 5 micro liter)
Retention time of polyglycerine; 8 minutes
Retention time of monoester compound; 8–12 minutes
Retention time of other ester compounds; >12 minutes
Retention time of methanol; exceeding 18 minutes Analytical condition No. 2:
Column; Wakosil II 5C18HG manufactured by Wako Jun-yaku Ltd. or equivalent, which is a reversed phase distribution column (an ODS column) having an octadecyl group as a functional group
Column size; 4.6 mm phi×250 mmL
Eluent for development; Methanol
Flow rate of the eluent; 0.05 to 1.0 ml/min (eg. 0.20 ml/min)
Column oven temperature; 30 to 60° C. (eg. 40° C.)
Wave length in UV ray absorption detector; 210 nm
Sample concentration; 1 to 50% (eg. 10% in methanol solution)
Sample volume; 0.1 to 20 micro liter (eg. 10 micro liter)
Retention time of polyglycerine; before 14 minutes
Retention time of monoester compound; 14–16.5 minutes
Retention time of other ester compounds; >16.5 minutes
Retention time of methanol; exceeding 18 minutes Analytical condition No. 3:

Column; Wakosil 5C18 and Wakosil II 5C18HG (connected in series) manufactured by Wako Jun-yaku Ltd. or equivalent, which is a reversed phase distribution column (an ODS column) having an octadecyl group as a functional group Column size; 4.6 mm phi×250 mmL Eluent for development; Ethanol Flow rate of the eluent; 0.05 to 1.0 ml/minute (eg 0.20 ml/min)

Column oven temperature; 30 to 60° C. (eg. 40° C.)

Wave length in UV ray absorption detector; 210 nm

Sample concentration; 1 to 50% (eg. 5% in ethanol solution)

Sample volume; 0.1 to 20 micro liter (eg. 10 micro liter)

Retention time of polyglycerine; below 28.5 minutes

Retention time of monoester compound; 28.5–34 minutes

Retention time of other ester compounds; exceeding 34 minutes

Retention time of ethanol; 39 minutes p As an eluent for development, there can be preferably employed an alcohol and a mixture composed of alcohol/water.

The eluent for development is selected depending upon the kind of a fatty acid of which a fatty acid esters composition of a polyglycerine is composed, and depending upon the amount of glycidol introduced. For example, in the case when a lauric acid esters composition of a polyglycerine is analyzed, methanol is preferably employed as the eluent, and in the case when a stearic acid esters composition of a polyglycerine is analyzed, ethanol is preferably employed as the eluent.

Samples (as a solution of an eluent for development) in the HPLC analysis method are employed in an amount ranging from 0.1 to 20 micro liter, preferably from 5 to 10 micro liter depending upon the solubility of samples into the eluent and the kind of samples. Sample concentration ranges from 1 to 50%, preferably from 5 to 10% in the eluent.

In separation by the HPLC analysis method using a column (an ODS column) having an octadecyl group, no-substituted polyglycerine components which have a higher polarity are firstly detected, and then fatty acid esters components of a polyglycerine are detected.

In the fatty acid esters components, monoester compound is firstly detected, and then diester compound is detected, and further other ester (triester, tetraester, . . . ) compounds are detected. The content of the monoester compound is calculated according to the following equation.

Content of a monoester compound=(A/(B-C)) ×100 (%)

A: peak area from the beginning in detection of fatty acid esters of a polyglycerine to detection of fatty acid monoester compound B: total peak area of all components C: peak area of solvent Speaking of peak area by a solvent, it is to be noted that it is important to select a solvent so that a retention time by the solvent does not overlap retention time by other components.

The above-described equation for calculating the content of a monoester compound is based on the premise that a retention time by the solvent is present before retention time by other components.

There may be optionally refined the fatty acid esters composition of a polyglycerine containing more than 70% of a fatty acid monoester of the present invention.

As methods for refining, there are exemplified;

(1) A method for removing odor by a steam injection process in which saturated steam is blown at reduced pressures.

(2) A method for decoloration by a bleaching process using sodium hypophosphate or hydrogen peroxide.

According to a third aspect of the present invention, there is provided a process for the preparation of a highly-purified fatty acid esters composition of a polyglycerine which comprises the steps;

(a) allowing to react a fatty acid with glycidol to obtain a fatty acid esters composition of a polyglycerine, (b) removing water after adding water into said fatty acid esters composition of a polyglycerine, and then heating.

The highly-purified fatty acid esters composition of a polyglycerine of the present invention is prepared by the two steps (a) and (b).

The step (a) corresponds to the above-described reaction process in the second aspect of the present invention.

A product obtained in the step (a) corresponds to the above-described fatty acid esters composition of a polyglycerine in the first aspect of the present invention.

It is to be noted that the fatty acid esters composition of a polyglycerine obtained in the step (a) usually contains oxirane oxygen ranging from 500 to 2000 ppm based on a titration method described hereinafter.

The step (b) is described below in detail.

In the step (b), water is added into the fatty acid esters composition of a polyglycerine obtained in the step (a), and then the composition is heated, followed by removing water.

In the step (b), water is added in an amount ranging from 0.1 to 20% by weight, and preferably from 1 to 10% by weight based on the weight of the above described fatty acid esters composition of a polyglycerine.

In the case when the amount of water is below 0.1%, unreacted glycidol cannot be sufficiently decreased and, on the contrary, in the case when the amount of water exceeds 20%, it unpreferably requires a long time of period for removing water.

Unreacted glycidol is changed to glycerine by heating after adding water. Heating temperature in the step (b) ranges from 60 to 200° C., and preferably from 80 to 160° C.

In the case when the temperature is below 60° C., unreacted glycidol cannot be sufficiently decreased and, on the contrary, in the case when the temperature exceeds 200° C., there unpreferably colors the fatty acid esters composition of a polyglycerine.

Heating time of period ranges from 0.5 to 15 hours, and preferably from 1 to 7 hours depending upon heating temperatures.

In the case when the heating time is below 0.5 hour, glycidol cannot be sufficiently decreased and, on the contrary, in the case when the time exceeds 15 hours, there unpreferably colors the fatty acid esters composition of a polyglycerine.

In the step (b), water is removed after the completion of heating to obtain the fatty acid esters composition of a polyglycerine not containing unreated glycidol.

Water can be removed by distillation, azeotropic distillation, and distillation under reduced pressures.

Heating temperatures in distillation ranges from 100 to 200° C., and preferably from 110 to 160° C.

In the case when the distillation temperature is below 100° C., water cannot be sufficiently removed and, on the contrary, in the case when the temperature exceeds 200° C., there unpreferably colors the fatty acid esters composition of a polyglycerine.

Distillation time of period ranges from 1 to 10 hours, and preferably from 1 to 6 hours depending upon temperatures and the degree of reduced pressures in distillation.

In the case when the distillation time is below 1 hour, water cannot be sufficiently removed and, on the contrary, in the case when the time exceeds 10 hours, there unpreferably colors the fatty acid esters composition of a polyglycerine.

In the case when a solvent is employed in the step (a), it can be removed in the distillation together with water.

According to a fourth aspect of the present invention, there is provided a highly-purified fatty acid esters composition of a polyglycerine having an oxirane oxygen concentration of below 100 ppm, said oxirane oxygen concentration is defined by the titration method defined in C. 9-57 of Journal of American Oil Chemists' Society, or having a ratio of below 0.01%, said ratio is a peak area value of a chemical shift between 2.7 ppm and 2.8 ppm assigned by methylene proton derived from an oxirane group with respect to a peak area value of a chemical shift between 3.4 ppm and 4.4 ppm assigned by methylene proton and methine proton derived from a polyglycerine with a proton NMR.

In order to determine the concentration value of oxirane oxygen in the highly purified fatty acid esters composition of a polyglycerine of the fourth aspect, there is employed the titration method defined in Cd. 9-57 of Journal of American Oil Chemists' Society, (Journal of American Oil Chemists' Society, 41, 86-87 (1964)) or having a ratio of below 0.01%, said ratio is a peak area value of a chemical shift between 2.7 ppm and 2.8 ppm assigned by methylene proton derived from an oxirane group with respect to a peak area value of a chemical shift between 3.4 ppm and 4.4 ppm assigned by methylene proton and methine proton derived from a polyglycerine with a proton NMR.

The titration method defined in the tentative method Cd. 9-57, Oxirane Oxygen by D. S. Bolly et al and cited in the Journal of American Oil Chemists' Society Volume 41, pp. 86–87 (1964) is a method for measuring oxirane oxygen which is described below.

Definition: This method determines oxirane oxygen which is the oxygen contained in the following grouping:

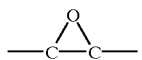

Under the prescribed conditions of this method, the oxygen is titrated directly with hydrogen bromide in acetic acid.

Scope: Applicable to epoxidized fatty materials and epoxy compounds in general.

A. Apparatus:
1. Buret assembly of the Machlette type (gravity feed), available from Scientific Glass Apparatus Co. Cat. No. JB6715 or equivalent. Provide a closed system for titration to avoid loss of hydrogen bromide attaching the titration flask to the buret tip with a one-hole rubber stopper. The hole in the stopper should be formed so as to take the buret tip snugly with a small side opening to permit air to escape from the flask during titration.
2. Flask: Erlenmeyer, 50 ml,
3. A magnetic stirrer of any suitable type with round magnetic stirring bars covered with "Teflon" or equivalent protective covering.

B. Reagents:
1. Glacial acetic acid, A.C.S. grade, acetic anhydride free
2. Hydrogen bromide gas, anhydrous, available in cylinders from Matheson Company, Inc., Joliet, Ill. or 30–32% hydrogen bromide in acetic acid available from Eastman Kodak Co.
3. Crystal violet (Gentian violet), Eastman Kodak No. 1350 or equivalent.
4. Acid potassium Phthalate, National Bureau of Standard, Standard for Acidimetry. Dry for two hours at 120° C. and allow to cool in an efficient desiccator prior to use.
5. Benzene, A.C.S. grade or chlorobenzene, analytical reagent grade.

C. Solutions:
1. Crystal violet indicator soln.; dissolve 0.1 g. of crystal violet in 100 ml. of glacial acetic acid.
2. Hydrogen bromide 0.1 N in acetic acid.
   a. Prepare by bubbling hydrogen bromide gas through glacial acetic acid to approximately 0.1N. A torsion type balance may be use to estimate the amount of hydrogen bromide added.
   b. or, prepare by diluting 30 to 32% (about 4N) hydrogen bromide in acetic acid with glacial acetic acid to approximately 0.1N.

Standardization: Weigh accurately about 0.4 g. of dry acid potassium phthalate and dissolve in 10 ml. glacial acetic acid. Heat carefully dissolve, using a hot plate. Titration solution at room temperature with hydrogen bromide using no more than 0.1 ml. (5 drops from a fine dropper) of crystal violet indicator. Standardization should be in duplicate with a difference not to exceed 0.0004 N. Restandardize each day samples are analyzed.

Normality =(Weigh of Phthalate)/(0.2042×Titration)

D. Procedure:
1. Weight 0.3–0.5 g. (plus or minus 0.0001 g.) of the sample into a 50 ml. Erlenmeyer flask. Dissolve the sample in 10 ml of benzene or chlorobenzene (in case of epoxy resins use chlorobenzene). Add stirring bar and crystal violet indicator (maximum 0.1 ml. or 5 drops with a fine dropper).
2. Place the rubber stopper in position and lower the tip of the buret until it discharges just above the solution.
3. Stir and titrate the sample (rapidly at first) with the 0.1 N hydrogen bromide solution to a bluish-green end point that persists for 30 seconds. Control the rate of the magnetic stirrer so as to avoid splashing.

E. Calculation:
Oxirane Oxygen, %=(Titration×N×1.60)/(Weight of sample)

F. Responsibility:
The average variance of components calculated from the collaborative data obtained by the investigating Committee indicate the following 95% probability limits:
1. The difference between duplicate determinations made within a laboratory should not exceed . . . 0.8
2. The difference between the average or duplicate determinations made in different laboratories should not exceed . . . 0.19

G. Note:
1. This method is not applicable to oils containing alpha and beta-unsaturated ketones, cyclopropenes-conjugated dienols, oxidized fats, and soaps.
2. Long standing has a deleterious effect on hydrogen bromide solutions and should be avoided.

In the proton NMR method in order to determine the concentration value of oxirane oxygen in the highly purified fatty acid esters composition of a polyglycerine, methane-deuterium chloride ie employed as a solvent, the solution concentration of the fatty acid esters composition of a polyglycerine is approximately 5%, temperature for measuring is 40° C. plus or minus 0.5° C., and JOEL270Mz (manufactured by Nihon Denshi, Ltd.) or equivalent is employed as an NMR apparatus.

Although starting materials for the highly-purified fatty acid esters composition of a polyglycerine having an oxirane oxygen concentration of below 100 ppm or having the ratio of below 0.01% can be obtained by the process of the above-described second aspect or the step (a) in the third aspect, preparation processes thereof are not particularly limited.

Starting materials for the highly-purified fatty acid esters composition of a polyglycerine having an oxirane oxygen concentration of below 100 ppm or having the ratio of below 0.01% may also be provided by any one of the above-described preparation processes, that is, (1) an esterification reaction of a polyglycerine with a fatty acid, (2) a transesterification reaction of a polyglycerine with a fatty acid ester, (3) a transesterification reaction of a polyglycerine with an oil and fatty acid, (4) an addition polymerization reaction of glycidol to a monoglyceride of a fatty acid including (5) an addition polymerization reaction of glycidol to a fatty acid, etc.

The starting materials for the highly- purified fatty acid esters composition of a polyglycerine contain an oxirane oxygen ranging from 100 to 2000 ppm which is measured by the titration method defined in the Cd. 9–57 of Journal of American Oil Chemists' Society.

According to a fifth aspect of the present invention, there is provided the use of a fatty acid esters composition of a polyglycerine in the first aspect or a highly-purified fatty acid esters composition of a polyglycerine in the fourth aspect for an additive for food-stuffs.

As examples of the food-stuffs to be applied, there are specifically exemplified a material for drinks such as a cacao, coffee, and tea, a starch-based product such as noodles, kneaded bread-stuffs or bread, cookies, and cake, a dairy product such as a milk fermented by lactic acid, butter, and cheese, processed meat or processed fish meat, and an oils&fats composition which is composed of vegetable oils and/or hydrogenated animal or fish oils and other additives, etc.

As an additive for a variety of the food-stuffs, the fatty acid esters composition of a polyglycerine in the first or fourth aspect is employed in an amount ranging from 0.01% to 5% by weight, preferably from 0.05 to 2% by weight, and more preferably from 0.01 to 1% by weight based on the total amount of the food-stuffs including water, although it depends upon the kind of the food-stuffs.

In the case when the amount is below 0.01%, effect by the use is meaninglessly small and, on the contrary, in the case when the amount exceeds 5%, a taste or flavor inherently possessed in the food-stuffs is adversely affected.

The fatty acid esters composition of a polyglycerine acts as a stabilizer for emulsifying, an emulsifier or an accelerator thereof, a surface active agent, a dispersant, a binder, or a plasticizer for a variety of food-stuffs.

Effect by the use of the fatty acid esters composition of a polyglycerine is more specifically described below relating to respective food-stuffs.

In the case when the fatty acid esters composition of a polyglycerine of the present invention is employed in kneaded bread-stuffs, fermentation by yeast for bread is stabilized for long time of period even without controlling temperatures, resulting in that there can be prepared bread having an excellent taste.

For the kneaded bread-stuffs which are one of the starch-based product, the fatty acid esters composition of a polyglycerine is employed in an amount of less than 0.5% by weight together with other additives such as approximately 0.1% by weight of calcium carbonate, approximately 0.1% by weight of powdered egg white, and a small amount of salt, seasoning, and flavors, etc. based on flour. Fermentation by yeast for bread of the kneaded bread-stuffs is carried out at temperatures of 25 to 30° C. for 10 to 24 hours.

For noodles which are one of the starch-based products, the fatty acid esters composition of a polyglycerine is employed in an amount ranging from 0.1 to 0.5% by weight based on the weight of flour together with other additives such as salt and egg white, etc.

In the case when the fatty acid esters composition of a polyglycerine of the present invention is employed in noodles, it acts as a surface active agent, resulting in that adhering of noodles itself can be prevented.

In the case when the fatty acid esters composition of a polyglycerine of the present invention is employed in the dairy product, it acts as a dispersant or an emulsifier, resulting in that separation of fats can be prevented.

For the milk fermented by lactic acid which is one of the dairy product, the fatty acid esters composition of a polyglycerine is employed in an amount ranging from 0.02 to 0.15% by weight based on the weight of milk together with other additives such as sugar, etc.

Separation or flotation of fats is not caused in the milk fermented by lactic acid in which the fatty acid esters composition of a polyglycerine is mixed even at low temperatures such as 5° C. or high temperatures such as 30° C. for a long time of period such as 3 months.

For meat or fish meat, the fatty acid esters composition of a polyglycerine is employed in an amount ranging from 0.1 to 5% by weight, preferably from 0.5 to 1% based on the weight of meat or fish meat including moisture together with other additives such as salt and egg white, etc.

In the case when the fatty acid esters composition of a polyglycerine of the present invention is employed in the meat or fish meat, it acts as a elasticity improver and a whiteness improver.

The fatty acid esters composition of a polyglycerine of the present invention can be employed together with a oils&fats composition such as soy bean oil, etc. as an emulsifier for bread-stuffs, cake, and cookies, etc. as described in JP-A-22690/1994, together with an oils & fats composition for butter cake as described in JP-A-53/1994, together with water, sorbitol, lactose, and whey protein, etc. for sponge cake or snack cake as described in JP-A-269244/1994, as an O/W type-emulsified oil&fat composition which contains water, oils & fats, a glucide such as sorbitol, and an emulsifier as described in JP-A-78672/1994, together with a fatty acid ester of sugar, a fatty acid ester of glycerine, a fatty acid ester of sorbitan, a crystallized cellulose, etc. as a stabilizer for emulsifying as described in JP-A-125711/1994, together with cacao components, milk components, a sweetening agent, and water as an emulsifier for a cacao drink as described in JP-A-38682/1994, together with egg, starch, and vegetable oils, etc. as an emulsifier for noodles as described in JP-A-276972/1994 and JP-A-197717/1994, as an improver for fish meal as described in JP-A-22730/1994 as an improver for scallop meal as described in JP-A-90713/1994, as a plasticizer for granules containing proteins as described in JP-A-133735/1994, as an emulsifier for a W/O type oil & fat composition as described in JP-A-209704/1994, as a stabilizer for a wheat powder composition as described in JP-A-253718/1994, as an emulsifier for an oils & fats composition as described in JP-A-14711/1994, as an emulsifier for a fermented milk or cheese as described in JP-A-113799/1994, as a stabilizer for an extract from plants as described in JP-A-153884/1994, as a stabilizer for starch-based food-stuffs as described in JP-A-225684/1994, as a stabilizer for an oils & fats-containing fermented drink as described in JP-A-62734/1994, as a stabilizer for a water-containing chocolate base as described in JP-A-189682/1994, as a stabilizer for an oils & fats composition as described in JP-A-90663/1994, and as an emulsifier for food-stuffs containing proteins as described in JP-A-113727/1994, etc.

According to a sixth aspect of the present invention, there is provided a resin composition which comprises a fatty acid esters composition of a polyglycerine in the first aspect or a highly-purified fatty acid esters composition of a polyglycerine in the fourth aspect, and a thermoplastic resin.

As examples of the thermoplastic resin to be applied, there are specifically exemplified a polyvinyl chloride resin, a styrene-based resin, a methylmethacrylate-based resin, and a polyacetal resin, etc.

The fatty acid esters composition of a polyglycerine of the first aspect and a highly-purified fatty acid esters composition of a polyglycerine of the fourth aspect in the present invention act as a plasticizer, an improver of a wetting ability for a hydrophobic resin, an improver of a printing property, an anti-static agent, a releasing agent, or an anti-clouding agent, etc. for a variety of thermoplastic resins.

As an additive for a variety of thermoplastic resins, the fatty acid esters composition of a polyglycerine in the first and fourth aspects are employed in an amount ranging from 0.01% to 10% by weight, preferably from 0.05 to 5% by weight, and more preferably from 0.1 to 3% by weight based on the amount of the resins, although it depends upon the kind of the thermoplastic resins.

Mixing or kneading of the fatty acid esters composition of a polyglycerine with the thermoplastic resins can be carried out without any limitations by a single or twin screw extruder, a kneader, a roll mixer, a tumble mixer, a Brabender type mixer, a Henshell mixer, and a Banbury mixer which have been conventionally employed.

Furthermore, monomers can also be polymerized in the presence of the fatty acid esters composition of a polyglycerine depending upon the kind of thermoplastic resins.

In the case when the fatty acid esters composition of a polyglycerine is employed as an additive for a variety of thermoplastic resins, it can be employed solely or in combination.

Still further, in the case when the fatty acid esters composition of a polyglycerine is employed as an additive for thermoplastic resins, it can be employed together with other conventional additives such as an anti-oxidant which includes a hindered phenol-based or sulphur-based compound, a stabilizer, a flame retardant, a slipping agent, a nucleating agent, an ultraviolet absorbent, a releasing agent, a coloring agent, pigments, fibers, and fillers such as fiber glass or glass beads, etc., depending upon uses.

A resin composition in which a resin is mixed with the fatty acid esters composition of a polyglycerine of the first aspect or the fourth aspect in the present invention and other additives can be molded by extruding molding, injection molding, compression molding, vacuum molding, blow molding, and foamed molding, etc.

For example, in the case when the fatty acid esters composition of a polyglycerine of the first aspect or fourth aspect is employed as an additive for a polyvinyl chloride resin for the purpose of preparing a resin composition, particularly, it effectively acts as an anti-static agent.

A polyvinyl chloride resin may be molded as a film or a molded article which includes a plasticized or rigid polyvinyl chloride resin.

The fatty acid esters composition of a polyglycerine of the first aspect or fourth aspect is employed in an amount ranging from 1 to 10 parts by weight, and preferably from 2 to 7 parts by weight based on 100 parts of the polyvinyl chloride resin.

In the case when the amount is below 1 part by weight, an anti-static effect is poor and, on the contrary, in the case when the amount exceeds 10 part by weight, not only transparency of films decreases but also workability in molding process of the films unpreferably decreases.

The fatty acid esters composition of a polyglycerine of the first aspect or the highly purified fatty acid esters composition of a polyglycerine of the fourth aspect may be employed solely or in combination, and further may be employed together with conventional anti-static agents such as fatty acid esters of a glycerine, fatty acid esters of sorbitan, and sodium alkylsulfonates, etc.

The polyvinyl chloride resin to be employed in the present invention includes homopolymers and copolymers with olefines such as ethylene or propylene, vinyl acetate, and vinylidene chloride.

Furthermore, the fatty acid esters composition of a polyglycerine may be optionally employed together with conventional additives such as thermal stabilizers, anti-oxidants, reinforcing materials, processing agents, ultraviolet absorbents, slipping agents, coloring materials such as dyes, and pigments, etc.

In the meantime, for example, in the case when the fatty acid esters composition of a polyglycerine of the first aspect or the highly purified fatty acid esters composition of a polyglycerine of the fourth aspect is employed as an additive for a styrene-based resin for the purpose of preparing a resin composition, particularly, it effectively acts as an anti-clouding agent or an anti-static agent.

As specific examples of the styrene-based resin, there are exemplified a styrene homopolymer, a high impact polystyrene, an acrylonitrile-styrene copolymer, a styrene-methylmethacrylate copolymer, and a styrene-methylmethacrylate-acrylonitrile copolymer.

In particular, in the case when it is employed as an additive for a styrene-based resin film for the purpose of wrapping food-stuffs, it is exceedingly effective.

The fatty acid esters composition of a polyglycerine of the first aspect or the highly purified fatty acid esters composition of a polyglycerine of the fourth aspect is employed in an amount ranging from 0.5 to 8.0% by weight, and preferably from 1 to 5% by weight based on the weight of the styrene-based resin.

In the case when the amount is below 0.8% by weight, an anti-clouding effect is poor and, on the contrary, in the case when the amount exceeds 8% by weight, the anti-clouding agent excessively bleeds out of the films, resulting in that film surfaces are unpreferably sticky.

In the case when the fatty acid esters composition of a polyglycerine of the first aspect or the highly purified fatty acid esters composition of a polyglycerine of the fourth aspect is employed as an additive for a styrene-methylmethacrylate-acrylonitrile resin which is one of the styrene-based resin, particularly, it effectively acts as an anti-static agent.

The styrene-based resin includes styrene units ranging from 100% to 20% by weight, and there may be included methyl methacrylate units ranging from 0% to 80% by weight and acrylonitrile units ranging from 0% to 20% by weight as other units.

Furthermore, the styrene-based resin can be mixed with the fatty acid esters composition of a polyglycerine of the first aspect or the highly purified fatty acid esters composition of a polyglycerine of the fourth aspect in combination with phosphorus compounds and further optionally a polyalkylene glycol for the purpose of preparing a transparent resin composition having an excellent anti-static property.

As examples of the phosphorus compounds to be employed in the present invention, there are exemplified tributyl phosphite, triisooctyl phosphite, tribenzyl phosphite, triphenyl phosphite, phenyldidecyl phosphite, diphenylisodecyl phosphite, trisnonyl phenyl phosphite, tridecyl phosphite, trisstearyl phosphite, distearylpentaerythritol diphosphite, and the like.

Of those, there are preferably employed tridecyl phosphite, trisstearyl phosphite, and distearylpentaerythritol diphosphite.

The fatty acid esters composition of a polyglycerine of the first aspect or the highly purified fatty acid esters composition of a polyglycerine of the fourth aspect is employed in an amount ranging from 0.5 to 6.0 parts by weight, and preferably from 1.0 to 5 parts by weight based on 100 parts by weight of the transparent resin composition.

In the case when the amount is below 0.6 part by weight, an anti-static effect is poor and, on the contrary, in the case when the amount exceeds 6.0 parts by weight, the esters composition unpreferably bleeds out of articles, and further the surface of a mold becomes unpreferably dirty.

The phosphorus compounds are employed in an amount ranging from 0.05 to 4.0 parts by weight, and preferably from 1.0 to 3.0 parts by weight based on 100 parts by weight of the transparent resin composition.

In the case when the amount is below 0.05 part by weight, an anti-static effect is unpreferably poor and, on the contrary, in the case when the amount exceeds 4.0 parts by weight, the phosphite compounds adhere to surface of a mold or a molded article, unpreferably resulting in that a molded article becomes dirty.

The polyalkylene glycol which is an optional component is employed in an amount ranging from 0.5 to 5.0 parts by weight, and preferably from 1.0 to 4.0 parts by weight based on 100 parts by weight of the transparent resin composition.

In the case when the amount is below 0.5 part by weight, an effect for accelerating the anti-static is unpreferably poor and, on the contrary, in the case when the amount exceeds 5.0 parts by weight, the polyalkyleneglycol oozes out of an molded article, unpreferably resulting in that a molded article becomes dirty.

The polyalkylene glycol has a molecular weight ranging from 200 to 1500, and preferably from 300 to 1000. In the case when the molecular weight is below 200, compatibility with the resin becomes unpreferably poor and, on the contrary, in the case when the molecular weight exceeds 1500, an effect for accelerating the anti-static becomes unpreferably poor.

The styrene-based resin, the fatty acid esters composition of a polyglycerine, the phosphorus compounds, and optionally the polyalkylene glycol can be mixed with the conventional mixers described hereinabove.

In the meantime, for example, in the case when the fatty acid esters composition of a polyglycerine of the first aspect or the highly purified fatty acid esters composition of a polyglycerine of the fourth aspect is employed as an additive for a methyl-methacrylate-based resin for the purpose of preparing a resin composition, particularly, it effectively acts a releasing agent in a molding process.

Methylmethacrylate-based resin in the present invention includes a methylmethacrylate homopolymer and a copolymer with acrylates such as methylacrylate, ethylacrylate, butylacrylate, methacrylates such as ethylmethacrylate, butylmethacrylate, cyclohexylmethacrylate, acrylic acid, methacrylic acid, styrene, acrylonitrile, diene-based monomers, glutaric acid anhydride, and gulutarimide, etc.

In the case when the fatty acid esters composition of a polyglycerine of the first aspect or the highly purified fatty acid esters composition of a polyglycerine of the fourth aspect is employed as a releasing agent for a methylmethacrylate-based resin, it is preferably employed together with pentaerythritols or fatty acid esters thereof in order to accelerate a releasing effect.

The pentaerythritols include monopentaerythritol, dipentaerythritol, tripentaerythritol, tetrapentaerythritol, and adducts of 1 to 5 mol of ethyleneoxide or propyleneoxide with the pentaerythritols.

Furthermore, the fatty acid esters thereof include esters of the pentaerythritols with fatty acids such as caproic acid, caprylic acid, 2-ethylhexanoic acid, capric acid, lauric acid, isotridecanoic acid, myristic acid, palmitic acid, palmitoreic acid, stearic acid, isostearic acid, oleic acid, linoleic acid, behenic acid, erucic acid, licinoleic acid, and hydroxystearic acid, etc.

The pentaerythritols or the fatty acid esters thereof are employed in a ratio ranging from 10/90 to 90/10, and preferably from 25/75 to 75/25 based on the weight of the fatty acid esters composition of a polyglycerine.

The fatty acid esters composition of a polyglycerine of the first aspect or fourth aspect or a mixture with the pentaerythritols or the fatty acid esters thereof is employed in an amount ranging from 0.01 to 5% by weight, and preferably from 0.1 to 0.2% by weight based on the weight of the methylmethacrylate-based resin.

In the case when the amount is below 0.01% by weight, a releasing effect is insufficient and, on the contrary, in the case when the amount exceeds 0.5% by weight, not only transparency of the resin is unpreferably adversely affected, but also the releasing agents move to the surface of molded articles, unpreferably resulting in that the surface of the mold or molded articles becomes dirty by excessive amounts of the releasing agent, and commercial values remarkably decrease by coloration of the molded article.

Furthermore, there may be optionally mixed conventional additives such as hindered amine-based light stabilizers, hindered phenol-based, phosphorus-based, and sulphur-based anti-oxidants, reinforcing materials such as glass fibers, processing agents, ultraviolet absorbents, slipping agents, flame-retardants, weatherable agent, coloring agents such as dyes, and thermal stabilizers, etc.

In the meantime, for example, in the case when the fatty acid esters composition of a polyglycerine of the first aspect or the highly purified fatty acid esters composition of a polyglycerine of the fourth aspect can be employed as an additive for a polyacetal resin for the purpose of preparing a resin composition, particularly, it effectively acts as an agent for improving a printing property, an agent for improving wetting property to water, water-based inks, and an aqueous serum, and an agent for improving releasing property from a molding die.

Furthermore, the excellent properties endure for a long time of period.

In the case when the fatty acid esters composition of a polyglycerine of the first aspect or the highly purified fatty acid esters composition of a polyglycerine of the fourth aspect is employed as an agent for improving a printing property, it is employed in an amount ranging from 0.01 to 5 parts by weight, and preferably from 0.03 to 1 parts by weight, and more preferably from 0.05 to 0.08 part by weight based on 100 parts of the polyacetal resin.

In the case when the amount is below 0.01 part by weight, an effect for improving printing property is small and, on the contrary, in the case when the amount exceeds 5 parts by weight, thermal stability unpreferably decreases, and silver streak is caused by decomposed gases when molded, unpreferably resulting in that outer appearances of molded articles become remarkably poor.

In the case when the fatty acid esters composition of a polyglycerine of the first aspect or the highly purified fatty acid esters composition of a polyglycerine of the fourth aspect is employed as an additive for improving a wetting property, it is employed in an amount ranging from 0.01 to 0.4% by weight, and preferably from 0.05 to 0.3% by weight, and more preferably from based on the weight of the polyacetal resin.

In the case when the amount is below 0.01% by weight, an effect for improving wetting property is small and, on the contrary, in the case when the amount exceeds 0.4% by weight, mechanical property unpreferably decreases, and melt viscosity occasionally decreases, unpreferably resulting in that molding conditions are remarkably limited for the purpose of manufacturing a delicate part such as an ink jet nozzle in a printer for a personal computer.

In the case when the fatty acid esters composition of a polyglycerine of the first aspect or fourth aspect is mixed with the polyacetal resin in an amount ranging from 0.01 to 0.4% by weight, a resin composition has Melt Index (based on ASTM D1238-89) of below 1.5, an article molded from the resin composition has a contact angle of below 50, resulting in being preferred for the purpose of manufacturing a delicate part such as an ink jet nozzle in a printer for a personal computer.

The polyacetal resin to be employed in the present invention includes a high molecular weight compound having oxymethylene groups —$CH_2O$—. More specifically, there are included an oxymethylene homopolymer (—$CH_2O$—)n- which is prepared by polymerization of formaldehyde or a cyclic oligomer such as trimer (trioxane) of formaldehyde and tetramer (tetraoxane) of formaldehyde. Furthermore, there is included an oxymethylene copolymer having a structure, for example, such as (—$CH_2O$—)n- - (—$CH_2$—$CH_2O$—)m- having 0.1 to 20% by weight of oxyalkylene units containing a carbon number ranging from 2 to 8.

The copolymer is prepared by a reaction of formaldehyde or a cyclic oligomer such as trimer (trioxane) of formaldehyde and tetramer (tetraoxane) of formaldehyde with a cyclic ether such as ethylene oxide, propylene oxide, epichlorohydrin, 1,3-dioxolan, a formal of a glycol, and a formal of a diglycol, etc.

Still further, there is included an oxymethylene block copolymer having more than 50% by weight of recurring units a branched oxymethylene copolymer or oxymethylene and less than 50% by weight of other polymer units.

In addition, there can be blended at least one of an oxymethylene homopolymer, an oxymethylene copolymer, a branched polymer, and an oxymethylene block copolymer.

There is preferably employed a polyacetal resin having an FR value (ASTM D1238-57E) of 20–100 g/10 minutes in the present invention. In the case when the FR value is below 20 or exceeds 100, printing property cannot be improved.

In the polyacetal resin, there can be preferably mixed a hindered amine compound together with the fatty acid esters composition of a polyglycerine.

Hindered amine compound specifically includes 4-acetoxy-2,2,6,6-tetramethylpiperidine, 4-stearoiloxy-2,2,6,6-tetramethylpiperidine, 4-acryloiloxy-2,2,6,6-tetramethyl piperidine, 4-(phenylacetoxy)-2,2,6,6-tetramethylpiperidine, 4-benzoiloxy-2,2,6,6-tetramethylpiperidine, 4-methoxy-2,2,6,6-tetramethylpiperidine, 4-stearyloxy-2,2,6,6-tetramethyl piperidine, 4-cyclohexyloxy-2,2,6,6-tetramethylpiperidine, 4-benzyloxy-2,2,6,6-tetramethylpiperidine, 4-phenoxy-2,2,6,6-tetramethylpiperidine, 4-ethylcarbamoyloxy-2,2,6,6-tetramethyl piperidine, 4-phenylcarbamoyloxy-2,2,6,6-tetramethylpiperidine, bis(2,2,6,6-tetramethyl-4-piperidyl)-carbonate, bis(2,2,6,6-tetramethyl-4-piperidyl)-oxalate, bis(2,2,6,6-tetramethyl-4-piperidyl)-malonate, bis(2,2,6,6-tetramethyl-4-piperidyl)-adipate, bis(2,2,6,6-tetramethyl-4-piperidyl)-terephthalate, bis(2,2,6,6-tetramethyl-4-piperidyl)-ethane, '-bis(2,2,6,6-tetramethyl-4-piperidyl)-xylene, bis(2,2,6,6-tetramethyl-4-piperidyl)-tollylene-2,4-dicarbamate, bis(2,2,6,6-tetramethyl-4-piperidyl)-hexamethylene-1,6-dicarbamate, tris(2,2,6,6-tetramethyl-4-piperidyl)-benzene-1,3,5-tricarboxylate, and tris(2,2,6,6-tetramethyl-4-piperidyl)-benzene-1,3,4-tricarboxylate, etc.

Furthermore, in the polyacetal resin, there can be preferably mixed an additive such as beta-alanine polymer, a polyamide such as 6,6-nylon, 6,10-nylon, thermal stabilizers such as melamine, anti-oxidants such as 2,2'-methylenebis (4-methyl-6-t-butylphenol), triethyleneglycol-bis[3-(3-t-butyl-5-methyl-4-hydroxyphenyl)propionate], pentaerythritol-tetrakis[3-(3,5-di-t-butyl-4-hydroxyphenyl) propionate], slipping agents, reinforcing materials such as glass fibers, carbon fibers, inorganic fillers such as potassium titanate fibers, fibrous titanium oxides, glass beads, talc, calcium carbonate, releasing agents, plasticizers, carbon black, and pigments, etc., together with the fatty acid esters composition of a polyglycerine.

In order to promote a printing ability of a resin composition in which the polyacetal resin are mixed with the fatty acid esters composition of a polyglycerine of the first aspect or the highly purified fatty acid esters composition of a polyglycerine of the fourth aspect, a hindered amine compound, and other additives, the thickness of skin layer in a molded article is preferably controlled within 15 microns.

The skin layer in the molded article means an outer surface layer at side portion in a sliced sample through which light is not polarized when observed by a light-transmittable type polarizing microscope of 340-magnifications using a cross nicol.

The sliced sample is prepared by slicing cross section of a molded article in the thickness of 10 microns with a microtome.

The thickness of the skin layer can be adjusted by controlling crystallization time of resin or selecting an appropriate molding method, or the combination thereof.

As the method for controlling crystallization time of resin, there is a method in which crystallization time of molded articles is controlled in a range of 20 to 100 seconds.

Crystallization time in the present invention means a time of period (second) until an exothermal peak accompanied by crystallization of polyacetal resin is detected after temperature of a sample holder attained to 150° C. as described below.

The temperature of 5 mg of the polyacetal resin is heated to 200° C. at the rate of 320° C./minute, and maintained at 200° C. for 2 minutes, followed by cooling until 150° C. at the rate of 80° C./minute.

As the method for controlling crystallization time in a range of 20 to 100 seconds, there is a method in which there are mixed an appropriate amount of a nucleating agent such as talc, silicate powder, hydrotalcite, calcium carbide, amine-based compound such as melamine or dicyandiamide, nitrides such as boron nitride, zinc oxide, titanium oxide, calcium oxide, magnesium oxide, carbon black such as conducting carbon black, and an organic nucleating agent such as a branched polyacetal copolymer, polyamides such as 6,6-nylon, an ionic polymer of acrylamide, and powder of vinyl polymers, etc.

Of those, there are preferably employed nitrides such as boron nitride, and polyamides such as 6,6-nylon or an ionic polymer of acrylamide, and most preferably boron nitride.

There is preferably employed a boron nitride having an averaged particle size of from 1 to 10 microns, preferably from 2 to 7microns.

Subsequently, there is described a method for controlling the thickness of the skin layer by selecting an appropriate molding method.

The process includes (1) a method in which molding is carried out at mold temperatures ranging from 100 to 150° C., preferably from 110 to 140° C., (2) a method in which injection molding is carried out be selectively heating cavities in a mold for injection molding with an induction heating method by microwave, (3) a method in which an article is compressively molded with a thermal roll, and then gradually cooled, and (4) a method in which an article is molded at the mold temperature ranging from 10 to 100° C., and then molded article is thermally annealed at the temperature ranging from 150° C. to a melting point of a polyacetal resin.

Of those, the methods (1) and (2) are preferably employed from viewpoint of productivity.

Polyacetal resin composition in which a polyacetal resin is mixed with the fatty acid esters composition of a polyglycerine of the first aspect or the highly purified fatty acid esters composition of a polyglycerine of the fourth aspect in the present invention and other additives is preferably used as a lever, an instrumental panel, a dial plate for a taping writer, a knob for a combination switch, housings, and a shutter for a disk or a magnetic tape cartridge. More preferably, it is employed as a shutter for a disk or a magnetic tape cartridge.

Furthermore, polyacetal resin composition in which a polyacetal resin is mixed with the fatty acid esters composition of a polyglycerine of the first aspect or the highly purified fatty acid esters composition of a polyglycerine of the fourth aspect in the present invention in order to improve wetting property is preferably employed as an ink jet nozzle in a printer for a personal computer.

In order to prepare another polyacetal resin composition, in the case when the fatty acid esters composition of a polyglycerine of the first aspect or the highly purified fatty acid esters composition of a polyglycerine of the fourth aspect is mixed together with a hindered phenol-based compound, fibrous titanium oxide, and at least one selected from the group consisting of a compound having nitrogen, a hydroxide of alkaline metal or alkaline earth metal, a metal salt of a carboxylic acid or an inorganic acid, and a polyacetal resin, it acts as a releasing agent from a molding die or an agent for improving fluidity in a molding die.

The above-described polyacetal resin composition is preferably employed as small or precise parts having thin thickness for precision instruments such as a watch, a printer, and a desk-top electronic calculator, etc., because of being excellent in mechanical properties and dimensional stability.

In the above-described polyacetal resin composition for precision instruments, although the polyacetal resin is not limited regardless of homopolymers or copolymers described hereinabove and polymerization degree thereof, there is preferably employed a polyacetal resin having an FR value (ASTM D1238-57E) of more than 7 g/10 minutes.

The surface of the fibrous titanium oxide is preferably processed. Unprocessed fibrous titanium oxide causes decomposition and foaming in the resin composition during compounding and/or molding.

The fibrous titanium oxide has preferably an aspect ratio of more than 10. In the case when the ratio is below 10, as reinforcing effect is not shown, Average diameter of the fibrous titanium oxide preferably ranges from 0.02 to 0.6 microns, and average length of the fibrous titanium oxide preferably ranges from 1 to 20 microns, The fibrous titanium oxide is preferably employed in an amount ranging from 1 to 70 parts by weight, preferably from 10 to 50, more preferably from 20 to 40 based on 100 parts by weight of the acetal resin.

In the case when the ratio is below 1, an reinforcing effect is not shown, and in the case when the ratio exceeds 70, fluidity is not only remarkably lowers but also thermal stability of the resin composition unpreferably decreases.

As agents for processing the surface of the fibrous titanium oxide, there can be limitlessly employed silan-based coupling agents, titanate-based coupling agents, aluminum-based coupling agents, and zirconate-based coupling agents which have been conventionally employed.

Specifically, there are exemplified N-(2-aminoethyl)-3-aminopropyl trimethoxysilane,3-glycidoxypropyl trimethoxysilane, isopropyl tristearoyl titanante, dilsopropoxy aluminumethylacetate, and n-butylzirconate, etc.

Furthermore, granulated fibrous titanium oxides are particularly preferably employed because of more excellent workability in a mixing process compared to no-granulated fibrous titanium oxides. However, fibrous titanium oxides which are too strongly granulated are not preferred because of not being sufficiently loosened, unpreferably resulting in insufficient dispersion of the fibrous titanium oxides and decrease of mechanical properties in a molded article.

As the compound having nitrogen, there are specifically exemplified polyamide polymers or copolymers such as nylon 12, nylon 610, nylon 6, and nylon 66, polyamides having substituent groups such as methylol group, nylon salts, polyamides such as polyester amides which are prepared from caprolactones and caprolactams, polyaminotriasol, dihydrazide dicarboxylate such as hydrazide oxalate, hydrazide adipate, and hydrazide sebacate, a condensate thermally prepared from urea, a condensed polymer having nitrogen prepared from urea and diamines, uracyls, cyanoguanidines, dicyandiamide, guanamine(2,4-diamino-sym-troadine), melamine(2,4,6-triamino-sym-triadine), N-butylmelamine, N-phenylmelamine, N,N-diphenylmelamine, N,N-diallylmelamine, N,N',N"-triallylmelamine, N,N',N"-trimethylolmelamine, benzoguanamine(2,4-diamino-6-phenyl-sym-triadine), 2,4-diamino-6-methyl-sym-triadine, 2,4-diamino-6-butyl-sym-triadine, 2,4-diamino-6-benzyloxy-sym-triadine, 2,4-diamino-6-butoxy-sym-triadine, 2,4-diamino-6-cyclohexyl-sym-triadine, 2,4-diamino-6-chloro-sym-triadine, 2,4-diamino-6-mercapto-sym-triadine, 2,4,-dioxy-6-amino-sym-triadine, 2-oxy-4,6-diamino-sym-triadine, 2,4-diamino-6-methyl-sym-triadine, N,N',N',N'-tetracyanoethylbenzguanamine, and a melamine-formaldehyde condensate, etc.

Of those, there are preferably employed a melamine, a melamine derivative, and a melamine-formaldehyde condensate, etc.

As the hydroxide of alkaline metal or alkaline earth metal, the metal salt of a carboxylic acid or an inorganic acid, there are specifically exemplified alkali metallic salts such as lithium salts, sodium salts, and potassium salts, alkali earth metallic salts such as magnesium salts, calcium salts, and barium salts, inorganic acid salts such as carbonates, phosphates, and silicates. As the carboxylic acids, there are specifically exemplified oxalic acid, malonic acid, succinic acid, and higher fatty acids having a carbon number ranging from 12 to 32 such as stearic acid and behenic acid, and higher fatty acids having substituted group such as hydroxyl group.

Of those, there are preferably employed the hydroxide of lithium, magnesium, and calcium, carbonates, and more preferably carboxylates.

As particularly preferred carboxylates containing metals, there are exemplified calcium stearate, calcium 12-hydroxystearate, and calcium behenate.

The compound having nitrogen, the hydroxide of alkaline metal or alkaline earth metal, and the metal salt of carboxylic acid or inorganic acid may be employed solely or in combination.

Those are employed in an amount ranging from 0.01 to 5 parts by weight, preferably from 0.03 to 2 parts by weight, and more preferably from 0.05 to 1 part by weight based on 100 parts by weight of the polyacetal resin.

In the case when the amount is below 0.01 part by weight, a releasing effect from a molding die, an effect for improving fluidity in the molding die, and thermal stability of molded articles become insufficient and, on the contrary, in the case when the amount exceeds 5 parts by weight, those move to the surface of molded articles, unpreferably resulting in that the surface of the molding die or molded articles become dirty by excessive amounts of those, and commercial values remarkably decrease by coloration of the molded article.

Furthermore, hindered phenol-based compounds can be mixed together with the above-described compound having nitrogen, hydroxide of alkaline metal or alkaline earth metal, and metal salt of carboxylic acid or inorganic acid in order to control thermal decomposition of polyacetal resins.

As the hindered phenol-based compounds, there are specifically exemplified 2,2-methylenebis(4-methyl-6-butyl phenol), 1,6-hexanediolbis[3-(3,5-di-t-butyl-4-hydroxyphenyl)propionate], pentaerythrityltetrakis[3-(3,5-di-t-butyl-4-hydroxyphenyl)propionate], triethyleneglycol-bis[3-(3-t-butyl-5-methyl-4-hydroxyphenyl)propionate], 1,3,5-trimethyl-2,4,6,-tris(3,5-di-t-butyl-4-hydroxy-benzyl)benzene, n-octadecyl-3-(4'-hydroxy-3',5,-di-t-butylphenol)pripionate, 4,4'-butylidene-bis-(6-t-butyl-3-methyl-phenol), distearyl-3,5-di-t-butyl-4-hydroxybenzyl phosphonate, 2-t-butyl-6-(3-t-butyl-5-methyl-2-hydroxybenzyl)-4-methylphenylacrylate, and N,N'-hexamethylenebis(3,5-di-t-butyl-4-hydroxy-hydroynamide).

Those may be employed solely or in combination.

Of those, there are particularly preferred 1,6-hexanediol bis[3-(3,5-di-t-butyl-4-hydroxyphenyl)propionate], pentaerythrityltetrakis[3-(3,5-di-t-butyl-4-hydroxyphenyl)propionate], triethyleneglycol-bis[3-(3-t-butyl-5-methyl-4-hydroxyphenyl)propionate],N,N'-hexamethylenebis(3,5-di-t-butyl-4-hydroxy-hydroynamide).

The hindered phenol-based compounds are employed in an amount ranging from 0.01 to 5 parts by weight, and preferably from 0.1 to 3 parts by weight based on 100 parts by weight of the polyacetal resin.

In the case when the amount is below 0.01 part by weight, thermal stability of molded articles become insufficient and, on the contrary, in the case when the amount exceeds 5 parts by weight, those move to the surface of molded articles, unpreferably resulting in that the molded articles become dirty by excessive amounts of those.

In the case when the fatty acid esters composition of a polyglycerine of the first aspect or fourth aspect is employed as an agent for improving a releasing property from a molding die or an agent for improving fluidity in the molding die, it is employed in an amount ranging from 0.01 to 5 parts by weight, and preferably from 0.1 to 2 parts by weight based on 100 parts by weight of the polyacetal resins.

In the case when the amount is below 0.01 part by weight, an effect for improving the releasing property or fluidity is small and, on the contrary, in the case when the amount exceeds 5 parts by weight, bleeding in the surface of the molded articles is unpreferably caused.

The above-described polyacetal resin composition is preferably employed as small or precise parts having thin thickness for precision instruments such as a watch, a printer, and a desk top electronic calculator, etc., because of being excellent in mechanical properties, thermal stability and dimensional stability.

In the meantime, the fatty acid esters compositions of a polyglycerine of the first aspect or fourth aspect in the present invention are also useful as an additive for cosmetics, toiletries, and detergents.

According to a seventh aspect of the present invention, there is provided a water-in-oil type-emulsified composition for cosmetics which comprises glycerine, oils and/or waxes, water, and a fatty acid esters composition of a polyglycerine in the first aspect or a highly-purified fatty acid esters composition of a polyglycerine in the fourth aspect.

In the water-in-oil type-emulsified composition for cosmetics, the fatty acid esters composition of a polyglycerine or the highly-purified fatty acid esters composition of a polyglycerine is employed in an amount ranging from 1.0 to 10.0% by weight, preferably from 2.0 to 5.0%, and more preferably from 3 to 4% by weight based on the total weight of the water-in-oil type-emulsified composition for cosmetics of the present invention.

In the case when it is below 1.0% by weight, stability for long time of period becomes worse and, on the contrary, in the case when it exceeds 10.0% by weight, viscosity becomes high or stability for long time of period becomes worse.

In the water-in-oil type-emulsified composition for cosmetics, there is more preferably employed the highly-purified fatty acid esters composition of a polyglycerine in the fourth aspect from viewpoint of the use for human body.

In the water-in-oil type-emulsified composition for cosmetics, glycerine is an essential component. Glycerine is employed in an amount ranging from 5 to 25% by weight, preferably from 10 to 20%, and more preferably approximately 15% by weight based on the total weight of the water-in-oil type-emulsified composition for cosmetics of the present invention.

In the case when it is below 5% by weight, stability for long time of period becomes worse and, on the contrary, in the case when it exceeds 25% by weight, a feel in use becomes worse because of strong stickiness.

In the water-in-oil type-emulsified composition for cosmetics, oils and/or waxes include hydrocarbons such as a liquid paraffin, a solid paraffin, vaseline, and a microcrystalline wax, esters such as isopropyl myristate, cetyl 2-ethylhexanate, cetyl palmitate, myristyl myristate, propyleneglycol dicaprylate, and tri(caprylic acid and capric acid) glyceryl, animal or vegetable oils/waxes such as beeswaxes, whale-waxes, lanolin, olive oils, etc. Of those, liquid paraffin and vaseline are employed in a relatively larger amount.

The oils and/or waxes are employed in an amount ranging from 10 to 40% by weight, preferably from 15 to 30%, and more preferably 20 to 25% by weight based on the total weight of the water-in-oil type-emulsified composition for cosmetics of the present invention.

In the case when it is below 10% by weight, viscosity becomes too high, resulting in that it is not thinly extended and, on the contrary, in the case when it exceeds 40% by weight, an oily feel becomes too strong and stability for a long time of period becomes deteriorated.

Water is employed in an amount ranging from 25 to 50% by weight, preferably from 30 to 40%, and more preferably 30 to 35% by weight based on the total weight of the water-in-oil type-emulsified composition for cosmetics of the present invention.

In the case when it is below 25% by weight or in the case when it exceeds 50% by weight, a good feel in use and stability for a long time of period become unpreferably deteriorated.

Furthermore, the water-in-oil type emulsified composition for cosmetics of the present invention can optionally include other surface active agents, water-soluble solvents such as propyleneglycol and ethanol, organic or inorganic fillers such as finely-sized titanium oxide, powdered nylon, talc, kaolin, ultraviolet absorbents, antiseptics, anti-oxidants, water soluble salts such as magnesium sulphate, medicinal components, coloring agent, and perfumes, etc. which are conventionally employed as additives for cosmetics.

The water-in-oil type-emulsified composition for cosmetics of the present invention can be used for cleansings, face massage, and anti-sunburn agent for human body, etc.

According to an eighth aspect of the present invention, there is provided a transparent liquid composition for cosmetics which comprises at least one of an non-ionic surface active agent, at least one of water-soluble compound having at least two hydroxyl groups, oily components, water, and fatty acid esters composition of a polyglycerine in the first aspect or a highly-purified fatty acid esters composition of a polyglycerine in the fourth aspect.

In the eighth aspect of the present invention, there is more preferably employed a highly-purified fatty acid esters composition of a polyglycerine in the fourth aspect from viewpoint of the use for human body.

As the non-ionic surface active agent, there are specifically employed a fatty acid esters composition of sorbitan, a fatty acid esters composition of glycerine, a fatty acid esters composition of polyethyleneglycol, a polyoxyethlene alkylether, a polyoxyethylene alkylphenylether, a hydrogenated castor oil of polyoxyethylene, a fatty acid esters composition of polyoxyethylene sorbitan, and a fatty acid esters composition of polyoxyethylene sorbitol, etc.

In the transparent liquid composition for cosmetics of the present invention, the fatty acid esters composition of a polyglycerine or the highly-purified fatty acid esters composition of a polyglycerine is employed in combination with at least one of the non-ionic surface active agent in an amount ranging from 5 to 40% by weight, preferably from 15 to 30%, and more preferably 15 to 20% by weight based on the total weight of the transparent liquid composition for cosmetics.

In the case when it is below 5% by weight or in the case when it exceeds 40% by weight, the liquid composition unpreferably decreases transparency, or it unpreferably gels.

HLB value ranges from 8 to 13, and preferably from 9 to 11 in a mixture composed of the fatty acid esters composition of a polyglycerine or the highly-purified fatty acid esters composition of a polyglycerine and at least one of the non-ionic surface active agent, In the case when it is below 8, or in the case when it exceeds 13, the liquid composition unpreferably decreases transparency, or it unpreferably emulsifies or gels.

In the transparent liquid composition for cosmetics of the present invention, as the water-soluble compound having at least two hydroxyl groups, there are specifically employed propylene glycol, 1,3-butanediol, dipropylene glycol, glycerine, diglycerine, polyglycerine, trimethylolpropane, erythritol, pentaerythritol, isopreneglycol, sorbitan, glucose, sorbitol, maltitol, saccharose, polyoxyethlene methylglucoside, diethyleneglycol, and polyethyleneglycol. Of those, there are preferably employed 1,3-butanediol, propylene glycol, and dipropylene glycol.

At least one of the water-soluble compound having at least two hydroxyl groups is employed in an amount ranging from 2 to 40% by weight, preferably from 4 to 25% by weight based on the total weight of the transparent liquid composition. In the case when it is below 2%, or in the case when it exceeds 25%, the liquid composition unpreferably decreases transparency, or it unpreferably emulsifies or gels.

In the transparent liquid composition for cosmetics of the present invention, the oily components include vegetable oils, mineral oils, and ester oils.

More specifically, there are employed beef tallow, squalane, olive oil, peanut oil, sweet almond oil, castor oil, corn oil, a liquid paraffin, vaseline, tri(caprylic acid and capric acid)glyceryl, isopropyl myristate, vitamin E acetate, pyridoxine dioctanoate, myristyl myristate, octyldodecanol oleate, lanolin, fatty acid derivatives of lanolin, methylpolysiloxane, and an isostearyl cholesterylester, etc.

Those may be employed solely or in combination.

The oily components are employed in an amount ranging from 3 to 70% by weight, preferably from 10 to 60%, and more preferably 15 to 30% by weight based on the total weight of the transparent liquid composition for cosmetics.

In the transparent liquid composition for cosmetics of the present invention, water is employed in an amount ranging from 0.5 to 80% by weight, and preferably from 2 to 60% by weight based on the total weight of the transparent liquid composition for cosmetics. In the case when it is below 0.5%, or in the case when it exceeds 80%, the liquid composition occasionally decreases transparency.

The transparent liquid composition for cosmetics of the present invention can be prepared by conventional mixing methods.

As a preferred preparation method, there is exemplified a method in which there are firstly mixed the fatty acid esters composition of a polyglycerine or the highly-purified fatty acid esters composition of a polyglycerine and at least one of the non-ionic surface active agent, and then the oily components are mixed, followed by gradually mixing water.

Although mixing can be carried out at room temperatures without heating, when solid components are employed, mixing may be carried out while heating.

Furthermore, the transparent liquid composition for cosmetics of the present invention can optionally include medicinal components, antiseptics, coloring agent, and perfumes, wetting agent, anti-oxidants, ultraviolet absorbents, granules such as a scrubbing material, ethanol, water-soluble or oil-soluble high molecular weight compound in order to give a viscous property to the composition, a cationic material in order to give a conditioning effect to hair, etc. which are conventionally employed as additives for cosmetics.

The transparent liquid composition for cosmetics of the present invention can be used for cleansings, an agent for massage, an agent for pack, cosmetics for hair, cosmetics for bathroom, cosmetics for keeping moisture, and a base material for a medicine, etc.

According to a ninth aspect of the present invention, there is provided a gel-like emulsified composition for cosmetics which comprises glycerine, liquid oily components, a polyvalent alcohol except glycerine, and a fatty acid esters composition of a polyglycerine in the first aspect or a highly-purified fatty acid esters composition of a polyglycerine in the fourth aspect.

In the ninth aspect of the present invention, there is more preferably employed a highly-purified fatty acid esters composition of a polyglycerine in the fourth aspect from viewpoint of the use for human body.

In the gel-like emulsified composition for cosmetics of the present invention, glycerine is an essential component. Glycerine is employed in an amount ranging from 20 to 60% by weight, preferably from 30 to 60%, and more preferably from 35 to 45% by weight based on the total weight of the gel-like emulsified composition for cosmetics of the present invention.

In the case when it is below 20%, a feel in use is deteriorated and, on the contrary, in the case when it exceeds 60%, a feel in use is deteriorated because of a warmish feel.

As the liquid oily components, there are specifically employed a hydrocarbon oil such as a liquid paraffin and squalane, an ester oil such as cetyl octanate and isopropyl myristate, and a fatty acid triglyceride such as trioctanic acid triglyceride and olive oil, etc.

Liquid oils primarily containing higher alcohols and higher fatty acids are not preferred because of instability at high temperatures.

As the polyvalent alcohol except glycerine, there are specifically employed propyleneglycol, 1,3-butylene glycol, maltitol, and sorbitol, etc. Of those, there are preferably employed propyleneglycol and 1,3-butylene glycol.

The polyvalent alcohol except glycerine are employed in an amount ranging from 0.5 to 10% by weight, and preferably from 1 to 5% by weight based on the total weight of the gel-like emulsified composition for cosmetics of the present invention.

In the gel-like emulsified composition for cosmetics, the fatty acid esters composition of a polyglycerine or the highly-purified fatty acid esters composition of polyglycerine is employed in an amount ranging from 1.0 to 6.0% by weight, preferably from 2.0 to 5.0%, and more preferably approximately 3.5% by weight based on the total weight of the gel-like emulsified composition for cosmetics of the present invention.

HLB value is preferably more than 11 in the fatty acid esters composition of a polyglycerine or the highly-purified fatty acid esters composition of a polyglycerine. Of those, there are preferably employed decaglyceryl monolaurate and hexaglyceryl monolaurate having HLB value of 11 to 15.

The gel-like emulsified composition for cosmetics of the present invention can be used for cleansings and cosmetics for massage, etc.

Furthermore, the gel-like emulsified composition for cosmetics of the present invention can optionally include ultra-violet absorbents, antiseptics, anti-oxidants, coloring agent, perfumes, and medicinal components, etc. which are conventionally employed as additives for cosmetics or toiletries.

According to a tenth aspect of the present invention, there is provided a composition for tooth paste which comprises an abrasive, a caking material, a wetting agent, and a fatty acid esters composition of a polyglycerine in the first aspect or a highly-purified fatty acid esters composition of a polyglycerine in the fourth aspect.

In the tenth aspect of the present invention, there is more preferably employed a highly-purified fatty acid esters composition of a polyglycerine in the fourth aspect from viewpoint of the use for human body.

In the composition for tooth paste, the fatty acid esters composition of a polyglycerine or the highly-purified fatty acid esters composition of a polyglycerine is employed in an amount ranging from 0.4 to 10% by weight, preferably from 1.0 to 3.0%, and more preferably approximately 2.0% by weight based on the total weight of the composition for tooth paste of the present invention. It is to be noted that the fatty acid esters composition of a polyglycerine or the highly-purified fatty acid esters composition of a polyglycerine acts as a foaming agent.

The composition for tooth paste of the present invention includes a paste, powder, ointment, and liquid type tooth polisher.

As the abrasives, there are included calcium secondary phosphate (dihydrate, anhydride), calcium carbonate, silicates, and insoluble sodium metaphosphates.

As the caking material, there are included sodium carboxy-methyl cellulose, carrageenan, sodium alginate, bentonite, and silicate anhydride, etc.

As the wetting agent, there are included glycerine, sorbitol, propyleneglycol, sodium pyrrolidone-carboxylate, and polyethyleneglycol, etc.

The composition for tooth paste of the present invention may include a variety of perfumes and medicinal components.

As the medicinal components to be employed, fluorides, glycyrrhizinate, chlorohexydine, hinokitiol, dextranase, lysozyme, edible salts, tranexamic acid, and epsilon-aminocaproic acid, etc. which are conventionally employed for a tooth paste composition.

According to an eleventh aspect of the present invention, there is provided a cleaning agent composition which comprises (a) a polycarboxylic acid ester of a monoglyceride or a salt thereof represented by general formula (3)

$$R1\text{—}COO\text{—}CH_2\text{—}CHOZ1\text{—}CH_2OZ2 \qquad (3)$$

wherein R1 is an alkyl or alkenyl group having a carbon number ranging from 7 to 17, either Z1 or Z2 is a residual group of a polycarboxylic acid or salt thereof, and another hydrogen atom or a residual group of a polycarboxylic acid or salt thereof, (b) a fatty acid esters composition of a polyglycerine in the first aspect or a highly-purified fatty acid esters composition of a polyglycerine in the fourth aspect, (c) organic or inorganic builders, (d) fluidity improvers, and additionally (e) thickening agents, (f) perfumes, (g) coloring agents, (h) sterilizers, (i) enzymes, and (j) anti-inflammatory agents.

In the cleaning agent composition, the component (b) which is the fatty acid esters composition of a polyglycerine or the highly-purified fatty acid esters composition of a polyglycerine is employed in an amount ranging from 1.0 to 10.0% by weight, preferably from 2.0 to 8.0%, and more preferably approximately 5% by weight based on the total weight of the cleaning agent composition.

In the case when the amount is below 1.0% by weight, cleaning ability becomes poor and, on the contrary, even in the case when the amount exceeds 10.0% by weight, cleaning ability does not increase.

In the cleaning agent composition, the component (a) which is the polycarboxylic acid ester of a monoglyceride or a salt thereof is represented by the general formula (3).

In the formula (3), R1 is an alkyl or alkenyl group having a carbon number ranging from 7 to 17 which may be linear or branched. Specifically there are included heptyl group, nonyl group, undecyl group, tridecyl group, pentadecyl group, heptadecyl group, heptadecenyl group, etc. Of those, nonyl group, undecyl group, and tridecyl group are preferably employed from viewpoint of cleaning ability.

Z1 or Z2 is a residual group of a polycarboxylic acid or salt thereof, and another hydrogen atom or a residual group of a polycarboxylic acid. Specifically there are preferably employed citric acid, succinic acid, maleic acid, malic acid, glutaric acid, adipic acid, tartaric acid, diacetyl tartaric acid, and the salts thereof. Of those, there are more preferably employed citric acid, succinic acid, diacetyl tartaric acid, and the salts thereof.

As the salts, there are included alkali salts such as sodium salts, potassium salts, lithium salts, alkali earth metal salts such as magnesium salts, ammonium salts, lower amine salts such as trimethylamine, triethylamine salts, lysine salts, mono-, di-, and tri-lower alkanol amine salts such as monethanol amine, diethanol amine, and triethanol amine which are substituted or non-substituted ammonium salts.

Furthermore, an acid type of the polycarboxylic acid esters of a monoglyceride or the salts thereof exhibits an effect capable of decreasing microorganisms in starting materials for processed foods. On the other hand, the salts thereof exhibits high cleaning ability. Accordingly, those are preferably employed by appropriately mixing.

Still further, the polycarboxylic acid esters of a monoglyceride or the salts may contain a position isomer in which the polycarboxylic acid connects to primary or secondary hydroxyl group in the monoglyceride and compounds in which 2 mol of the polycarboxylic acid connects to the monoglyceride. It is to be noted that the position isomer and the compounds are produced in a refining process.

In the cleaning agent composition, the components (a)/(b) are employed in a weight ratio ranging from 90/10 to 30/70, and preferably from 80/20 to 40/60.

In the case when the ratio is below 30/70 or exceeds 90/10, cleaning ability unpreferably decreases.

Furthermore, the cleaning agent composition of the present invention can optionally include other additives which are conventionally employed, as far as cleaning ability is not deteriorated.

As the other additives, there are employed a sodium phosphate of a polyoxyethylene alkylether, a fatty acid ester of sucrose, a fatty acid ester of polyoxyethylene sorbitan, a fatty acid monoethanolamide, a polyoxyethylene alkylether, a polyoxyethylene alkylphenylether, a carboxybetaine type-, a imidazolinium type-, a sulphobetain type-, and an alanine type-surface active agents which are harmless to human body.

As the other additives, there are further employed organic builders such as sodium pyrophosphate, sodium tripolyphosphate, zeolite, sodium citrate, sodium malate, nitrilotrisodium acetate, and a sodium polyacrylate, inorganic builders such as sodium carbonate, sodium sulphate, sodium chloride, magnesium sulphate, and calcium chloride, fluidity improvers such as glycerine, ethanol, propylene glycol, and polyethyleneglycol, thickening agents such as carboxymethyl cellulose and hydroxyethyl cellulose, perfumes, coloring agents, sterilizers, enzymes, and anti-inflammatory agents, etc.

According to a twelfth aspect of the present invention, there is provided a foaming composition for cleaning which comprises a mixture composed of at least one of a lower monovalent alcohol having a carbon number ranging from 1 to 3, water, at least one of a higher alcohol having a carbon number ranging from 12 to 22, and a fatty acid esters composition of a polyglycerine as set forth in claim 1 or a highly-purified fatty acid esters composition of a polyglycerine as set forth in claim 10, and an agent for foaming the mixture.

In the foaming composition for cleaning, the fatty acid esters composition of a polyglycerine or the highly-purified fatty acid esters composition of a polyglycerine is employed in an amount ranging from 0.5 to 10.0% by weight, and preferably from 1.0 to 5.0% based on the total weight of the foaming composition for cleaning.

In the case when the amount is below 0.5% by weight, foaming ability becomes poor and, on the contrary, in the case when the amount exceeds 10.0% by weight, foaming ability does not only increase but also foam is not readily broken, and a feel in use becomes worse.

As the lower monovalent alcohol having a carbon number ranging from 1 to 3, there are employed methanol, ethanol, n-propanol, and iso-propanol. Of those, ethanol modified by brucine, etc. from viewpoint of innoxious properties.

In the foaming composition for cleaning, the lower monovalent alcohol having a carbon number ranging from 1 to 3 is employed in an amount ranging from 20 to 70% by weight, and preferably from 30 to 60% by weight based on the total weight of the foaming composition for cleaning.

In the case when the amount is below 20% by weight, a refreshing feel in use becomes not only insufficient but also cleaning ability for fatty dirt on skin is insufficient and, on the contrary, in the case when the amount exceeds 70% by weight, durability of foam becomes not only worse but also a feel in use becomes unpreferably worse.

As the higher alcohol having a carbon number ranging from 12 to 22, there are employed lauryl alcohol, myristyl alcohol, palmityl alcohol, stearlyl alcohol, oleyl alcohol, cetyl alcohol, and behenyl alcohol.

The higher alcohol having a carbon number ranging from 12 to 22 is employed in an amount ranging from 0.5 to 5% by weight, and preferably from 1 to 3% by weight based on the total weight of the foaming composition for cleaning. In the case when the amount is below 0.5% by weight, foaming ability and stability of foam are insufficient and, on the contrary, in the case when the amount exceeds 5% by weight, stability of the composition and sol therefrom becomes not only worse but also a feel in use becomes unpreferably worse.

As the agent for foaming the mixture, there are employed liquified petroleum gases such as propane, n-butane, i-butane, n-pentane, i-pentane, and a mixture thereof with dimethylether.

The agent for foaming the mixture is employed in an amount ranging from 2 to 15% by weight, and preferably from 3 to 10% by weight based on the total weight of the foaming composition for cleaning. In the case when the amount is below 2% by weight, foaming ability is insufficient and, contrarily, in the case when the amount exceeds 15% by weight, quality and stability of foam become worse, and a feel in use becomes unpreferably worse.

The foaming composition for cleaning of the present invention is an aerosol type, and may be a gas/liquid two phases type or gas/liquid/liquid three phases type.

Furthermore, the foaming composition for cleaning of the present invention can optionally include polyvalent alcohols, high molecular compounds, polysaccharides, protein derivatives, extracts from plants, ultraviolet ray absorbents, medicinal components, chelating agents, antioxidants, and perfumes as far as effects are not deteriorated within an appropriate quantity and quality depending upon purposes.

As the polyvalent alcohols, there are specifically employed propylene glycol, 1,3-butyleneglycol, dipropylene glycol, glycerine, diglycerine, sorbitan, sorbitol, maltitol, glucose, sucrose, etc.

As the high molecular compounds, there are specifically employed a cationic polymer such as poly(dimethyldiallyl ammoniumhalide) [eg. Merquat 100, etc.], a copolymer of dimethyldiallyl ammoniumhalide with an acrylic monomer (eg. Merquat 550, etc.), a condensate of polyethyleneglycol/epichlorohydrin/propyleneamine [Polyquat H, etc.], a quaternary nitrogen-containing cellulose [Polymer JR, etc.], an anionic polymer such as xanthane gum, carrageenan, sodium alginate, arabic gum, pectic substances, a carboxyvinyl polymer, a nonionic polymer such as a copolymer of vinyl acetate with polyvinyl pyrrolidone, or vinyl pyrrolidone, a copolymer of vinyl pyrrolidone with a vinyl acetate and an acrylicaminoacrylate, hydroxyethylcellulose, hydroxypropylcellulose, hydroxypropyl ethylcellulose, methylcellulose, dextrins, galactan, pullulan, amphoretic polyelectrolytes such as Yukafoamer AM-75 in which there are copolymerized dialkylaminoethylacrylate, dialkylamino-ethylmethacrylate, and diacetone acrylamide with alkylacrylates or alkylmethacrylates, and then modified by acetic halides.

As the polysaccharides, there are specifically employed hyaluronic acid, chondroitin, heparan sulphate, and salts thereof.

As the ultraviolet ray absorbents, there are specifically employed paraaminobenzoic acid, glycerylparaaminobenzoic acid, ethyldihydroxypropylparaaminobenzoic acid, etc.

As the medicinal components there are specifically employed vitamin C, vitamin Es, amino acids, anti-inflammatory agent, and sterilizers, etc.

The present invention is illustrated below by Examples and Comparative Examples.

EXAMPLE 1

Preparation No. 1 of a Fatty Acid Esters Composition of Polyglycerine Containing More than 70% of a Fatty Acid Monoester A four-necked reaction vessel equipped with a tube for supplying nitrogen gas, a stirrer, a cooler, a thermostat, and a dropwise funnel was charged with 100.16 parts by weight of lauric acid and 0.0622 part by weight of phosphoric acid (a purity of 85%), followed by heating to 140° C. Subsequently, 222.24 parts by weight (molar ratio of glycidol/lauric acid=6) of glycidol was added drowpwise over 5 hours to allow to react until oxirane oxygen concentration in the reactant attains below 0.1% while maintaining the reaction temperature at 140° C.

After cooling, the reactant was taken out to obtain approximately 300 parts by weight of a lauric acid esters composition of a polyglycerine. The lauric acid esters composition of a polyglycerine prepared was analyzed by the HPLC analytical condition No. 1 as defined hereinabove.

The lauric acid esters composition of a polyglycerine (hereinafter, referred to as PGMLEC) prepared was dissolved in water to prepare an aqueous solution of 10%, followed by vibrating with hands for 30 seconds to visually observe foaming ability and appearance.

FIG. 1 is a chart obtained by the HPLC analysis relating to the PGMLEC prepared. It was identified from the chart that the composition (a hexaglycerine monolaurate composition) contains a monolaurate of polyglycerine of 87.7% analyzed by the condition No. 1 in the HPLC analysis method.

EXAMPLE 2

Preparation No. 2 of a Fatty Acid Esters Composition of a Polyglycerine Containing More than 70% of a Fatty Acid Monoester A four-necked flask equipped with a tube for supplying nitrogen gas, a stirrer, a cooler, a thermostat, and a dropwise funnel was charged with 100.16 parts by weight of lauric acid and 0.0810 part by weight of phosphoric acid (85%), followed by heating to 140° C.

Subsequently, 222.24 parts by weight (molar ratio of glycidol/lauric acid=6) of glycidol was added drowpwise over 5 hours to allow to react until oxirane oxygen concentration in the reactant attains below 0.1% while maintaining the reaction temperature at 140° C. After cooling, the reactant was taken out to obtain approximately 300 parts by weight of a lauric acid esters composition of a polyglycerine. The lauric acid esters composition of a polyglycerine prepared was analyzed by the HPLC analytical conditions described hereinabove.

The lauric acid esters composition of a polyglycerine (PGMLEC) prepared was dissolved in water to prepare an aqueous solution of 10%, followed by vibrating with hands for 30 seconds to visually observe foaming ability and appearance.

Figure 2:
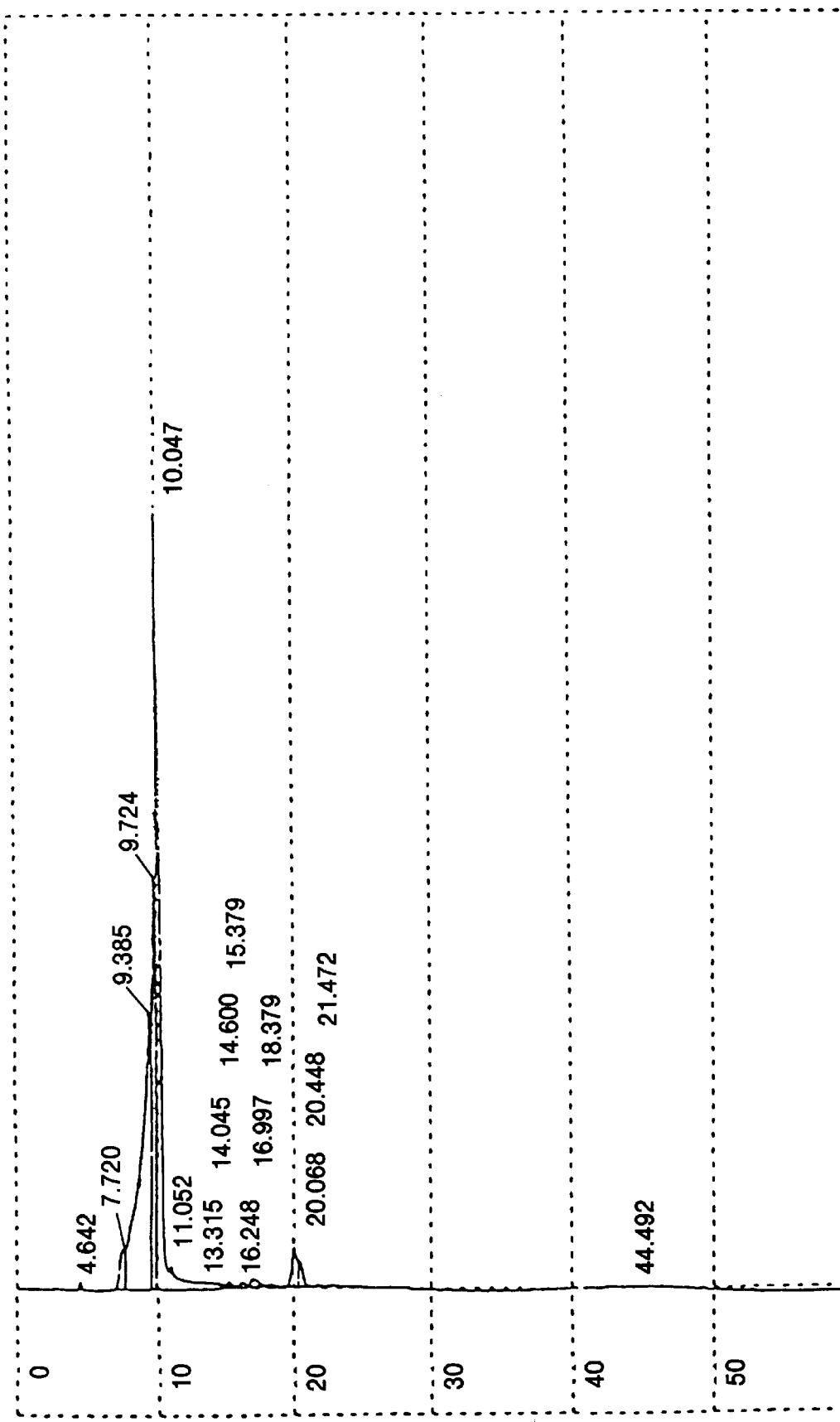
FIG. 2 is a chart obtained by HPLC relating to a lauric acid esters composition of a polyglycerine obtained in Example 2.

FIG. 2 is a chart obtained by the HPLC analysis relating to PGMLEC prepared. It was identified from the chart that the composition (a hexaglycerine monolaurate composition) contains a monolaurate of polyglycerine of 90.8% analyzed by the condition No. 1 in HPLC analysis method.

EXAMPLE 3

Preparation No. 3 of a Fatty Acid Esters Composition of a Polyglycerine Containing More than 70% of a Fatty Acid Monoester A four-necked flask equipped with a tube for supplying nitrogen gas, a stirrer, a cooler, a thermostat, and a dropwise funnel was charged with 100.16 parts by weight of lauric acid and 0.0622 part by weight of phosphoric acid (85%), followed by heating to 140° C.

Subsequently, 296.32 parts by weight (molar ratio of glycidol/lauric acid=8) of glycidol was added drowpwise over 5 hours to allow to react until oxirane oxygen concentration in the reactant attains below 0.1% while maintaining the reaction temperature at 140° C. After cooling, the reactant was taken out to obtain approximately 400 parts by weight of a lauric acid esters composition of a polyglycerine. The lauric acid esters composition of a polyglycerine prepared was analyzed by the HPLC analytical condition No. 1 as described hereinabove.

The lauric acid esters composition of a polyglycerine (PGMLEC) prepared was dissolved in water to prepare an aqueous solution of 10%, followed by vibrating with hands for 30 seconds to visually observe foaming ability and appearance.

Figure 3:
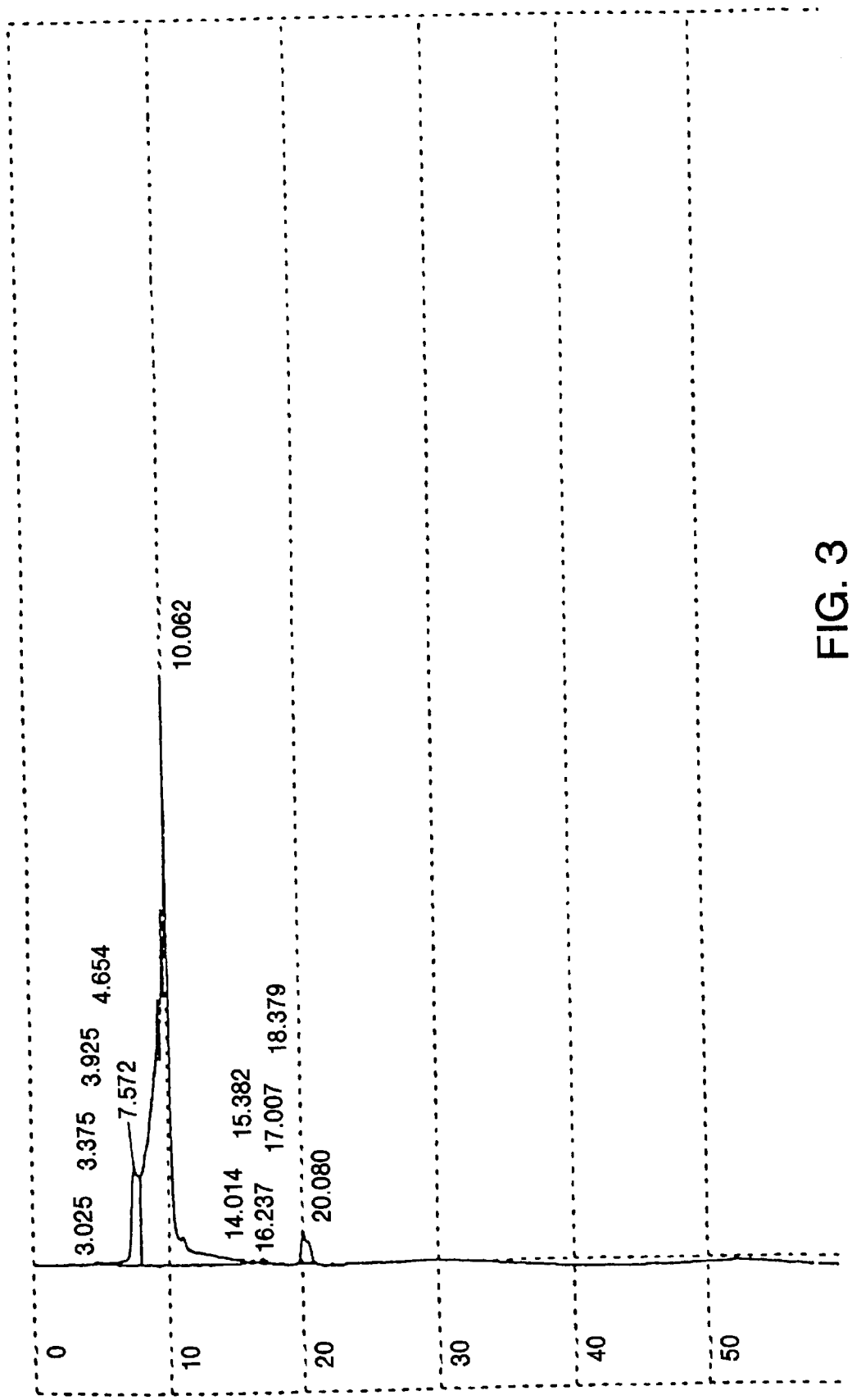
FIG. 3 is a chart obtained by HPLC relating to a lauric acid esters composition of a polyglycerine obtained in Example 3.

FIG. 3 is a chart obtained by HPLC relating to PGMLEC prepared. It was identified from the chart that the composition (an octaglycerine monolaurate composition) contains a monolaurate of polyglycerine of 84.5% analyzed by the condition No. 1 in HPLC analysis method.

EXAMPLE 4

Preparation No. 4 of a Fatty Acid Esters Composition of a Polyglycerine Containing More than 70% of a Fatty Acid Monoester A four-necked flask equipped with a tube for supplying nitrogen gas, a stirrer, a cooler, a thermostat, and a dropwise funnel was charged with 100.16 parts by weight of lauric acid and 0.118 part by weight of phosphoric acid (85%), followed by heating to 140° C.

Subsequently, 370.40 parts by weight (molar ratio of glycidol/lauric acid=10) of glycidol was added drowpwise over 5 hours to allow to react until oxirane oxygen concentration in the reactant attains below 0.1% while maintaining the reaction temperature at 140° C. After cooling, the reactant was taken out to obtain approximately 470 parts by weight of a lauric acid esters composition of a polyglycerine. The lauric acid esters composition of a polyglycerine prepared was analyzed by the HPLC analytical conditions described hereinabove.

The lauric acid esters composition of a polyglycerine (PGMLEC) prepared was dissolved in water to prepare an aqueous solution of 10%, followed by vibrating with hands for 30 seconds to visually observe foaming ability and appearance.

Figure 4:
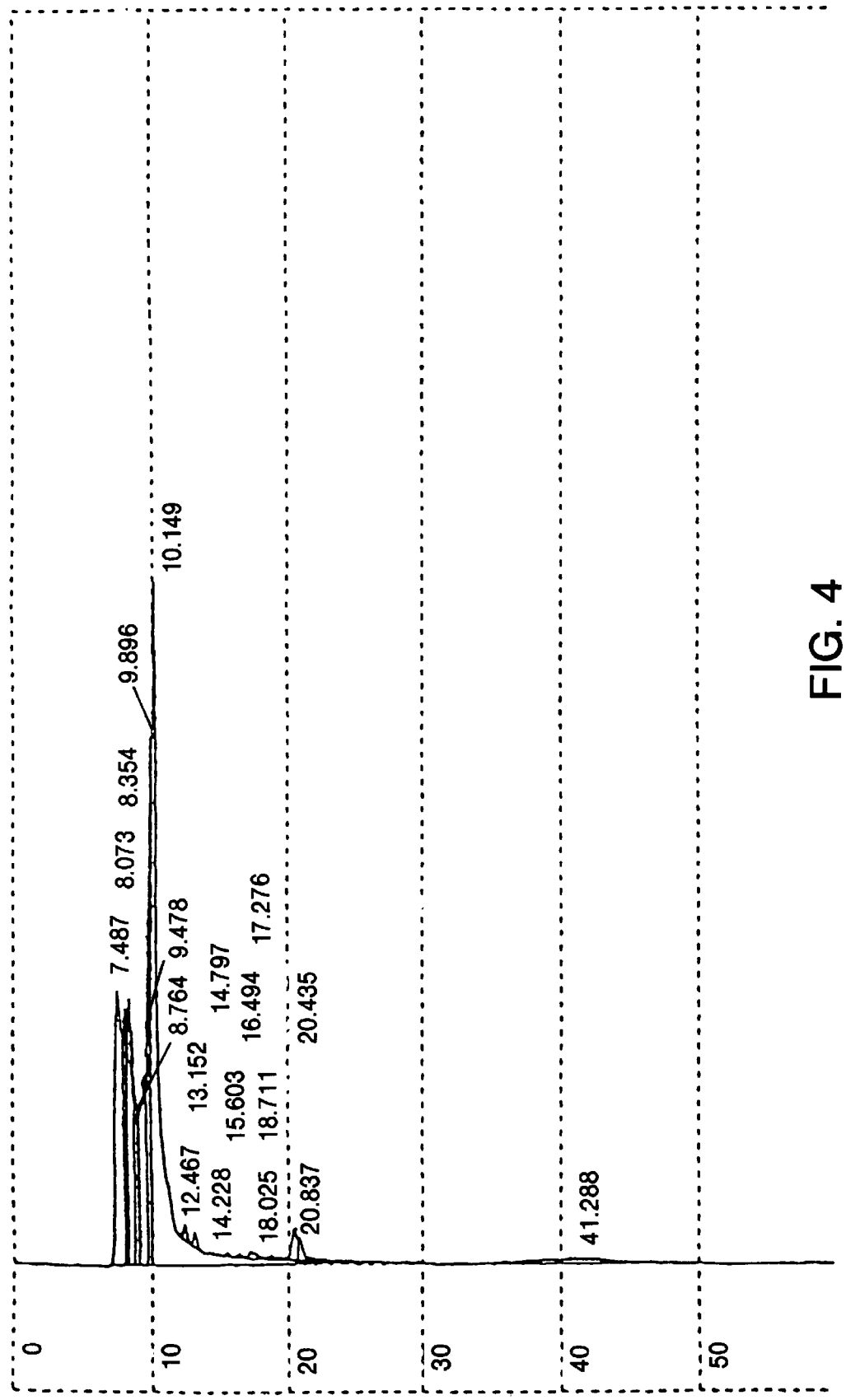
FIG. 4 is a chart obtained by HPLC relating to a lauric acid esters composition of a polyglycerine obtained in Example 4.

FIG. 4 is a chart obtained by the HPLC analysis relating to the PGMLEC prepared. It was identified from the chart that the composition (a decaglycerine monolaurate composition) contains a monolaurate of polyglycerine of 77.2% analyzed by the condition No. 1 in the HPLC analysis method.

EXAMPLE 5

Preparation No. 5 of a Fatty Acid Esters Composition of a Polyglycerine Containing More than 70% of a Fatty Acid Monoester A four-necked flask equipped with a tube for supplying nitrogen gas, a stirrer, a cooler, a thermostat, and a dropwise funnel was charged with 100.16 parts by weight of lauric acid and 0.105 part of a mixture composed of monoethyl acid phosphate and diethyl acid phosphate (EAP manufactured by Nihon Kagaku Kogyo, Ltd.), followed by heating to 140° C.

A subsequently, 370.04 parts by weight (molar ratio of glycidol/lauric acid=10) of glycidol was added drowpwise over 5 hours to allow to react until oxirane oxygen concentration in the reactant attains below 0.1% while maintaining the reaction temperature at 140° C. After cooling, the reactant was taken out to obtain approximately 470 parts by weight of a lauric acid esters composition of a polyglycerine. The lauric acid esters composition of a polyglycerine prepared was analyzed by the HPLC analytical condition No. 1 as described hereinabove.

The lauric acid esters composition of a polyglycerine (PGMLEC) prepared was dissolved in water to prepare an aqueous solution of 10%, followed by vibrating with hands for 30 seconds to visually observe foaming ability and appearance.

Figure 5:
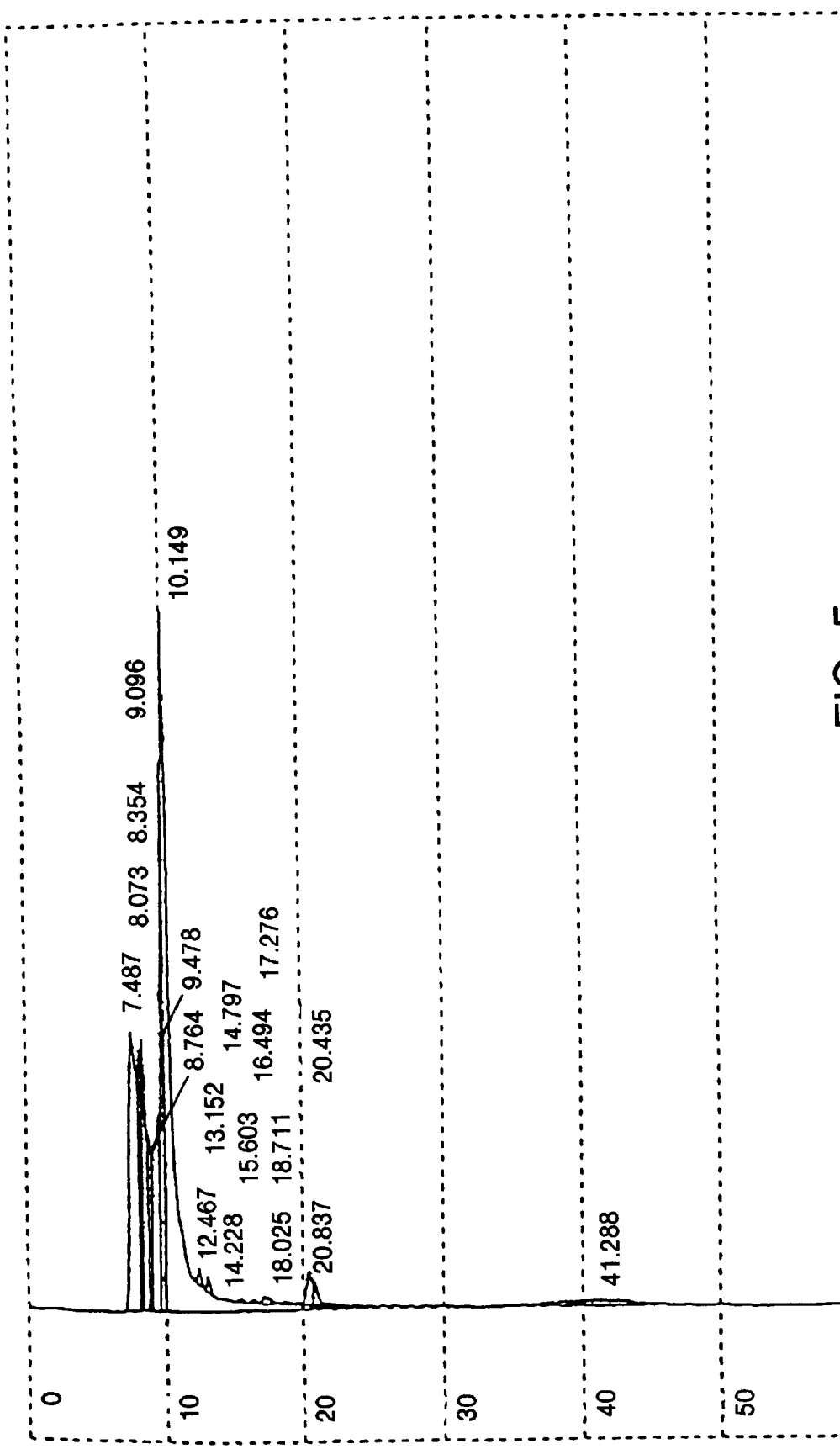
FIG. 5 is a chart obtained by HPLC relating to a lauric acid esters composition of a polyglycerine obtained in Example 5.

FIG. 5 is a chart obtained by the HPLC analysis relating to the PGMLEC prepared. It was identified from the chart that the composition (a decaglycerine monolaurate composition) contains a monolaurate of polyglycerine of 77.2% analyzed by the condition No. 1 in HPLC analysis method.

COMPARATIVE EXAMPLE 1

Preparation in the Absence of Catalysts

A four-necked flask equipped with a tube for supplying nitrogen gas, a stirrer, a cooler, a thermostat, and a dropwise funnel was charge with 100.16 parts by weight of lauric acid, followed by heating to 140° C.

Subsequently, 222.24 parts by weight (molar ratio of glycidol/lauric acid=6) of glycidol was added drowpwise over 5 hours to allow to react until oxirane oxygen concentration in the reactant attains below 0.1% while maintaining the reaction temperature at 140° C. After cooling, the reactant was taken out to obtain approximately 300 parts by weight of a lauric acid esters composition of a polyglycerine. The lauric acid esters composition of a polyglycerine prepared was analyzed by the HPLC analytical condition No. 1 as described hereinabove.

The lauric acid esters composition of a polyglycerine (PGMLEC) prepared was dissolved in water to prepare an aqueous solution of 10%, followed by vibrating with hands for 30 seconds to visually observe foaming ability and appearance.

Figure 6:
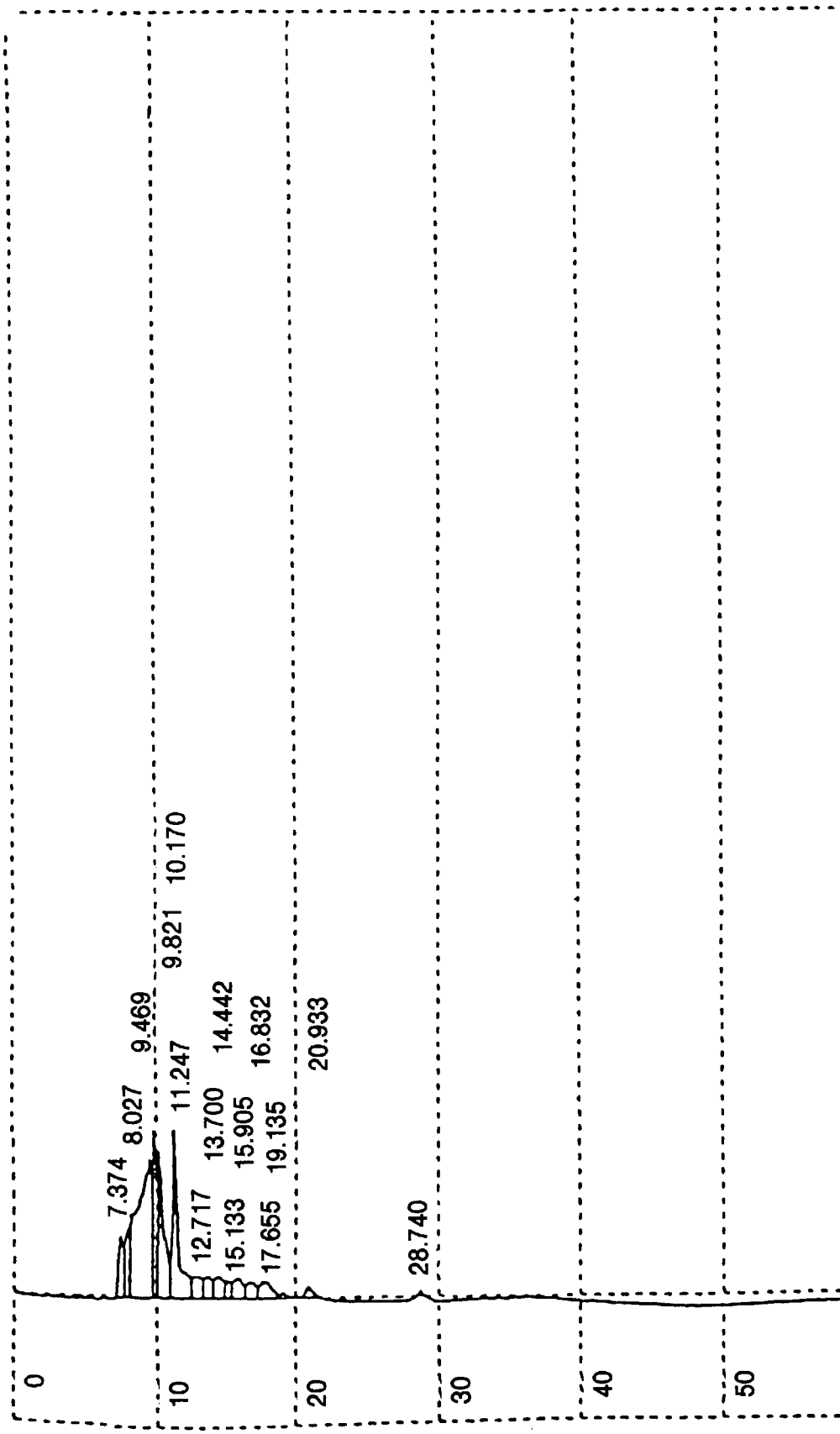
FIG. 6 is a chart obtained by HPLC relating to a lauric acid esters composition of a polyglycerine obtained in Comparative Example 1.

FIG. 6 is a chart obtained by the HPLC analysis relating to the PGMLEC (a hexaglycerine monolaurate composition) prepared.

COMPARATIVE EXAMPLE 2

Preparation in the Presence of Paratoluene Sulfonic Acid

A four-necked flask equipped with a tube for supplying nitrogen gas, a stirrer, a cooler, a thermostat, and a dropwise funnel was charged with 100.16 parts by weight of lauric acid and 0.371 part by weight of paratoluene sulfonic acid as a catalyst, followed by heating to 140° C. Subsequently, 222.24 parts by weight (molar ratio of glycidol/lauric acid= 6) of glycidol was added drowpwise over 5 hours to allow to react until oxirane oxygen concentration in the reactant attains below 0.1% while maintaining the reaction temperature at 140° C. After cooling, the reactant was taken out to obtain approximately 300 parts by weight of a lauric acid esters composition of a polyglycerine.

The lauric acid esters composition of a polyglycerine prepared was analyzed by the HPLC analytical conditions described hereinabove. The lauric acid esters composition of a polyglycerine (PGMLEC) prepared was dissolved in water to prepare an aqueous solution of 10%, followed by vibrating with hands for 30 seconds to visually observe foaming ability and appearance.

Figure 7:
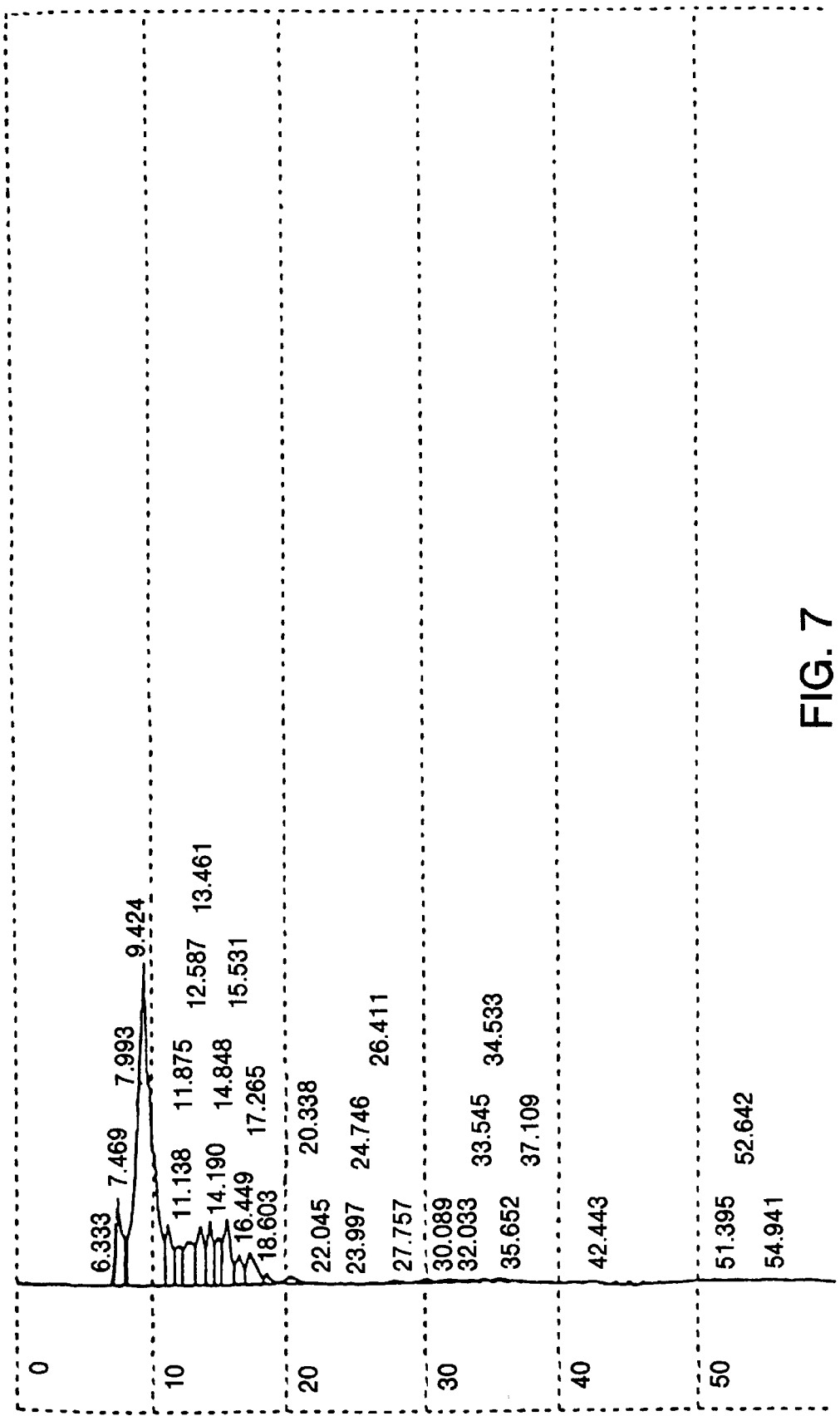
FIG. 7 is a chart obtained by HPLC relating to a lauric acid esters composition of a polyglycerine obtained in Comparative Example 2.

FIG. 7 is a chart obtained by the HPLC analysis relating to the PGMLEC (a hexaglycerine monolaurate composition) prepared.

COMPARATIVE EXAMPLE 3

Preparation by the Reaction of a Fatty Acid Monoglyceride with Glycidol

A four-necked flask equipped with a tube for supplying nitrogen gas, a stirrer, a cooler, a thermostat, and a dropwise funnel was charge with 137 parts by weight monoglyceride of lauric acid and 0.45 part by weight of sodium methylate (methanol solution having 28%) as a catalyst, followed by heating to 90° C.

Subsequently, 185.2 parts by weight (molar ratio of glycidol/monoglyceride of lauric acid=5) of glycidol was added drowpwise over 5 hours to allow to react until oxirane oxygen concentration in the reactant attains below 0.1% while maintaining the reaction temperature at 140° C. After cooling, the reactant was taken out to obtain approximately 300 parts by weight of a lauric acid esters composition of a polyglycerine The lauric acid esters composition of a polyglycerine prepared was analyzed by the HPLC analytical condition No. 1 as described hereinabove.

The lauric acid esters composition of a polyglycerine (PGMLEC) prepared was dissolved in water to prepare an aqueous solution of 10%, followed by vibrating with hands for 30 seconds to visually observe foaming ability and appearance.

Figure 8:
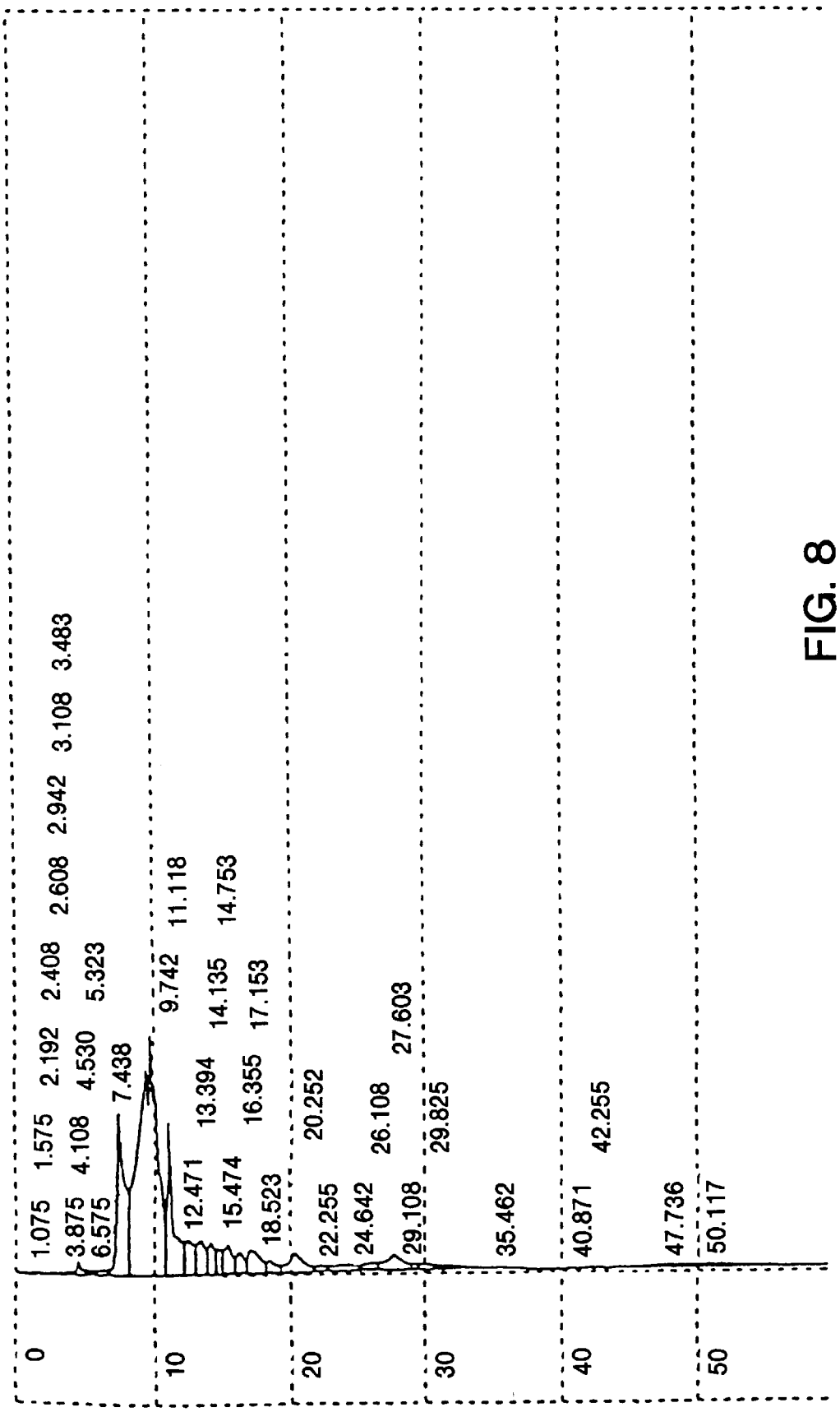
FIG. 8 is a chart obtained by HPLC relating to a lauric acid esters composition of a polyglycerine obtained in Comparative Example 3.

FIG. 8 is a chart obtained by the HPLC analysis relating to the PGMLEC prepared.

COMPARATIVE EXAMPLE 4

Preparation by the Reaction of a Fatty Acid with Polyglycerine

A four-necked flask equipped with a tube for supplying nitrogen gas, a stirrer, a cooler, a thermostat, and a dropwise funnel was charged with 175.3 parts by weight a polyglycerine having a hydroxyl value of 960 (PGL06/a hexaglycerine manufactured by Daicel Chemical Industries, Ltd., followed by heating to 80° C. Subsequently, 100.16 parts by weight (molar ratio of polyglycerine/lauric acid=1) of lauric acid was dissolved while maintaining at 80° C.

Subsequently, 0.75 part by weight of sodium carbonate and 0.25 part by weight of sodium hydrosulphite were added to allow to react by esterification at 210° C. After two hours, acid value was changed to 0.89, followed by taking out a reaction product after cooling at 100° C.

The lauric acid esters composition of a polyglycerine prepared was analyzed by the HPLC analytical conditions described hereinabove, it was identified from the chart that the lauric acid esters composition of a polyglycerine prepared (a hexa glycerine monolaurate composition) contains a monolaurate of polyglycerine of 55.1%.

The composition was dissolved in water to prepare an aqueous solution of 10%, followed by vibrating with hands for 30 seconds to visually observe foaming ability and appearance.

Figure 9:
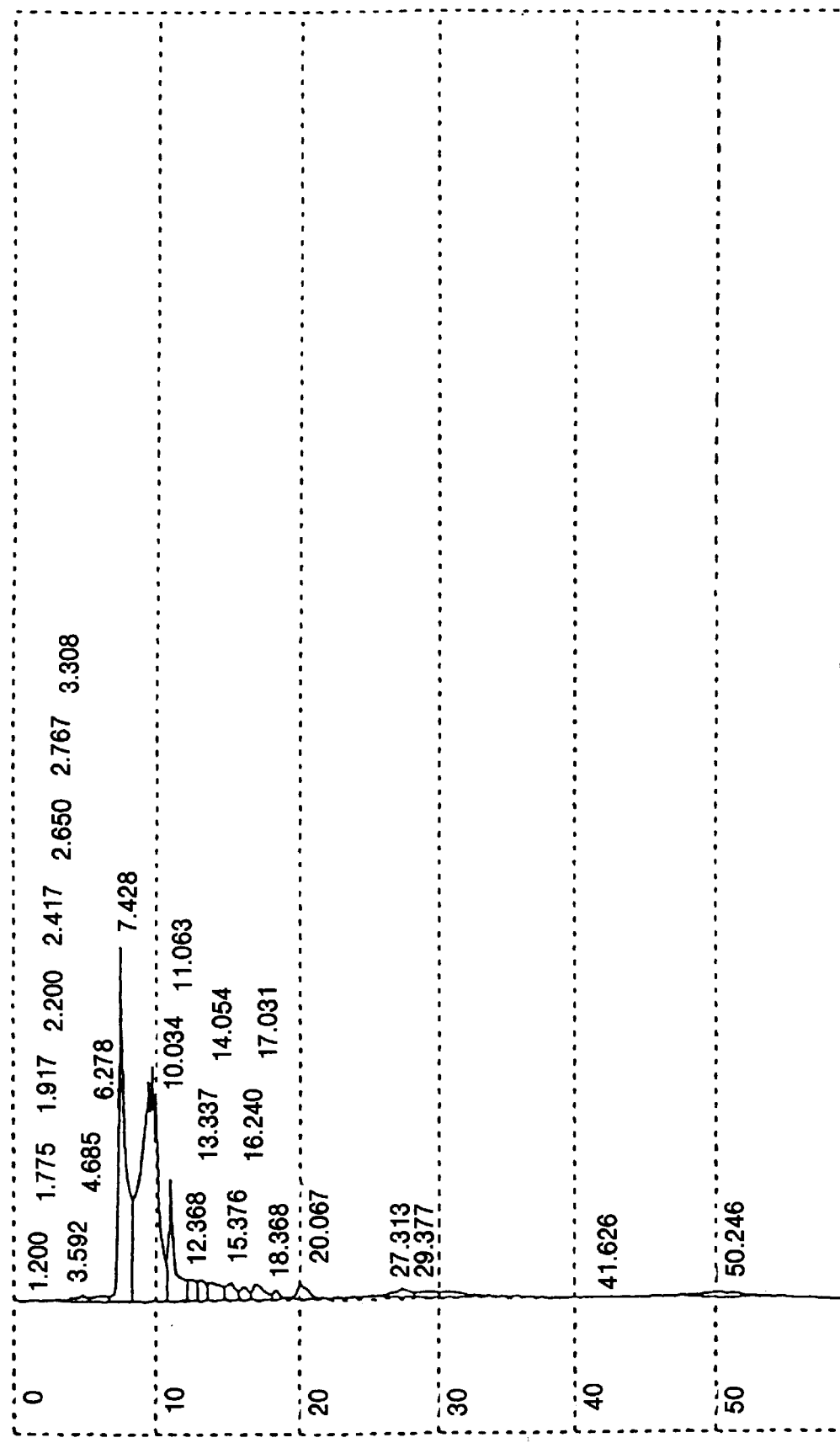
FIG. 9 is a chart obtained by HPLC relating to a lauric acid esters composition of a polyglycerine obtained in Comparative Example 4.
Figure 10:
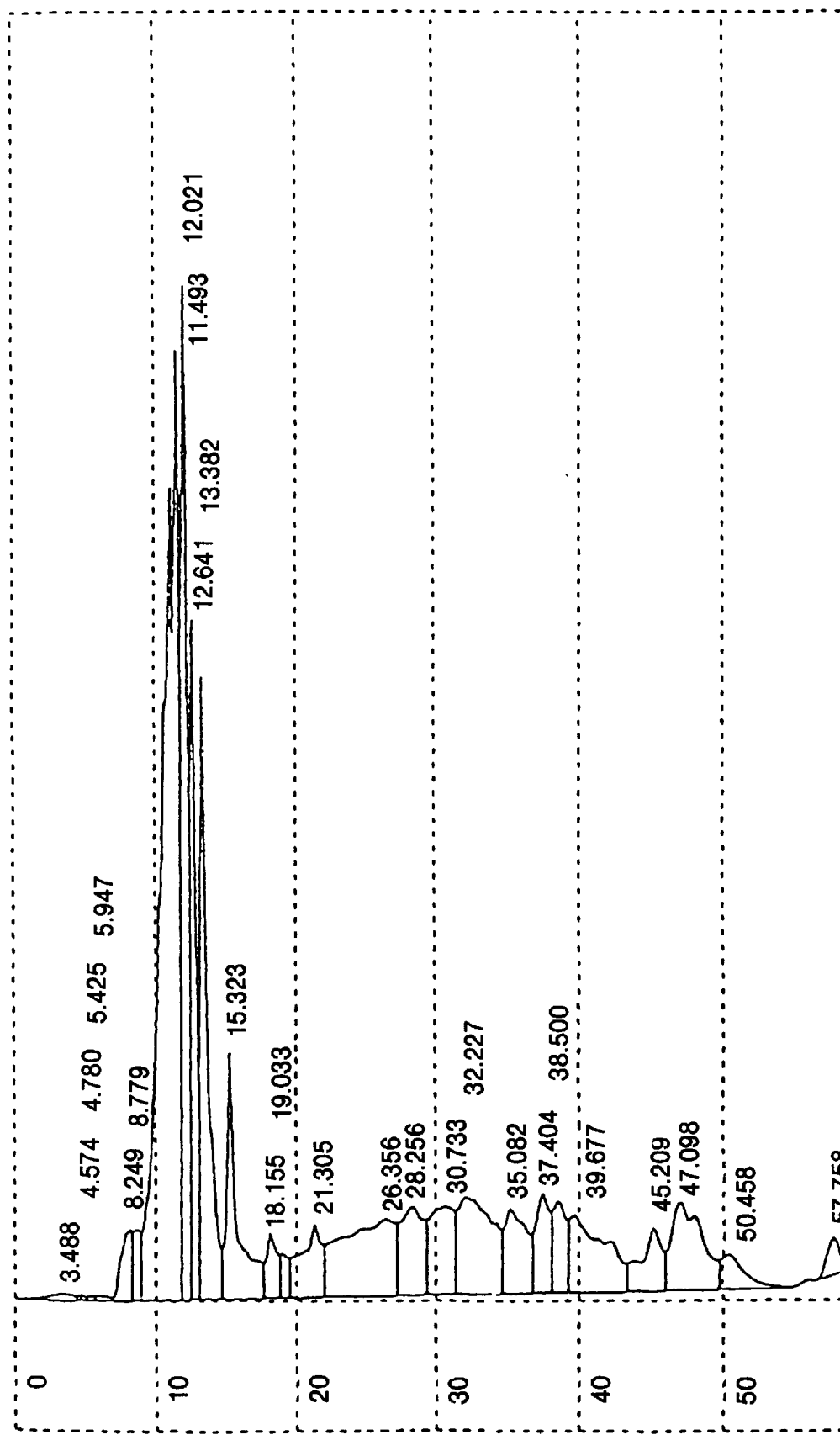
FIG. 10 is a chart obtained by HPLC relating to commercially supplied fatty acid esters composition of a polyglycerine employed in Comparative Example 5.
Figure 11:
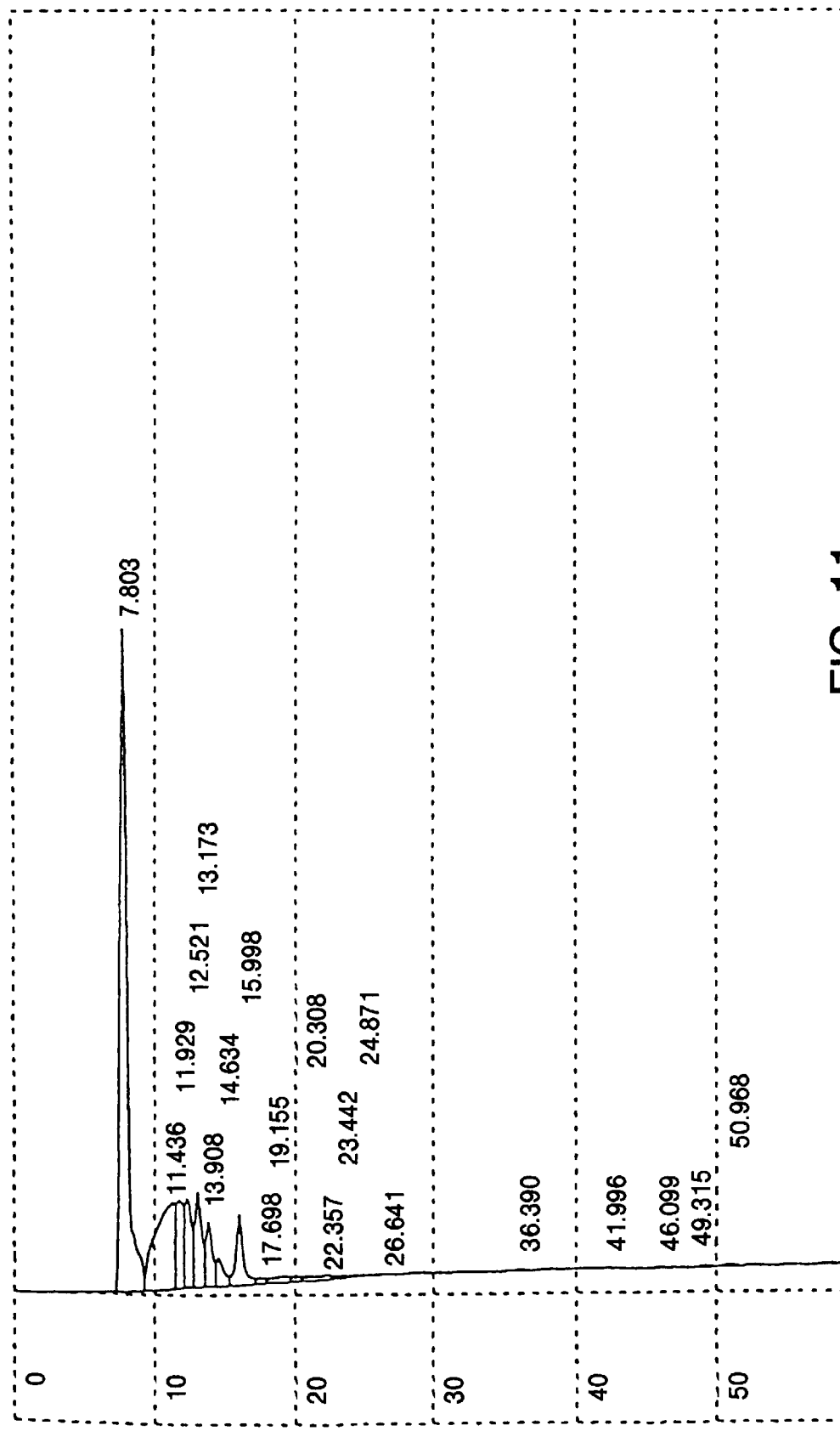
FIG. 11 is a chart obtained by HPLC relating to commercially supplied fatty acid esters composition of a polyglycerine employed in Comparative Example 6.
Figure 12:
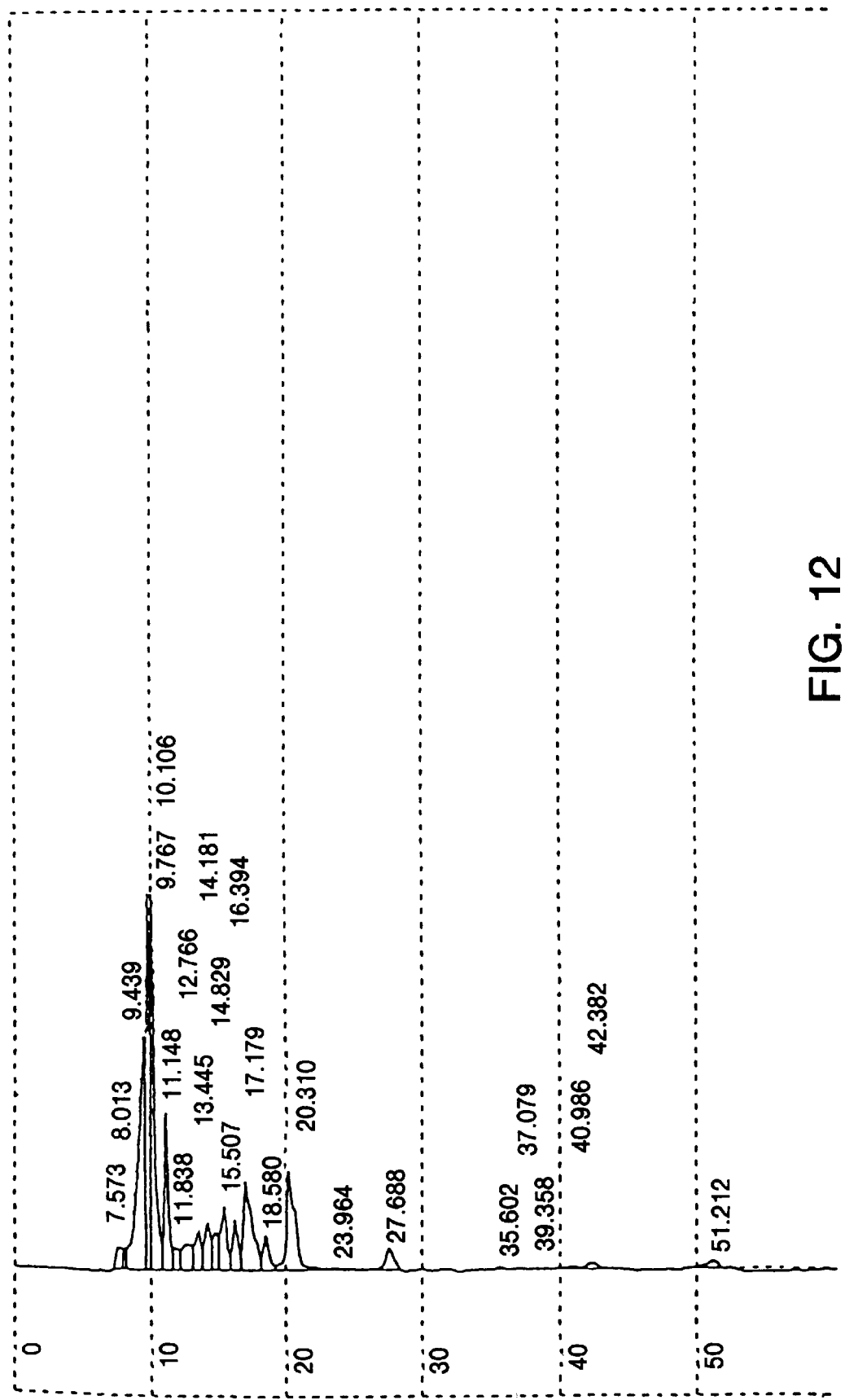
FIG. 12 is a chart obtained by HPLC relating to commercially supplied fatty acid esters composition of a polyglycerine employed in Comparative Example 7.
Figure 13:
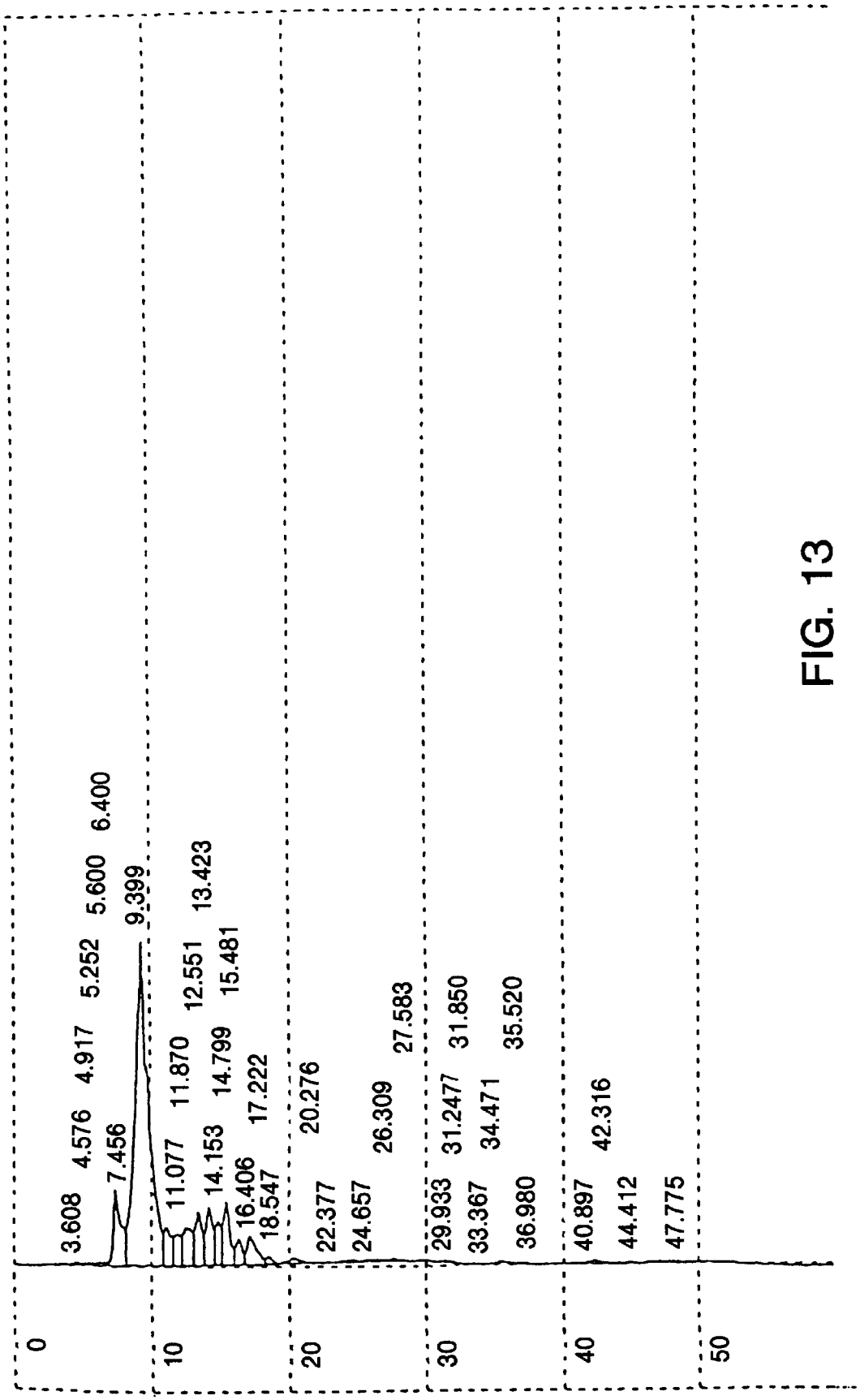
FIG. 13 is a chart obtained by HPLC relating to commercially supplied fatty acid esters composition of a polyglycerine employed in Comparative Example 8.
Figure 14:
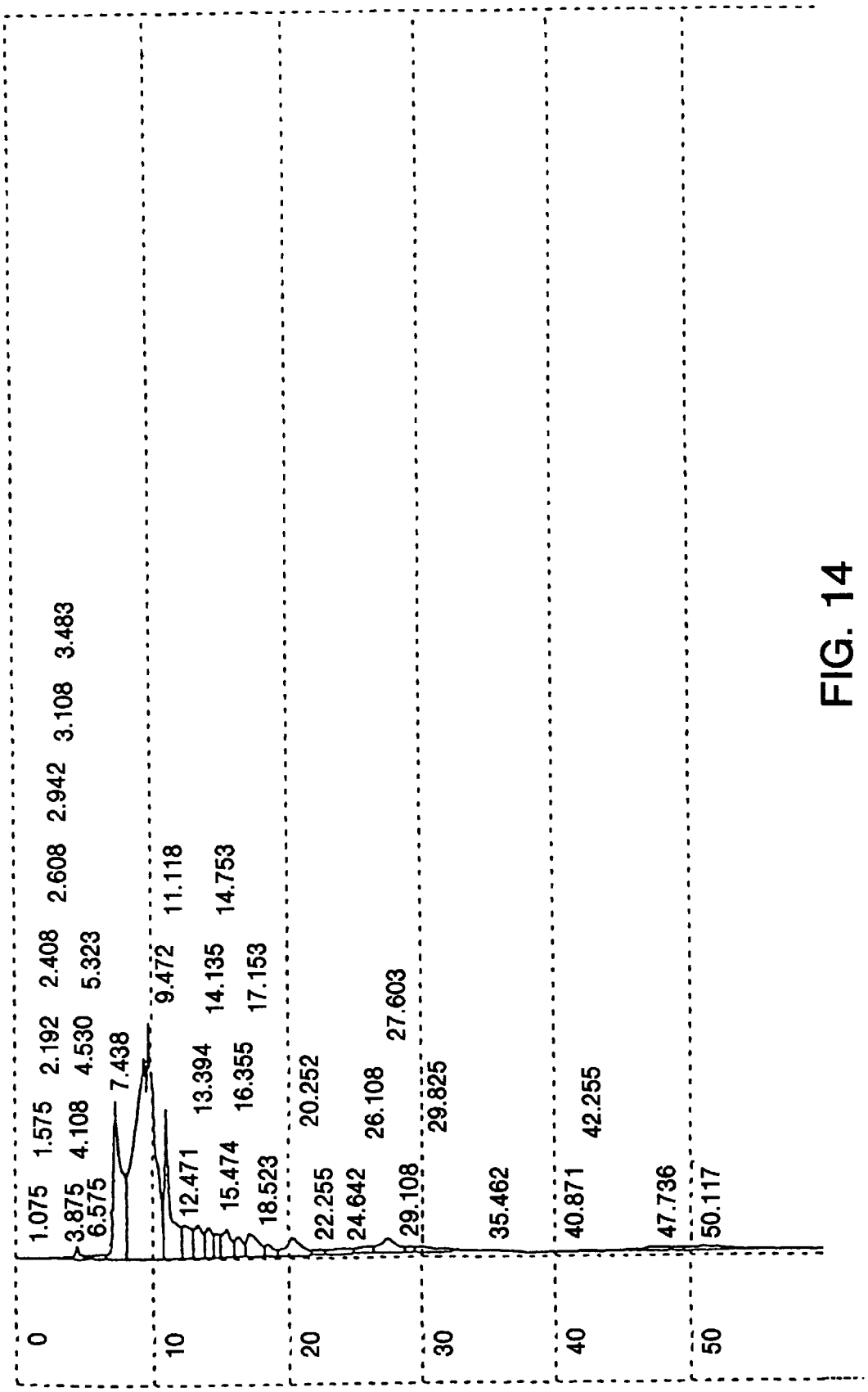
FIG. 14 is a chart obtained by HPLC relating to commercially supplied fatty acid esters composition of a polyglycerine employed in Comparative Example 9.
Figure 15:
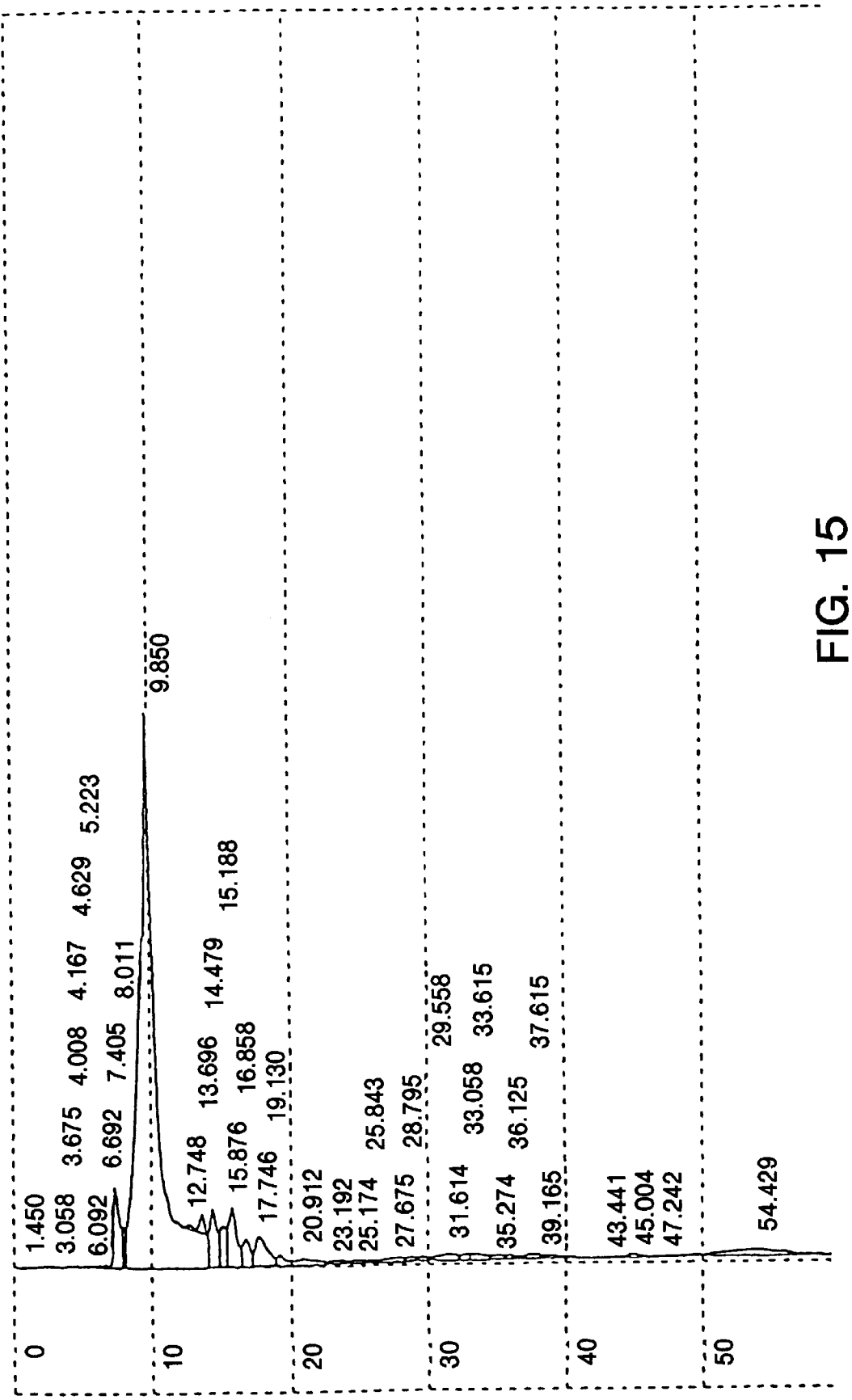
FIG. 15 is a chart obtained by HPLC relating to commercially supplied fatty acid esters composition of a polyglycerine employed in Comparative Example 10.
Figure 16:
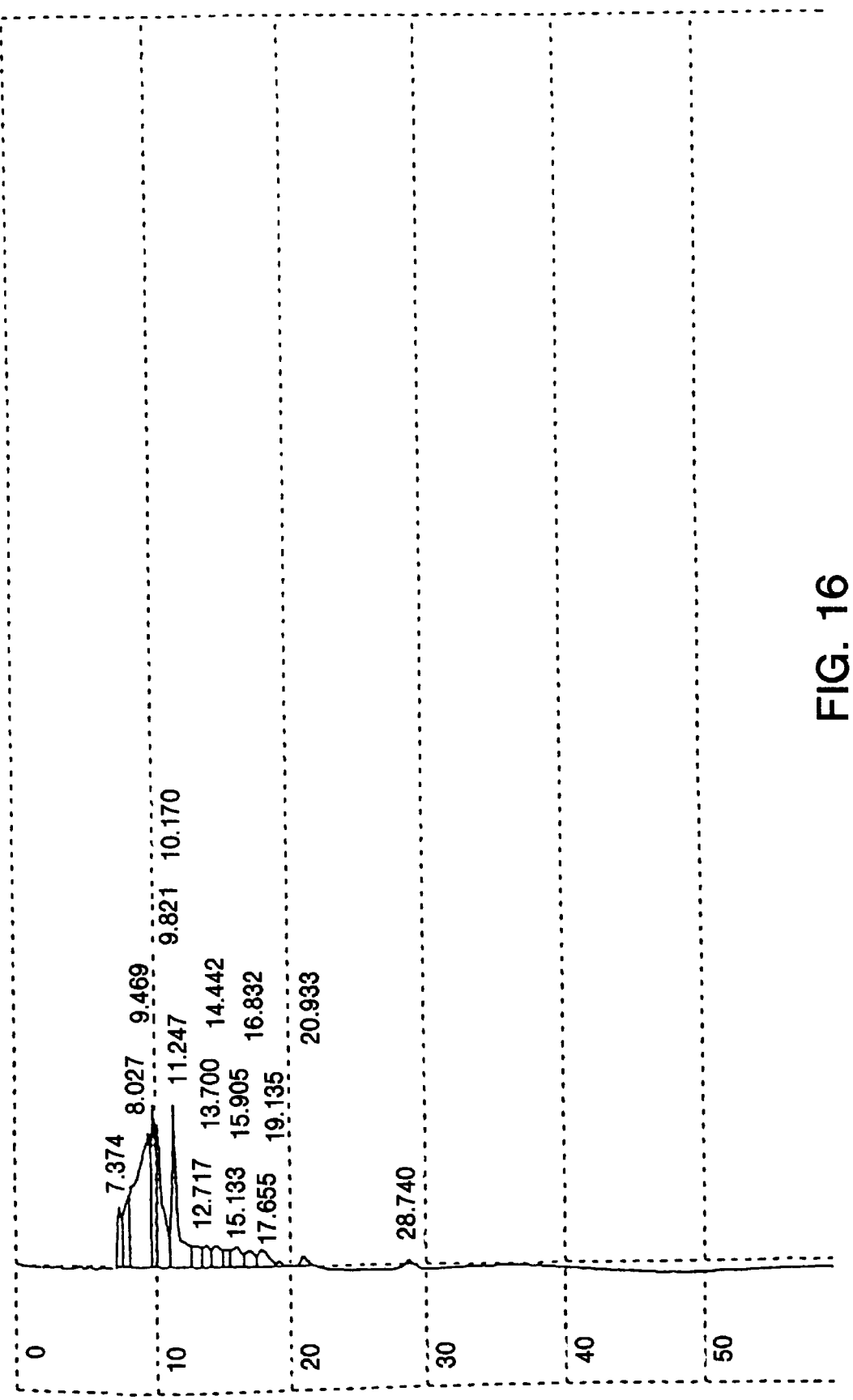
Figure 17:
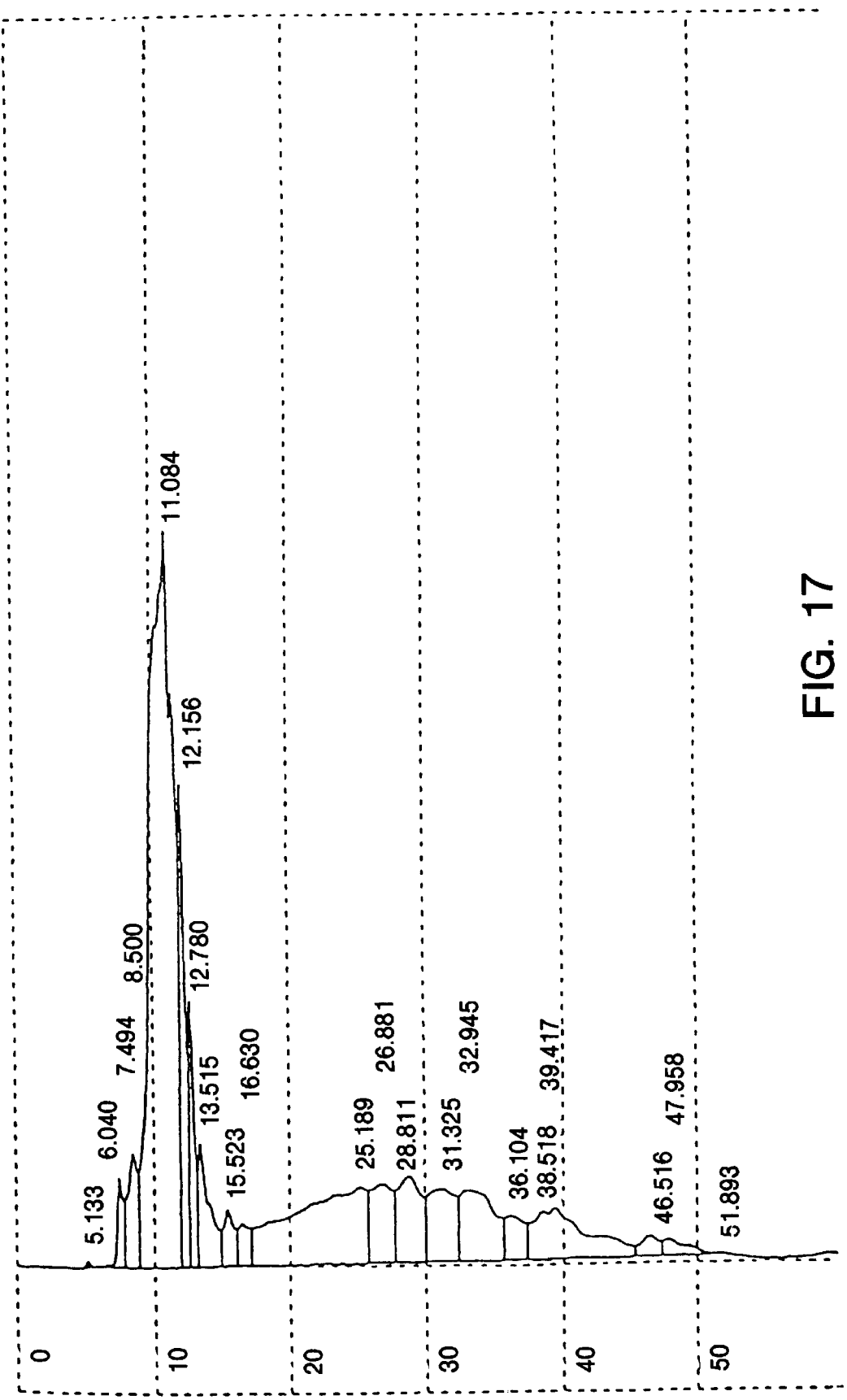
FIG. 17 is a chart obtained by HPLC relating to commercially supplied fatty acid esters composition of a polyglycerine employed in Comparative Example 12.
Figure 18:
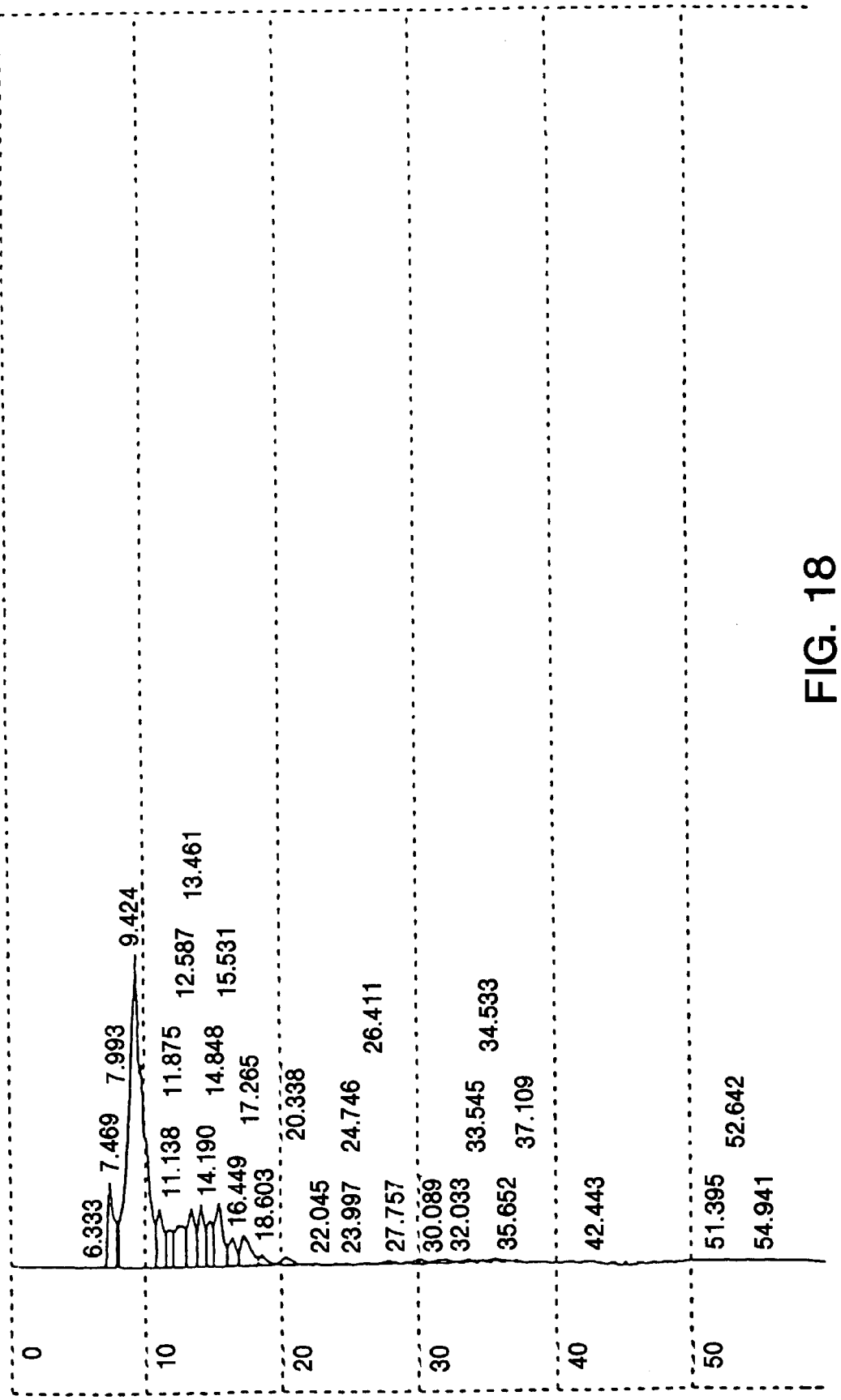
FIG. 18 is a chart obtained by HPLC relating to commercially supplied fatty acid esters composition of a polyglycerine employed in Comparative Example 13.
Figure 19:
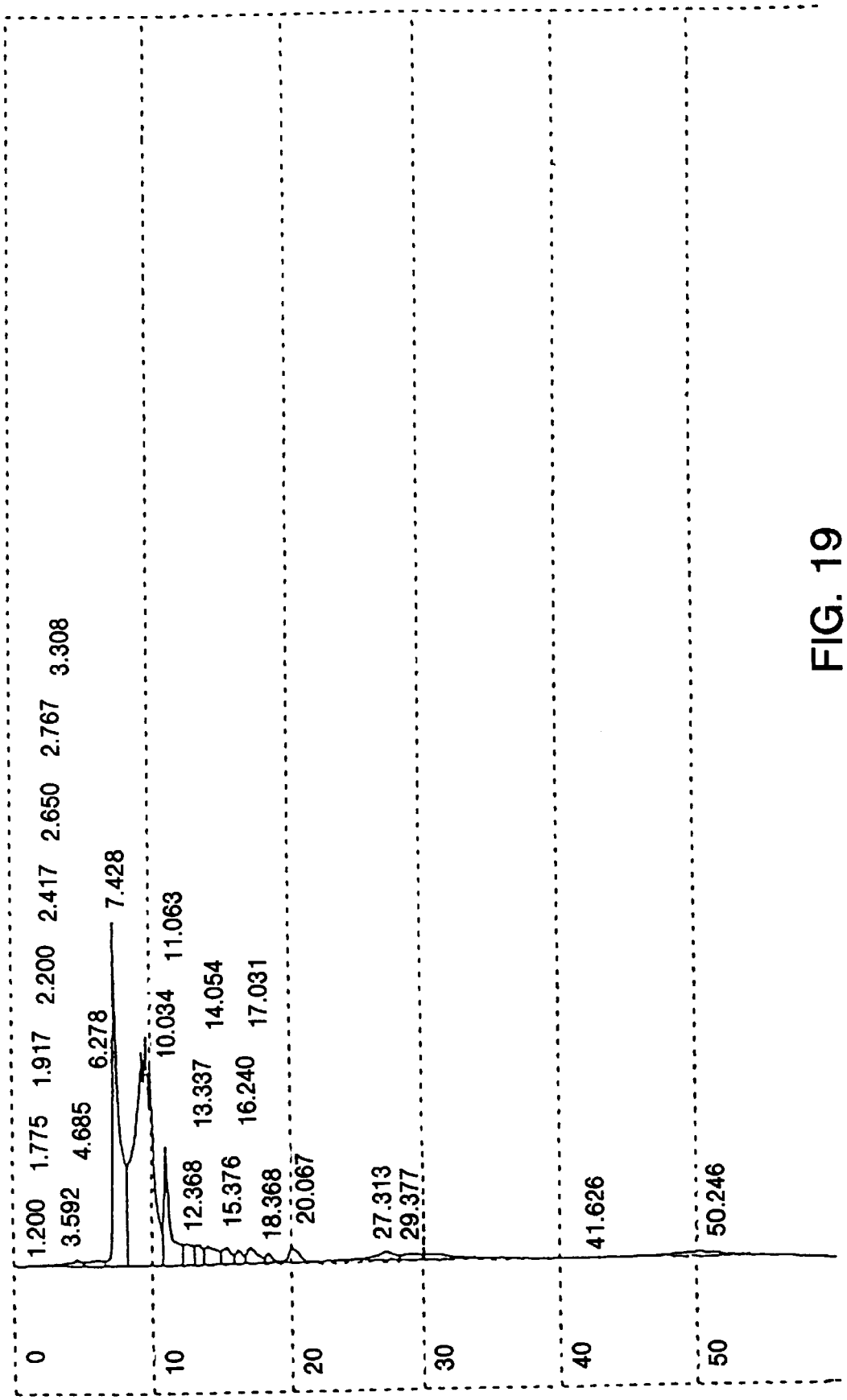
FIG. 19 is a chart obtained by HPLC relating to commercially supplied fatty acid esters composition of a polyglycerine employed in Comparative Example 14.
Figure 20:
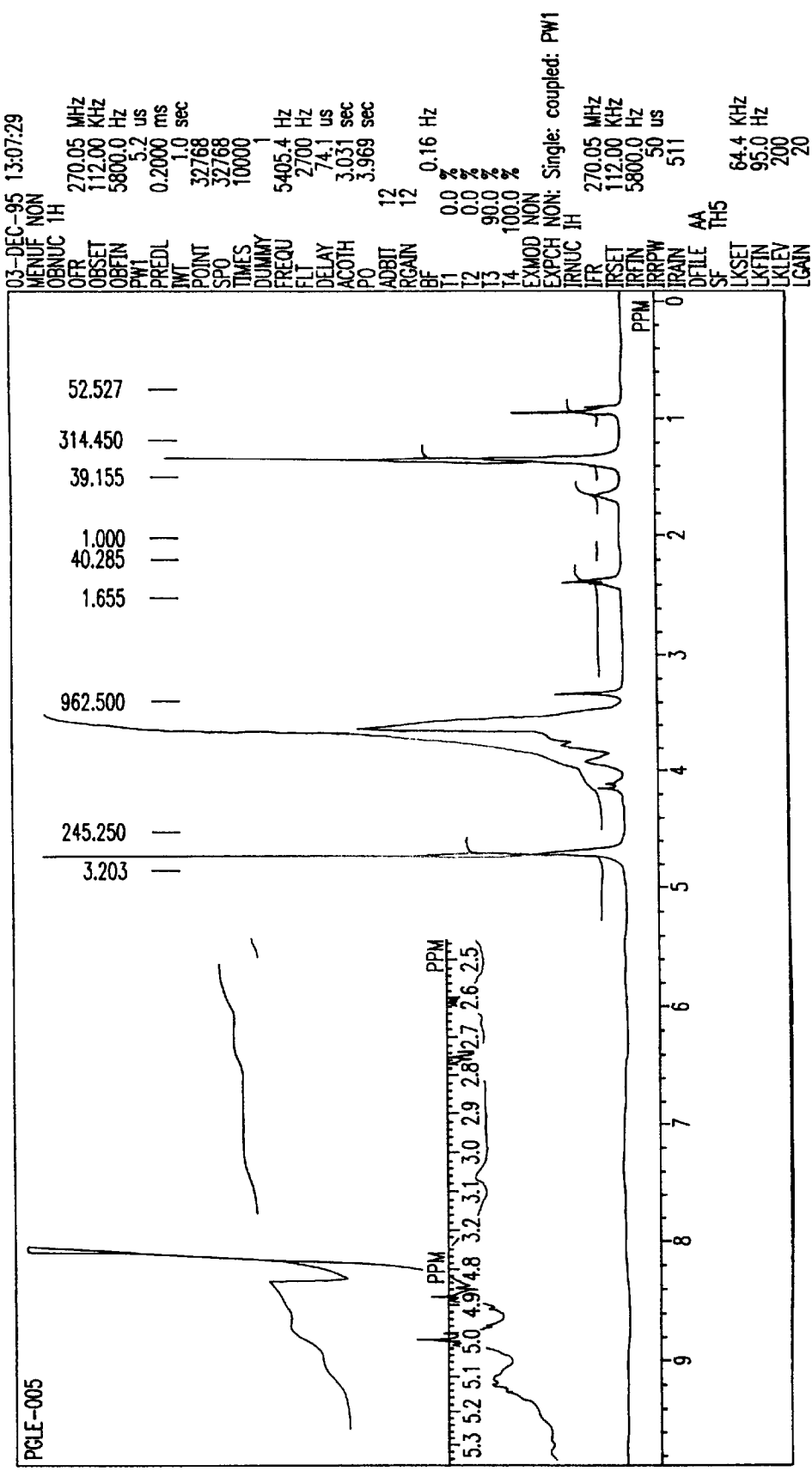
FIGS. 20 and 21 (enlarged chart of 20) are a proton NMR chart relating to the product obtained in Example 6 (first step).
Figure 21:
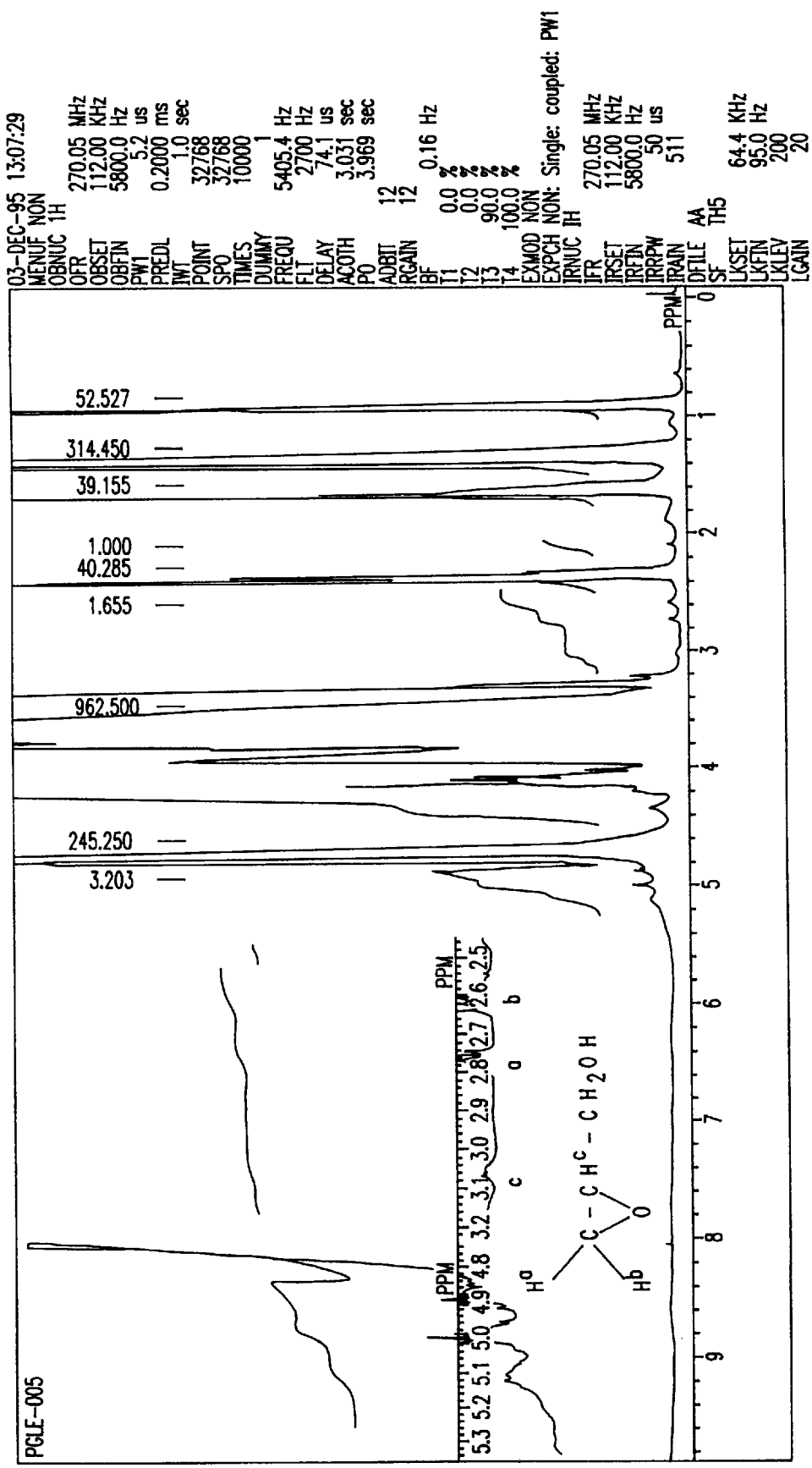
Figure 22:
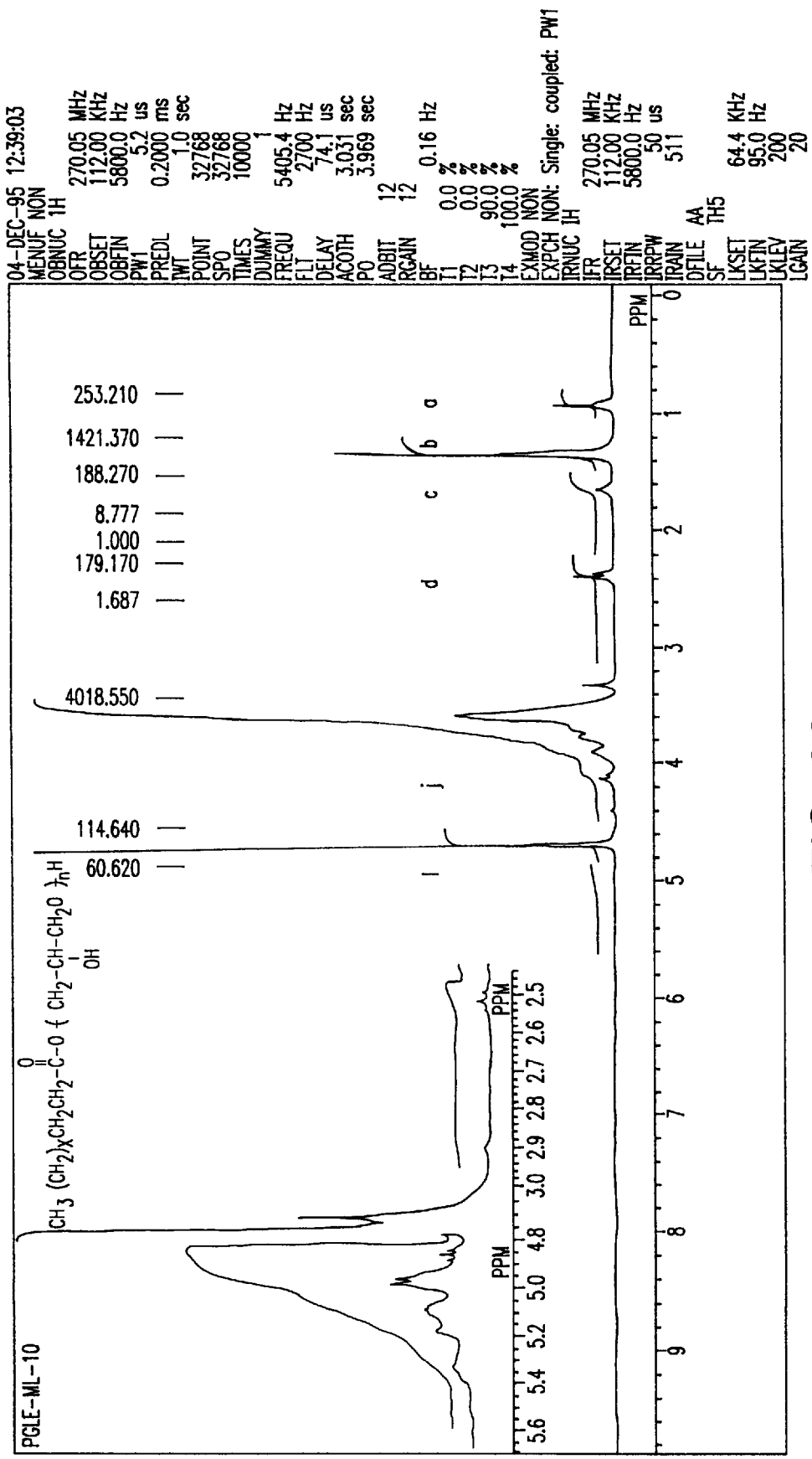
FIGS. 22 and 23 are a proton NMR chart relating to the product obtained in Example 6 (second step).
Figure 23:
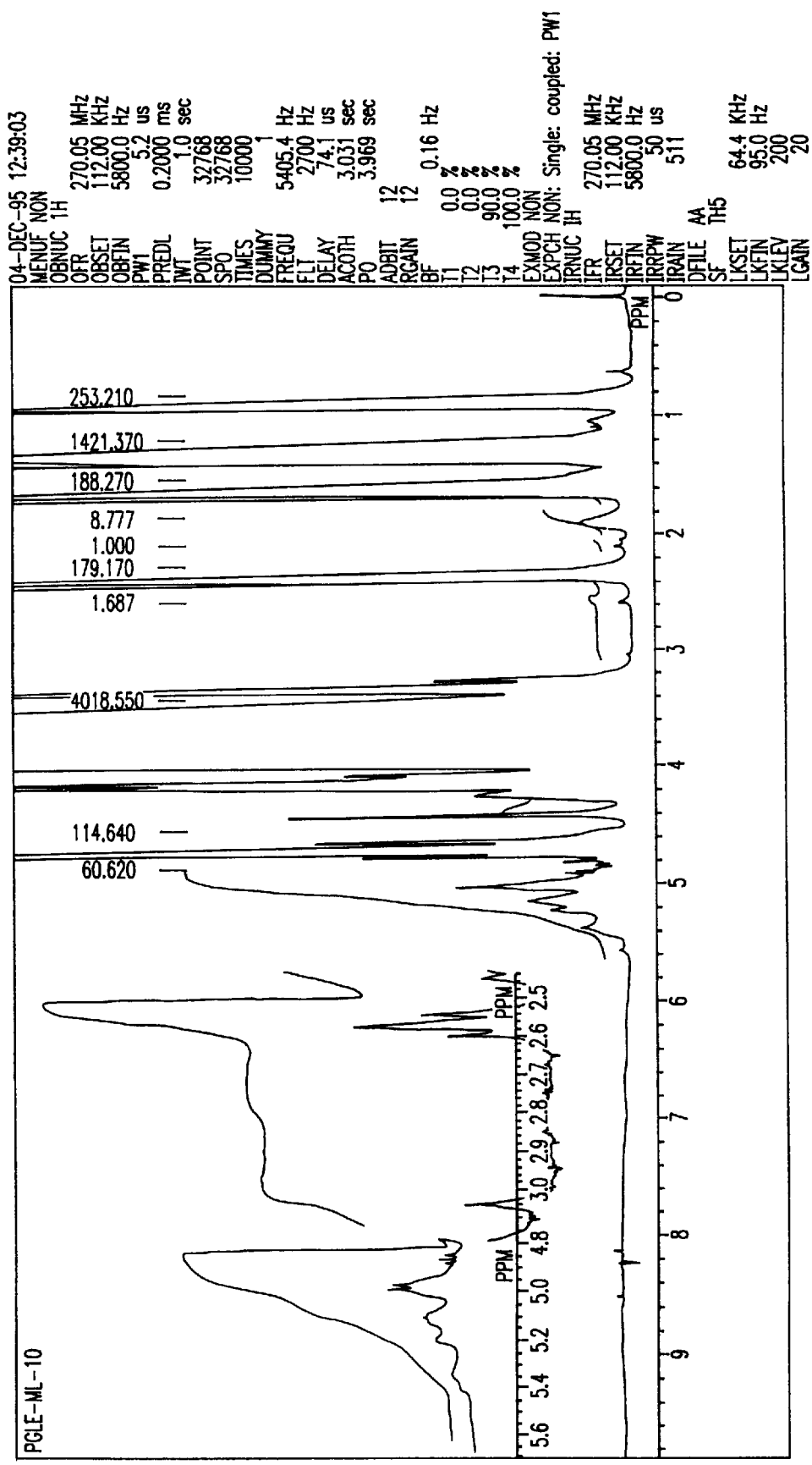

FIG. 9 is a chart obtained by the HPLC analysis relating to the PGMLEC prepared. Results are shown in Table 1.

TABLE 1

|   | Examples |   |   |   |   | Comparative Example |   |   |   |
|---|---|---|---|---|---|---|---|---|---|
|   | 1 | 2 | 3 | 4 | 5 | 1 | 2 | 3 | 4 |
| A | 6 | 6 | 8 | 10 | 10 | 10 | 10 | 10 | 8 |
| B | 12 | 12 | 12 | 12 | 12 | 12 | 12 | 12 | 12 |

TABLE 1-continued

|   | Examples |   |   |   |   | Comparative Example |   |   |   |
|---|---|---|---|---|---|---|---|---|---|
|   | 1 | 2 | 3 | 4 | 5 | 1 | 2 | 3 | 4 |
| C |   |   |   |   |   |   |   |   |   |
| (1) | 87.7 | 90.8 | 84.5 | 77.2 | 77.2 | 53.1 | 52.2 | 44.3 | 55.1 |
| (2) | 3.0 | 2.8 | 11.0 | 15.0 | 15.0 | 4.4 | 5.7 | 12.0 | 17.6 |
| (3) | 9.3 | 6.4 | 4.5 | 7.5 | 7.5 | 42.5 | 42.1 | 43.7 | 27.3 |
| D | Ex | Ex | Ex | Ex | Ex | P | P | P | P |
| E | SW | SW | SW | SW | SW | W | W | W | W |
| F | FY | FY | FY | FY | FY | Y | Y | Y | Y |
| G | T | T | T | T | T | T | T | T | T |
| H | O | O | O | O | O | O | O | O | O |

COMPARATIVE EXAMPLES 5 to 14

Evaluation of fatty acid esters

Fatty acid esters composition of a polyglycerine which is prepared by the reaction of a polyglycerine with a fatty acid was evaluated by visually observing relating to foaming ability and appearances similarly to Examples.

Furthermore, the lauric acid esters composition of a polyglycerine prepared was analyzed by the HPLC analysis similarly to Examples. FIGS. 10 to 19 are charts obtained by the HPLC analysis No. 1 as described hereinabove relating to the PGMLEC prepared, respectively.

Results are shown in Table 2.

TABLE 2

|   | Comparative Example |   |   |   |   |   |   |   |   |   |
|---|---|---|---|---|---|---|---|---|---|---|
|   | 5 | 6 | 7 | 8 | 9 | 10 | 11 | 12 | 13 | 14 |
| PG | (1) | (2) | (3) | (4) | (5) | (6) | (7) | (8) | (9) | (10) |
| A | 4 | 10 | 4 | 6 | 10 | 6 | 10 | 6 | 6 | 10 |
| B | 8 | 8 | 12 | 12 | 12 | 12 | 12 | 8 | 12 | 12 |
| C |   |   |   |   |   |   |   |   |   |   |
| (1) | 50.0 | 41.5 | 47.5 | 52.0 | 44.3 | 65.5 | 53.1 | 53.2 | 52.2 | 55.1 |
| (2) | 2.0 | 4.1 | 1.4 | 6.8 | 12.0 | 3.8 | 4.4 | 3.8 | 5.7 | 17.6 |
| (3) | 48.0 | 54.4 | 51.1 | 41.2 | 43.7 | 30.7 | 42.5 | 43.0 | 42.1 | 27.3 |
| D | P | P | P | P | SP | SP | Ex | P | P | Ex |
| E | W | W | W | W | SW | SW | SW | W | W | SW |
| F | Y | Y | Y | Y | Y | FW | FY | FY | FW | FW |
| G | T | T | T | T | T | T | T | T | T | T |
| H | O | O | O | O | O | O | O | O | O | O |

In the Tables 1 and/or 2, alphabetical abbreviations and numbering are as follows.

PG: fatty acid esters composition of a polyglycerine commercially supplied (1): SY Glystar MO-310 manufactured by Sakamoto Yakuhin Kogyo, Ltd.

(2): SY Glystar MO-750 manufactured by Sakamoto Yakuhin Kogyo, Ltd.

(3): SY Glystar ML-310 manufactured by Sakamoto Yakuhin Kogyo, Ltd.

(4): SY Glystar ML-500 manufactured by Sakamoto Yakuhin Kogyo, Ltd.

(5): SY Glystar MO-750 manufactured by Sakamoto Yakuhin Kogyo, Ltd.

(6): Poem J-6021 manufactured by Riken Vitamin, Ltd.

(7): Poem J-0021 manufactured by Riken Vitamin, Ltd.

(8): Unigly GO-106 manufactured by Nihon Yushi, Ltd.

(9): Unigly GL-106 manufactured by Nihon Yushi, Ltd.
(10): Sunsoft Q12S manufactured by Taiyo Kagaku, Ltd.
A: the number of glycerine unit (pieces)
B: the carbon number of fatty acid
C: peak area ratio by HPLC (UV)
  (1): fatty acid mono ester
  (2): polyglycerine
  (3): others
D: foaming ability (visual observation after vibration with hands for 30 seconds relating to 10% aqueous solution)
  Ex: excellent
  P: poor
E: appearance (at standing still 10% aqueous solution)
  SW: slightly whitening
  W: whitening
F: color hue
  FW: faintly white
  FY: faintly yellow
  Y: yellow
G: appearance (at heating)
  T: transparent
H: appearance (at room temperatures)
  O: opaque

EXAMPLE 6

Preparation No. 1 of a highly-purified fatty acid esters composition of a polyglycerine

First step

A four-necked flask equipped with a tube for supplying nitrogen gas, a stirrer, a cooler, a thermostat, and a dropwise funnel was charged with 100.16 parts by weight of lauric acid and 0.0622 part by weight of phosphoric acid (a plurality of 85%), followed by heating to 140° C. while stirring.

Subsequently, 222.24 parts by weight (molar ratio of glycidol/lauric acid=6) of glycidol was added dropwise over 5 hours to allow to react until oxirane oxygen concentration in the reactant attains below 670 ppm while maintaining the reaction temperature at 140° C. to obtain a product. An acid value of the product obtained in the first step was 0.13 (JIS 1557).

Furthermore, It was identified that the product (a hexaglycerine monolaurate composition) contains a monolaurate of polyglycerine of 87.7%.

Still further, the product was analyzed by the proton NMR in which methandeuterium chloride was employed as a solvent, the solution concentration of the product was approximately 5%, temperature for measuring is 40° C., and JOEL270Mz (manufactured by Nihon Denshi, Ltd.). Results are shown in Tables 20 and 21.

From the proton NMR analysis, it is identified that peak area of a chemical shift between 2.7 ppm and 2.8 ppm assigned by methylene proton in oxirane group is 0.5, and peak area of a chemical shift between 3.4 ppm and 4.4 ppm assigned by methylene proton in polyglycerine and methine proton is 962.6. Peak area ratio is (0.551/962.6)×100=0.52 (%).

It is to be noted that the number 0.551 corresponds to 1.655/3 in which the denominator 3 corresponds to 3 protons (a, b, and c), and the numerator 1.655 corresponds to peak area of 3 protons (a, b, and c).

Second step

After the completion of the first step, water was added into the flask in the amount of 2% by weight based on the product, followed by heating to 135° C. while stirring.

Subsequently, the temperature was maintained while refluxing for 2 hours, followed by raising the temperature to 140° C. Subsequently, distillation was carried out to remove water in a reduced pressure while maintaining the temperature at 140° C.

Reduced pressure degree after 4 hours distillation was 10 mmHg. Oxirane oxygen concentration and acid value in a highly-purified fatty acid esters composition of a polyglycerine obtained were 72 ppm and 0.45, respectively.

Still further, the product was analyzed by the proton NMR similarly to the first step.

Results are shown in Tables 22 and 23.

From the proton NMR analysis, it is identified that peak area of a chemical shift between 2.7 ppm and 2.8 ppm assigned by methylene proton in oxirane group is not observed.

Accordingly, peak area ratio is zero.

EXAMPLE 7

Preparation No. 2 of a highly-purified fatty acid esters composition of a polyglycerine

First Step

Same procedures were repeated as in Example 6

Second Step

After the completion of the first step, water was added into the flask in the amount of 2% by weight based on the product, followed by heating to 120° C. while stirring.

Subsequently, the temperature was maintained while refluxing for 6 hours, followed by raising the temperature to 140° C. Subsequently, distillation was carried out to remove water in a reduced pressure while maintaining the temperature at 140 C.

Reduced pressure degree after 4 hours distillation was 10 mmHg. Oxirane oxygen concentration and acid value in a highly-purified fatty acid esters composition of a polyglycerine obtained were 260 ppm and 0.45, respectively.

EXAMPLE 8

Preparation No. 3 of a highly-purified fatty acid esters composition of a polyglycerine

First step

Same procedure were repeated as in Example 6

Second step

After the completion of the above-described first step, water was added into the flask in the amount of 2% by weight based on the product, followed by heating to 120° C. while stirring. Subsequently, the temperature was maintained while refluxing for 2 hours, followed by raising the temperature to 140° C. Subsequently, distillation was carried out to remove water in a reduced pressure while maintaining the temperature at 140° C.

Reduced degree after 4 hours distillation was 10 mmHg.

Oxirane oxygen concentration and acid value in a highly-purified fatty acid esters composition of a polyglycerine obtained were 430 ppm and 0.45, respectively.

EXAMPLE 9

Preparation No. 4 of a highly-purified fatty acid ester composition of a polyglycerine First step Same procedures were repeated as in Example 6

Second step

After the completion of the first step, water was added into the flask in the amount of 2% by weight based on the product, followed by heating to 140° C. while stirring.

Subsequently, the temperature was maintained while refluxing for 2 hours. Subsequently, distillations was carried out to remove water in a reduced pressure while maintaining the temperature. Reduced pressure degree after 4 hours distillation was 10 mmHg. Oxirane oxygen concentration and acid value in a highly-purified fatty acid esters composition of a polyglycerine obtained were 72 ppm and 0.45, respectively.

It is to be noted that in Examples from 6 to 9, the concentration value of oxirane oxygen in the fatty acid esters composition of a polyglycerine was analyzed according to the titration method defined in Cd. 9-57 of Journal of American Oil Chemists' Society, and it is to be noted that in Examples and Comparative Examples, acid value was analyzed according to JIS 1557.

EXAMPLE 10

Preparation No. 1 of a fatty acid esters composition of a polyglycerine as an additive for a thermoplastic resin A four-necked flask equipped with a tube for supplying nitrogen gas, a stirrer, a cooler, a thermostat, and a dropwise funnel was charged with 284.49 parts by weight of stearic acid and 0.0622 part by weight of phosphoric acid (a purity of 85%), followed by heating to 140° C. Subsequently, 222.24 parts by weight (molar ratio of glycidol/stearic acid=6) of glycidol was added dropwise over 5 hours to allow to react until oxirane oxygen concentration in the reactant attains below 0.1% while maintaining the reaction temperature at 140° C., to obtain approximately 500 parts by weight of a fatty acid esters composition of a polyglycerine (hexaglycerine monostearate composition).

EXAMPLE 11

Preparation No. 2 of a fatty acid esters composition of a polyglycerine as an additive for a thermoplastic resin Same procedures were repeated as in Example 10 except that 296.32 parts by weight (molar ratio of glycidol/stearic acid=8) of glycidol was employed to obtain approximately 575 parts by weight of a fatty acid esters composition of a polyglycerine (octaglycerine monostearate composition).

EXAMPLE 12

Preparation No. 3 of a fatty acid esters composition of a polyglycerine as an additive for a thermoplastic resin)

Same procedures were repeated as in Example 10 except that 100.16 parts by weight (molar ratio of glycidol/lauric acid=6) of lauric acid was employed to obtain approximately 320 parts by weight of a fatty acid esters composition of a polyglycerine (hexaglycerine monolaurate composition).

EXAMPLE 13

Preparation No. 4 of a fatty acid esters composition of a polyglycerine as an additive for a thermoplastic resin Same procedures were repeated as in Example 12 except that 296.32 parts by weight (molar ratio of glycidol/lauric acid=8) of glycidol was employed to obtain approximately 390 parts by weight of a fatty acid esters composition of a polyglycerine (octaglycerine monolaurate composition).

APPLICATION EXAMPLES 1–4 and COMPARATIVE APPLICATION EXAMPLES 1–3

The use of product obtained in Examples 10–13 as an anti-static agent for a thermoplastic resin There was prepared a mixture composed of 100 parts by weight of a polyvinyl chloride (a homopolymer having a polymerization degree of 700), 1.0 part by weight of a mercapt tinoctylate-based stabilizer, 2.0 parts by weight of an epoxidized soy bean oil, 0.5 part by weight of stearic acid, and 10 parts by weight of a reinforced material.

4 parts by weight of respective products obtained in Examples 10–13 and commercially supplied fatty acid esters of polyglycerine as shown in Table 3 were mixed with the mixture to obtain respective films by a calendar process, followed by being biaxially-two fold oriented to obtain files having the thickness of 30 microns. There were measured surface resistance, transparency, and workability in the calendar process of the oriented films. Transparency was evaluated based on Haize value.

Results are shown in Table 3.

TABLE 3

| | | Surface Resistance (ohm) | Transparency | Workability |
|---|---|---|---|---|
| Application Examples | | | | |
| 1 | A | $3.0 \times 10^{12}$ | very good | very good |
| 2 | B | $2.0 \times 10^{12}$ | very good | very good |
| 3 | C | $1.0 \times 10^{12}$ | very good | very good |
| 4 | D | $1.0 \times 10^{12}$ | very good | very good |
| Comparative Application Examples | | | | |
| 1 | E | $5.0 \times 10^{13}$ | good | slightly good |
| 2 | F | $3.0 \times 10^{13}$ | good | slightly good |
| 3 | G | $5.0 \times 10^{14}$ | good | slightly good |

In the Table 3, A, B, C, and D correspond to respective products obtained in Examples 10, 11, 12, and 13, respectively, and E, F, and G correspond to SY-GLYSTAR-MS-500, S-GLYSTAR-ML-500 manufactured by Sakamoto Yakuhin, Ltd., and a glycerine monostearate, respectively.

EXAMPLE 14

Preparation No. 4 of a fatty acid esters composition of a polyglycerine as an additive for a thermoplastic resin A four-necked flask equipped with a tube for supplying nitrogen gas, a stirrer, a cooler, a thermostat, and a dropwise funnel was charged with 100.16 parts by weight of lauric acid and 0.0622 part by weight of phosphoric acid (a purity of 85%), followed by heating to 140° C. Subsequently, 222.24 parts by weight (molar ratio of glycidol/lauric acid= 6) of glycidol was added dropwise over 5 hours to allow to react until oxirane oxygen concentration in the reactant attains below 0.1% while maintaining the reaction temperature at 140° C. for 26 hours, to obtain approximately 300 parts by weight of a fatty acid esters composition of a polyglycerine (a hexaglycerine monolaurate composition). Content of the monoester was 87.7% based on the HPLC analytical condition No. 1 as described hereinabove.

EXAMPLE 15

Preparation No. 5 of a fatty acid esters composition of a polyglycerine as an additive for a thermoplastic resin Same procedures were repeated as in Example 14 except that 296.32 parts by weight (molar ratio of glycidol/lauric acid=8) of glycidol was employed to obtain approximately 400 parts by weight of a fatty acid esters composition of a polyglycerine (an octaglycerine monolaurate composition).

Content of the monoester was 84.5% based on the HPLC method described hereinabove.

EXAMPLE 16

Preparation No. 6 of a fatty acid esters composition of a polyglycerine as an additive for a thermoplastic resin Same procedures were repeated as in Example 14 except that 370.40 parts by weight (molar ratio of glycidol/lauric acid=10) of glycidol was employed to obtain approximately 470 parts by weight of a fatty acid esters composition of a polyglycerine (a decaglycerine monolaurate composition).

Content of the monoester was 77.2% based on the HPLC analytical condition No. 1 as described hereinabove.

COMPARATIVE EXAMPLE 17

Preparation No. 7 of a fatty acid esters composition of a polyglycerine not derived from glycidol as an additive for a thermoplastic resin A four-necked flask equipped with a tube for supplying nitrogen gas, a stirrer, a cooler, a thermostat, and a dropwise funnel was charged with 175.3 parts by weight of a polyglycerine (PGL06 having a hydroxyl value of 960 manufactured by Daicel Chemical Industries, Ltd.), followed by heating at 80° C. Subsequently, 100.16 parts by weight (molar ratio of polyglycerine/lauric acid=1) of lauric acid was dissolved while maintaining 80° C., followed by allowing to react for two hours after adding 0.75 part by weight of sodium carbonate and 0.25 part by weight of sodium hydrogen sulfite at 210° C. After cooling to 100° C., acid value attained 0.89, and a polyglycerine monolaurate composition prepared was taken out. Content of the monoester was 55.1% based on the HPLC analytical condition No. 1 as described hereinabove.

APPLICATION EXAMPLE 5

Evaluation as an agent for improving anti-static property of a styrene-based resin 100 parts by weight of a styrene-based resin having styrene unit of 100% was mixed with 4.0 parts by weight of a hexaglycerine monostearate obtained by Example 1 and 2.0 parts by weight of tristearyl phosphite (JP-318E manufactured by Johoku Kagaku Kogyo, Ltd.) with a Henshel Mixer, followed by being pelletized with an extruder having the cylinder diameter of 40 mm phi (manufactured by Nakaya Kikai).

Pellets were molded by an injection machine (an N70A type manufactured by Nihon Seiko) equipped with a flat molding die [200L×70W×3t] at the cylinder temperature of 240° C. and the molding die temperature of 50° C.) to prepare flat test pieces.

Maximum-charged voltage was 400 V, the half period was 4.2 seconds, and intrinsic surface resistance was $72\times10^{12}$ ohm.

It is to be noted that anti-static property of a styrene-based resin was evaluated by the half period of a maximum charged pressure (Neostmeter S-4104 manufactured by Shishido Syokai), and an intrinsic surface resistance (an intrinsic surface resistance meter, TR-8601 manufactured by Takeda Riken).

APPLICATION EXAMPLE 6

Evaluations as an agent for improving anti-static property of a styrene-based resin The same procedures as described in Application Example 5 were repeated except that there was further mixed 2.0 parts by weight of a polyethyleneglycol having a molecular weight of 300.

Maximum-charged voltage was 380 V, the half period was 3.2 seconds, and intrinsic surface resistance was $56\times10^{12}$ ohm.

APPLICATION EXAMPLE 7

Evaluations as an agent for improving anti-static property of a styrene-based resin The same procedures as described in Example 5 were repeated except that there were employed 8.0 parts by weight of a hexaglycerine monostearate obtained by Example 1 and 6.0 parts by weight of a polyethyleneglycol having a molecular weight of 1000. Maximum-charged voltage was 380 V, the half period was 2.2 seconds, and intrinsic surface resistance was $38\times10^{12}$ ohm.

In the case when the fatty acid esters composition of a polyglycerine is mixed in an amount exceeding 6 parts by weight, although the excellent anti-static property is given to a styrene-based resin, bleeding is unpreferably caused as described hereinabove.

APPLICATION EXAMPLES 8–11

Evaluations as an agent for improving anti-static property of a styrene-based resin Same procedures were repeated as in Application Example 5 except that components were mixed as shown in Table 4.

COMPARATIVE APPLICATION EXAMPLES 4–5

Evaluations as an agent for improving anti-static property of a styrene-based resin Same procedures were repeated as in Application Example 5 except that components were mixed as shown in Table 5.

TABLE 4

| | Application Example | | | |
|---|---|---|---|---|
| | 8 | 9 | 10 | 11 |
| Mixing components | | | | |
| Styrene-based resin | St/MMA | St/AN | St/MMA/MA | St/MMA/MA/CHMI |
| Monomer ratio (wt %) | 50/50 | 60/40 | 40/56/4 | 10/70/5/15 |
| PGLE | MS06 | MS06 | MS06 | MS06 |
| (part by weight) | (4) | (4) | (4) | (4) |
| Phosphorus compound | DP | SP | DP | SP |
| (part by weight) | (2) | (1) | (3) | (1) |
| PAG | 3E | 10E | 10P | — |
| (part by weight) | (0.5) | (1) | (2) | — |
| Properties | | | | |
| MCV (v) | 420 | 420 | 440 | 410 |
| HP (second) | 4.2 | 5.3 | 4.0 | 3.9 |
| SIR (×10) | 55 | 72 | 69 | 85 |

TABLE 5

| | Comparative Application Example | |
|---|---|---|
| | 4 | 5 |
| Mixing components | | |
| Styrene-based resin | St/MMA | St/MMA |
| Monomer ratio (wt %) | 50/50 | 50/50 |
| PGLE | MS06 | — |
| (part by weight) | (4) | — |
| Phosphorus compound | — | SP |
| (part by weight) | — | (2) |
| PAG | — | — |
| Properties | | |
| MCV (v) | 500 | 540 |
| HP (second) | 92 | 210< |
| SIR (×10$^{12}$) | 1800 | 36000 |

In the Tables 4 and 5, abbreviations are as follows.

St: Styrene
MMA: Methylmethacrylate
AN: Acrylonitrile
MA: Methylacrylate
CHM1: Cyclohexylmaleimide
PGLE: Fatty acid esters composition of a polyglycerine
MS06: Hexaglycerine monostearate obtained in Example 2
DP: Tridecylphosphite
SP: Tristearylphosphite
PAG: Polyalkylene glycol
3E: Polyethylene glycol having a molecular weight of 300
10E: Polyethylene glycol having a molecular weight of 1000
10P: Polypropylene glycol having a molecular weight of 1000
MCV: Maximum-charged voltage
HP: Half period
SIR: Surface intrinsic resistance It is clearly identified from the values in Tables 4 and 5 that an excellent anti-static property is given to a styrene-based resin by mixing an appropriate amount of the fatty acid esters composition of a polyglycerine in the present invention.

APPLICATION EXAMPLE 12

Evaluation as a releasing agent for methylmethacrylate-based resin

There were mixed 100 parts by weight of a particle-state methacrylic resin [Sumipex BL0 manufactured by Sumitomo Chemicals Industries, Ltd.], 0.025 part by weight of dipentaerythritol tripalmitate, and 0.025 part by weight of the fatty acid esters composition of a polyglycerine obtained in Example 1 with a Henshel Mixer, followed by being extruded with a vent-type extruder having the cylinder diameter of 40 mm phi to obtain pellets.

Pellets obtained were molded by a 13-ounces injection machine (an M-140SJ type manufactured by Meiki Seisakusyo) equipped with a molding die [25 mm×76.5 mm×3.2 mm] at the cylinder temperature of 260° C., molding die temperature of 60° C., injection pressure of 80 kg/cm$^2$-G, with interval of 60 seconds to evaluate a releasing property while continuously preparing ASTM test pieces for 40 times.

The releasing property was evaluated by comparing the number of broken or cracked pieces in the test pieces. Contamination property in the molding die was evaluated by visually observing the presence or absence of clouding portions in the inner surface of the molding die according to the following levels.

N.C.: no-clouding
X: clouding

Outer appearance in the test pieces was evaluated by visually observing contamination or coloring in pieces.

APPLICATION EXAMPLES 13 to 19

Evaluation as a releasing agent for a methylmethacrylate-based resin

The same procedures were repeated as described in Application Example 12 according to mixing ratio as shown in Table 6.

COMPARATIVE APPLICATION EXAMPLES 6 to 9

Evaluation as a releasing agent for a methylmethacrylate-based resin

The same procedures were repeated as described in Example 24 according to mixing ratio as shown in Table 6.

TABLE 6

| mixing ratio | | RP | CP | OA |
|---|---|---|---|---|
| Application Example | | | | |
| 12 | A (0.025)/E (0.025) | 7.6 | NC | G |
| 13 | A (0.05)/E (0.05) | 6.4 | NC | G |
| 14 | A (0.1)/E (0.1) | 5.0 | NC | G |
| 15 | A (0.03)/E (0.07) | 6.3 | NC | G |
| 16 | A (0.07)/E (0.03) | 6.4 | NC | G |
| 17 | B (0.05)/E (0.05) | 6.6 | NC | G |
| 18 | C (0.05)/E (0.05) | 6.7 | NC | G |
| 19 | D (0.05)/E (0.05) | 6.7 | NC | G |
| Comparative Application Example | | | | |
| 6 | — | 15.0 | NC | G |
| 7 | A (0.1)/— | 12.3 | NC | G |
| 8 | —/E (0.1) | 12.3 | NC | G |

TABLE 6-continued

| mixing ratio | | RP | CP | OA |
|---|---|---|---|---|
| 9 | A (0.3)/E (0.3) | 4.4 | X | SY |

In the Table 6, abbreviations are as follows:
A: Dipentaerythritol tripalmitate
B: Dipentaerythritol hexabehenate
C: Monopentaerythritol
D: Tripentaerythritol
E: Fatty acid esters composition of a polyglycerine obtained in Example 1
RP: Releasing property
CP: Contamination property
OA: Outer appearance
NC: No-clouding
X: Clouding
G: Good
SY: Slightly yellowing It is clearly identified from the values in Table 5 that an excellent releasing property is given to a methylmethacrylate-based resin by mixing an appropriate amount of the fatty acid esters composition of a polyglycerine in the present invention.

EXAMPLE 17

Preparation No. 8 of a fatty acid esters composition of a polyglycerine as an agent for improving properties of a thermoplastic resin A four-necked flask equipped with a tube for supplying nitrogen gas, a stirrer, a cooler, a thermostat, and a dropwise funnel was charged with 284.49 parts by weight of stearic acid and 0.0622 part by weight of phosphoric acid (a purity of 85%), followed by heating to 140° C. Subsequently, 222.24 parts by weight (molar ratio of glycidol/stearic acid=6) of glycidol was added dropwise over 5 hours to allow to react until oxirane oxygen concentration in the reactant attains below 0.1% while maintaining the reaction temperature at 140° C.

There was obtained approximately 500 parts by weight of a fatty acid esters composition of a polyglycerine (a hexaglycerine monostearate composition). The composition is designated E-1.

EXAMPLE 18

Preparation No. 9 of a fatty acid esters composition of a polyglycerine as an agent for improving properties of a thermoplastic resin Same procedures were repeated as in Example 17 except that 296.32 parts by weight (molar ratio of glycidol/stearic acid=8) of glycidol was employed to obtain approximately 565 parts by weight of a fatty acid esters composition of a polyglycerine (an octaglycerine monostearate composition). The composition is designated E-2.

EXAMPLE 19

Preparation No. 10 of a fatty acid esters composition of a polyglycerine as an agent for improving properties of a thermoplastic resin Same procedures were repeated as in Example 17 except that 370.40 parts by weight (molar ratio of glycidol/stearic acid=10) of glycidol was employed to obtain approximately 650 parts by weight of a fatty acid esters composition of a polyglycerine (a decaglycerine monostearate composition).

The composition is designated E-3.

COMPARATIVE PREPARATION EXAMPLE 1

Preparation No. 11 of a fatty acid esters composition obtained by the reaction of fatty acid with a polyglycerine as an agent for improving properties of a thermoplastic resin A four-necked flask equipped with a tube for supplying nitrogen gas, a stirrer, a cooler, a thermostat, and a dropwise funnel was charged with 175.3 parts by weight of a hexaglycerine having a hydroxyl value of 960 [PGL106 manufactured by Daicel Chemical Industries, Ltd.], followed by heating to 80° C. Subsequently, 100.16 parts by weight (molar ratio of hexaglycerine/lauric acid=1) of lauric acid was dissolved while maintaining at 80° C. Subsequently, 0.75 part by weight of sodium carbonate and 0.25 part by weight of sodium hydrogen sulphite were added, followed by allowing to react at 210° C. for 2 hours to obtain a product. After cooling to 100° C., there was taken out the product having an acid value of 0.89.

The product was analyzed by the HPLC analytical condition No. 1 as described hereinabove to identify the content of a lauric monoester compound of polyglycerine (a hexaglycerine monoester composition) of 55.1%.

The product is designated E-4.

COMPARATIVE PREPARATION EXAMPLES 2 and 3

Measurement of the content of monoester compound in commercially supplied fatty acid esters composition As a commercially supplied fatty acid esters composition obtained by the reaction of fatty acid with a polyglycerine, there were evaluated SY Glystar ML-500 and SY Glystar ML-750 (manufactured by Sakamoto Yakuhin Industries).

ML-500 exhibited the content of monoester compound of 52.0%, and ML-750 exhibited the content of monoester compound of 44.3%, ML-500 and ML-750 are designated E-5 and E-6.

Results are shown in Table 7.

PREPARATION EXAMPLE 1

Preparation No. 1 of a polyacetal resin

A polyacetal resin in which 2.8% of ethylene oxide is copolymerized was prepared according to known processes described in U.S. Pat. No. 3,027,352.

The polyacetal resin has an intrinsic viscosity of 1.0 (measured with a m-chlorophenol solution having 2.0% by weight of alpha-pinene containing 0.1% by weight of the polyacetal resin at 60° C.) and melt index of 30.0 g/10 minutes (according to ASTM D1238-57T). The polyacetal resin is designated P-1.

PREPARATION EXAMPLE 2

Preparation No. 2 of a polyacetal resin

The polyacetal resin having an intrinsic viscosity of 1.2 (measured with a m-chlorophenol solution having 2.0% by weight of alpha-pinene containing 0.1% by weight of the polyacetal resin at 60° C.) and melt index of 40.0 g/10 minutes (according to ASTM D1238-57T) in which terminals are acetylated was prepared according to known processes described in U.S. Pat. No. 2,998,409.

The polyacetal resin is designated P-2.

APPLICATION EXAMPLES 20 to 29

Preparation of articles molded from a polyacetal resin composition and evaluations as an agent for improving a printing property by the fatty acid esters composition of the present invention There were mixed 0.2 part by weight of triethyleneglycolbis[3-(3-t-butyl-S-methyl-4-hydroxyphenyl)propionate], the above-prepared polyacetal resins, a hindered amine compound, a fatty acid esters composition of a polyglycerine, and a nucleating agent in a mixing ratio as shown in Tables 4 and 5 under a nitrogen atmosphere, followed by extruding with a L/D=25 single screw extruder (the screw revolution of 100 rpm and the discharge amount of 6 kg/hour) having a vent to prepare pellets.

The pellets were dried, and then molded (the mold temperature of 100° C. and the cooling time of period of 7 seconds) with a 5-ounces molding machine to prepare MFD shutters.

The MFD shutters were irradiated by a corona discharging lamp (irradiation energy of 90 watt, irradiation time of 0.2 second, discharging clearance of 7 mm, and discharging rate of 10 mm/sec). Subsequently, an ink (Tampo R doubleliquid manufactured by Tampo, Ltd.) was printed on a portion of the surface having slightly more than 1 cm square in the respective MFD shutters. Subsequently, curing was carried out at the heating temperature of 120° C. for 20 minutes, followed by cooling at 23° C. and humidity of 50% for 24 hours.

After cooling, cross cut peeling tests were carried out based on JIS K-5400 with cellophane tapes. Cross cut lines were given with the interval of 1 mm a cutter, respectively.

COMPARATIVE APPLICATION EXAMPLES 10 to 19

Evaluations as an agent for improving a printing property by the fatty acid esters composition obtained in Comparative Example 1 and commercially supplied fatty acid esters compositions The same procedures were repeated as described in Application Examples 20 to 29 except that there were employed the hexaglycerine monostearate obtained in Comparative Example 1 SY Glystar DL-500 (manufactured by Sakamoto Yakuhin Industries), and SY Glystar ML-750 (manufactured by Sakamoto Yakuhin Industries).

Evaluations of printing property were based on the following 6 stages.
- 0: no-removed
- 1: slightly removed (total length of removed ink of less than 20 mm and width of less than 0.1 mm)
- 2: slightly removed (total length of removed ink of 20 to 50 mm and width of 0.1–0.2 mm)
- 3: fairly removed (total length of removed of ink of 50< to 100 mm and width of 0.2< to 0.4 mm)
- 4: further removed (total length of removed ink of 100< to 150 mm and width of less than 0.4< to 0.5 mm)
- 5: considerably removed (total length of removed ink of exceeding 150 mm and width of exceeding 0.5 mm).

Printing properties after 1 hour and 1000 hours from printing were evaluated. Results are shown in Tables 7 and 8.

TABLE 7

| | Example | | | | | | | | | |
|---|---|---|---|---|---|---|---|---|---|---|
| | 20 | 21 | 22 | 23 | 24 | 25 | 26 | 27 | 28 | 29 |
| (a) | | | | | | P-1 100 | | | | |
| (b) | D-1 0.01 | D-4 0.01 | D-5 0.05 | D-1 3.0 | D-2 0.1 | D-3 0.1 | D-4 0.01 | D-5 0.01 | D-5 0.08 | D-5 3.0 |
| (c) | E-1 0.05 | E-1 4.0 | E-1 0.1 | E-1 1.0 | E-1 0.2 | E-1 3.0 | E-1 0.01 | E-1 0.5 | E-2 0.2 | E-3 0.2 |
| (d) | | | | | | K-1 | | | | |
| | 100 | 100 | 500 | 500 | 1000 | 500 | 500 | 800 | 800 | 300 |
| (e) | 15.0 | 15.0 | 3.0 | 3.0 | 1.1 | 3.0 | 3.0 | 1.5 | 1.5 | 7.0 |
| (f) | 1 | 1 | 1 | 0 | 0 | 0 | 1 | 1 | 0 | 0 |
| (g) | 1 | 1 | 1 | 0 | 0 | 0 | 1 | 1 | 0 | 0 |

TABLE 8

| | Comparative Application Example | | | | | | | | | |
|---|---|---|---|---|---|---|---|---|---|---|
| | 10 | 11 | 12 | 13 | 14 | 15 | 16 | 17 | 18 | 19 |
| (a) | | | | | | P-1 100 | | | | |
| (b) | D-1 0.01 | D-4 0.01 | D-5 0.05 | D-1 3.0 | D-2 0.1 | D-3 0.1 | D-4 0.01 | D-5 0.01 | D-5 0.08 | D-5 3.0 |
| (c) | E-4 0.05 | E-4 4.0 | E-4 0.1 | E-4 1.0 | E-4 0.2 | E-4 3.0 | E-4 0.01 | E-4 0.5 | E-5 0.2 | E-6 0.2 |

TABLE 8-continued

| | Comparative Application Example | | | | | | | | |
|---|---|---|---|---|---|---|---|---|---|
| | 10 | 11 | 12 | 13 | 14 | 15 | 16 | 17 | 18 | 19 |
| (d) | | | | | | K-1 | | | | |
| | 100 | 100 | 500 | 500 | 1000 | 500 | 500 | 800 | 800 | 300 |
| (e) | 15.0 | 15.0 | 3.0 | 3.0 | 1.1 | 3.0 | 3.0 | 1.5 | 1.5 | 7.0 |
| (f) | 1 | 1 | 1 | 0 | 0 | 0 | 1 | 1 | 0 | 0 |
| (g) | 5 | 4 | 5 | 5 | 5 | 5 | 5 | 5 | 4 | 4 |

In the Tables 7 and 8, abbreviations and alphabetically numbering are as follows.

(a): 100 parts by weight of P-1 (polyacetal polymer) was employed in all the Application Examples and Comparative Application Examples.

(b): Hindered amine compound (part by weight)

D-1:

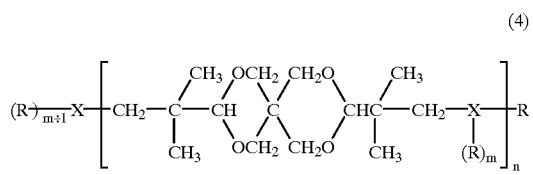

(4)

wherein X is the formula described below,

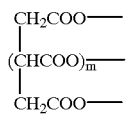

m is 2, and n is 1.5,
and R is the formula described below.

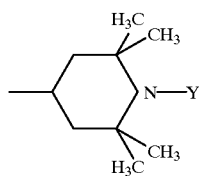

Y is a hydrogen atom.

D-2: In the formula (4), Y is a methyl group, m is 2, and n is 1.5.
D-3: In the formula (4), Y is a methyl group, m is 1, and n is 1.5.
D-4: bis(2,2,6,6-tetramethyl-4-piperidyl)sebacate
D-5: bis(2,2,6,6-tetramethyl-4-piperidyl)adipate (c): E-1/hexaglycerine monostearate obtained in Example 17
E-2/octaglycerine monostearate obtained in Example 18
E-3/decaglycerine monostearate obtained in Example 19
E-4/hexaglycerine monostearate obtained in Comparative Example 1
E-5/SY Glystar ML-500 (manufactured by Sakamoto Yakuhin Industries)
E-6/SY Glystar ML-750 (manufactured by Sakamoto Yakuhin Industries)

(d): K-1/Boron nitride having an average particle size of 2 microns as a nucleating agent (ppm).
(e): Thickness of skin layer (micron)
(f): Printing property after 1 hour
(g): Printing property after 1000 hours By the values in (g) of Tables 7 and 8, it is clearly shown that the fatty acid esters composition of the present invention exhibits an effect for improving printing property in articles molded from the polyacetal resin composition, compared to the fatty acid esters composition obtained in Comparative Example 1 and the commercially supplied fatty acid ester compositions.

EXAMPLE 20

Preparation No. 12 of a Fatty Acid Esters Composition of a Polyglycerine as an Agent for Improving Properties of a Thermoplastic Resin A four-necked flask equipped with a tube for supplying nitrogen gas, a stirrer, a cooler, a thermostat, and a dropwise funnel was charged with 100.16 parts by weight of lauric acid and 0.0622 part by weight of phosphoric acid (a purity of 85%), followed by heating to 140° C. Subsequently, 222.24 parts by weight (molar ratio of glycidol/lauric acid= 6) of glycidol was added dropwise over 5 hours to allow to react until oxirane oxygen concentration in the reactant attains below 0.1% while maintaining the reaction temperature at 140° C.

There was obtained approximately 320 parts by weight of a fatty acid esters composition of a polyglycerine (a hexaglycerine monolaurate composition).

The composition is designated E-1.

EXAMPLE 21

Preparation No. 13 of a Fatty Acid Esters Composition of a Polyglycerine as an Agent for Improving Properties of a Thermoplastic Resin Same procedures were repeated as in Example 20 except that 296.32 parts by weight (molar ratio of glycidol/lauric acid=8) of glycidol was employed to obtain approximately 390 parts by weight of a fatty acid esters composition of a polyglycerine (an octaglycerine monolaurate composition).

The composition is designated E-2.

EXAMPLE 22

Preparation No. 14 of a Fatty Acid Esters Composition of a Polyglycerine as an Agent for Improving Properties of a Thermoplastic Resin Same procedures were repeated as in Example 20 except that 370.40 parts by weight (molar ratio of glycidol/lauric acid=10) of glycidol was employed to obtain approximately 465 parts by weight of a fatty acid esters composition of a polyglycerine (a decaglycerine monolaurate composition).

The composition is designated E-3.

APPLICATION EXAMPLES 30 TO 32

Evaluations as an Agent for Improving a Wetting Property of a Polyacetal Resin by the Fatty Acid Esters Composition of the Present Invention Polyacetal resin (having a trade name of Duracon U10 manufactured by Polyplastics, Ltd.) was mixed with a variety of additives according to respective mixing ratio as shown in Table 8 to prepare a polyacetal resin composition.

Mixing was carried out with a 30-mm twin screw extruder to prepare pellets. Results are shown in Table 9.

TABLE 9

|  | Application Example | | |
| --- | --- | --- | --- |
|  | 30 | 31 | 32 |
| Additives | E-1 | E-2 | E-3 |
| Amount (% by weight) | 0.2 | 0.2 | 0.2 |
| Wetting property (contact angle/degree) | 38 | 40 | 41 |
| Tensile strength (kgf/cm$^2$) | 620 | 615 | 620 |
| Melt Index (g/10 minutes) | 1.0 | 1.0 | 1.0 |

COMPARATIVE APPLICATION EXAMPLES 20 TO 28

Evaluations as an Agent for Improving a Printing Property by the Fatty Acid Esters Composition Obtained in Comparative Example 1 and Commercially Supplied Fatty Acid Esters Compositions The same procedures were repeated as in Application Examples 30 to 32 except that there were employed the fatty acid esters composition obtained in Comparative Example 1 and commercially supplied fatty acid esters compositions.

Results are shown in Table 10.

TABLE 10

|  | Comparative Application Example | | | | | | | | |
| --- | --- | --- | --- | --- | --- | --- | --- | --- | --- |
|  | 20 | 21 | 22 | 23 | 24 | 25 | 26 | 27 | 28 |
| Additives | A-1 | A-1 | A-2 | A-3 | — | B | C | C | D |
| Amount (% by weight) | 0.2 | 0.5 | 0.5 | 0.5 | — | 1.0 | 1.0 | 2.0 | 2.0 |
| Wetting property (contact angle/degree) | 65 | 41 | 40 | 38 | 72 | 70 | 70 | 58 | 60 |
| Tensile strength (kgf/cm$^2$) | 610 | 590 | 600 | 590 | 620 | 570 | 580 | 530 | 510 |
| Melt Index (g/10 minutes) | 1.0 | 1.1 | 1.0 | 1.0 | 1.0 | 1.2 | 1.0 | 1.8 | 1.6 |

In the Tables 9 and 10, abbreviations are as follows.
E-1: Fatty acid esters composition of a polyglycerine obtained in Example 20 (a hexaglycerine monolaurate)
E-2: Fatty acid esters composition of a polyglycerine obtained in Example 21 (an octaglycerine monostearate)
E-3: Fatty acid esters composition of a polyglycerine obtained in Example 22 (a decaglycerine monolaurate)
A-1: Commercially supplied fatty acid esters composition of a polyglycerine (a decaglycerine monolaurate)
A-2: Commercially supplied fatty acid esters composition of a polyglycerine (a decaglycerine monostearate)
A-3: Commercially supplied fatty acid esters composition of a polyglycerine (a octaglycerine monolaurate)
B: Glycerine monolaurate
C: Polyethyleneglycol having a molecular weight of 1000
D: Polyethyleneglycol having a molecular weight of 6000

EXAMPLE 23

Preparation No. 15 of a Fatty Acid Esters Composition of a Polyglycerine as an Agent for Improving Properties of a Thermoplastic Resin A four-necked flask equipped with a tube for supplying nitrogen gas, a stirrer, a cooler, a thermostat, and a dropwise funnel was charged with 142.25 parts by weight of stearic acid and 0.0622 part by weight of phosphoric acid (a purity of 85%), followed by heating to 140 C. Subsequently, 222.24 parts by weight (molar ratio of glycidol/stearic acid=6) of glycidol was added dropwise over 5 hours to allow to react until oxirane oxygen concentration in the reactant attains below 0.1% while maintaining the reaction temperature at 140° C.

There was obtained approximately 260 parts by weight of a fatty acid esters composition of a polyglycerine (a hexaglycerine monolaurate composition). The composition is designated E1.

EXAMPLE 24

Preparation No. 16 of a Fatty Acid Esters Composition of a Polyglycerine as an Agent for Improving Properties of a Thermoplastic Resin The same procedures were repeated as described in Example 23 except that 370.40 parts by weight (molar ratio of glycidol/stearic acid=10) of glycidol was employed.

There was obtained approximately 380 parts by weight of a fatty acid esters composition of a polyglycerine (a decaglycerine monostearate composition). The composition is designated E2.

APPLICATION EXAMPLES 33 TO 41

Evaluations as an Agent for Improving a Releasing Property of a Polyacetal Resin by the Fatty Acid Esters Composition of the Present Invention Polyacetal resin (having a trade name of Duracon-M270 manufactured by Polyplastics, Ltd.) was mixed with a variety of additives according to respective mixing ratio as shown in Table 10 to prepare polyacetal resin compositions.

The polyacetal resin composition was extruded with an extruder to prepare pellets while visually observing the presence or absence of foaming in strands before forming pellets.

Subsequently, the pellets were molded with an injection machine to prepare test pieces. Respective methods for evaluating properties are as follows.

Tensile strength and shear strength:

The test pieces were placed at the conditions of the temperature of 23° C. and the humidity of 50% for 48 hours, followed by measuring with a tensile strength tester (Tensilon manufactured by Orientec, Ltd.) based on ASTM-D638 and ASTM-D732-85.

Amount of gas in melting:

There were stored 8 g of the pellets in a Melt Index tester at 200° C. for 5 minutes, followed by being discharged while loading. Formaldehyde was caught while discharging under loading, followed by being quantitatively measured. The amount of formaldehyde is shown by ppm based on the unit weight of the polyacetal resin.

Continuous injection test:

There was operated an injection machine (manufactured by Toshiba Kikai Plastic Engineering, Ltd.) at the conditions of cylinder temperature of 100° C., injection pressure of 750 kg/cm2, injection time of 4 seconds, cooling time of 3 seconds, and molding die temperature of 30° C. After continuously molding articles having a specific shape at the conditions, the amount of resin scraps adhered was visually measured to evaluate a releasing property according to the following 5 stages.

A: resin scraps are not observed at all
B: a minor amount of resin scraps are only observed
C: resin scraps are slightly observed
D: resin scraps are relatively observed
E: resin scraps are considerably observed Results are shown in Table 11.

TABLE 11

| | Application Example | | | | | | | | |
|---|---|---|---|---|---|---|---|---|---|
| | 33 | 34 | 35 | 36 | 37 | 38 | 39 | 40 | 41 |
| Mixing ratio and additives | | | | | | | | | |
| (A) | 100 | 100 | 100 | 100 | 100 | 100 | 100 | 100 | 100 |
| (B) | fibrous titanium oxide | | | | | | | | |
| Average diameter of fibrous titanium oxide (micron) | 0.1 | 0.2 | 0.1 | 0.1 | 0.1 | 0.1 | 0.2 | 0.1 | 0.1 |
| Average length of fibrous titanium oxide | 8 | 12 | 8 | 8 | 8 | 8 | 8 | 8 | 8 |
| Agent for processing the surface of fibrous titanium oxide | B1 | B1 | B2 | B1 | B1 | B1 | B1 | B1 | B1 |
| (part by weight) | 25 | 25 | 25 | 45 | 25 | 25 | 25 | 25 | 25 |
| (C) | C1 | C1 | C1 | C1 | C2 | C1 | C1 | C1 | C1 |
| (part by weight) | 0.2 | 0.2 | 0.2 | 0.2 | 0.2 | 0.2 | 0.2 | 0.4 | 0.2 |
| (D) | D1 | D1 | D1 | D1 | D1 | D2 | D1 | D1 | D1 |
| (part by weight) | 0.4 | 0.4 | 0.4 | 0.4 | 0.4 | 0.4 | 0.4 | 0.4 | 0.4 |
| (E) | E1 | E1 | E1 | E1 | E1 | E1 | E2 | E1 | E1 |
| (part by weight) | 0.3 | 0.3 | 0.3 | 0.3 | 0.3 | 0.3 | 0.3 | 0.3 | 0.3 |
| Properties | | | | | | | | | |
| Tensile strength (kg/cm$^2$) | 830 | 880 | 820 | 1050 | 840 | 830 | 825 | 820 | 820 |
| Shear strength (kg/cm$^2$) | 590 | 625 | 580 | 730 | 600 | 595 | 590 | 580 | 580 |
| Moldability | | | | | | | | | |
| Bubble in molding | NB | NB | NB | NB | NB | NB | NB | NB | B |
| Continuous injection test | A | A | A | B | A | A | A | A | A |
| Amount of gas (ppm) | 100 | 70 | 105 | 120 | 95 | 95 | 120 | 60 | 70 |

COMPARATIVE APPLICATION EXAMPLES 29 TO 34

Evaluations as an Agent for Improving a Releasing Property by Commercially Supplied Fatty Acid Esters Compositions The same procedures were repeated as described in Application Examples 33 to 41 except that there were employed commercially supplied fatty acid esters compositions.

TABLE 12

| | Comparative Application Example | | | | | |
|---|---|---|---|---|---|---|
| | 29 | 30 | 31 | 32 | 33 | 34 |
| Mixing ratio and additives | | | | | | |
| (A) | 100 | 100 | 100 | 100 | 100 | 100 |
| (B) | fibrous titanium oxide | | | | | |
| Average diameter of fibrous titanium oxide (micron) | 0.3 | 0.3 | 0.1 | 0.1 | 0.1 | 0.1 |
| Average length of | 15 | 15 | 8 | 8 | 8 | 8 |

TABLE 12-continued

| | Comparative Application Example | | | | | |
|---|---|---|---|---|---|---|
| | 29 | 30 | 31 | 32 | 33 | 34 |
| fibrous titanium oxide | | | | | | |
| Agent for processing surface of fibrous titanium oxide | B1 | B1 | B1 | B1 | B1 | — |
| (part by weight) | 25 | 45 | 25 | 25 | 25 | — |
| (C) | C1 | C1 | — | C1 | C1 | C1 |
| (part by weight) | 0.2 | 0.2 | — | 0.2 | 0.2 | 0.2 |
| (D) | D1 | D1 | D1 | — | D1 | D1 |
| (part by weight) | 0.4 | 0.4 | 0.4 | — | 0.4 | 0.4 |
| (E) | E1 | E1 | E1 | E1 | — | E1 |
| (part by weight) | 0.3 | 0.3 | 0.3 | 0.3 | — | 0.3 |
| Properties | | | | | | |
| Tensile strength (kg/cm$^2$) | 900 | 1100 | 835 | 8300 | 835 | — |
| Shear strength (kg/cm$^2$) | 590 | 630 | 590 | 570 | 580 | — |
| Moldability | | | | | | |
| Bubble in molding | NB | NB | NB | NB | NB | B |
| Continuous injection test | D | E | D | D | C | impossible |
| Amount of gas (ppm) | 280 | 510 | 200 | 175 | 180 | — |

In the Tables 11 and 12, alphabetical abbreviations are as follows.

(A): Polyacetal resin (B): Titanium oxide whisker
  B1: N-(2-aminoethyl)-3-aminopropyltrimethoxysilane
  B2: 3-glycidoxypropyltrimethoxysilane (C): Compound having nitrogen
  C1: Melamine
  C2: Calcium stearate (D): Hindered phenol compound
  D1: Pentaerythrityltetrakis[3-(3,5-di-t-butyl-4-hydroxyphenyl)propionate]
  D2: Triethyleneglycol-bis[3-(3-t-butyl-5-methyl-4-hydroxyphenyl)propionate]

(E): Fatty acid esters composition of a polyglycerine
  E1: Fatty acid esters composition of a polyglycerine (hexaglycerine monostearate composition) obtained in Example 23
  E1: Fatty acid esters composition of a polyglycerine (decaglycerine monostearate composition) obtained in Example 24

NB: Absence of bubble
B: Presence of bubble

EXAMPLE 25

Preparation No. 1 of a Fatty Acid Esters Composition of a Polyglycerine as an Additive for Cosmetics A four-necked reaction vessel equipped with a tube for supplying nitrogen gas, a stirrer, a cooler, a thermostat, and a dropwise funnel was charged with 100.16 parts by weight of lauric acid and 0.0622 part by weight of phosphoric acid (a purity of 85%), followed by heating to 140° C. Subsequently, 222.24 parts by weight (molar ratio of glycidol/lauric acid=6) of glycidol was added dropwise over 5 hours to allow to react, followed by further allowing to react for 26 hours while maintaining the reaction temperature at 140° C.

After cooling, the reactant was taken out to obtain approximately 300 parts by weight of a lauric acid esters composition of a polyglycerine. The lauric acid esters composition of a polyglycerine prepared was analyzed by the analytical condition No. 1 in the HPLC analysis as defined hereinabove. It was identified from the chart that the composition (a hexaglycerine monolaurate composition) contains a monolaurate of polyglycerine of 87.7%.

EXAMPLE 26

Preparation No. 2 of a Fatty Acid Esters Composition of a Polyglycerine as an Additive for Cosmetics The same procedures were repeated as described in Example 25, except that there was employed 296.32 parts by weight (molar ratio of glycidol/lauric=8) of glycidol. It was identified from the chart that the composition (an octaglycerine monolaurate composition) contains a monolaurate of polyglycerine of 84.5% by the analytical condition No. 1 in the HPLC analysis as defined hereinabove.

EXAMPLE 27

Preparation No. 3 of a Fatty Acid Esters Composition of a Polyglycerine as an Additive for Cosmetics The same procedures were repeated as described in Example 25, except that there was employed 370.4 parts by weight (molar ratio of glycidol/lauric acid=10) of glycidol. It was identified from the chart that the composition (a decaglycerine monolaurate composition) contains a monolaurate of polyglycerine of 77.2% by the analytical condition No. 1 in the HPLC analysis as defined hereinabove.

APPLICATION EXAMPLES 42 TO 44 AND COMPARATIVE APPLICATION EXAMPLES 35 TO 37

Evaluations as a Water-in-oil Type-emulsified Composition for Cosmetics

There was prepared a water-in-oil type-emulsified composition for cosmetics based on the components and the mixing ratio as described below, respectively.

Liquid paraffin (23% by weight)
Vaseline (6.5% by weight)
Micro-crystalline wax (0.2% by weight)
Lanolin (4.0% by weight)
Bleached bees wax (1.2% by weight)
Tri(caprylic-capric)glyceryl (12% by weight)
Butyl paraoxybenzoate (0.1% by weight)
Glycerine (15% by weight)
Ethyl paraoxybenzoate (0.1% by weight)
Perfume (0.2% by weight)
Purified water (34.2% by weight), (19.2% by weight only in Comparative Application Example 36)
1,3-butyleneglycol (15% by weight only in Comparative Application Example 36)
Fatty acid esters compositions of a polyglycerine (3.5% by weight)

Application Examples:
42: Fatty acid esters composition of a polyglycerine (a hexaglycerine monolaurate composition) prepared in Example 25
43: Fatty acid esters composition of a polyglycerine (an octaglycerine monolaurate composition) prepared in Example 26
44: Fatty acid esters composition of a polyglycerine (a decaglycerine monolaurate composition) prepared in Example 27

Comparative Application Examples
35: Hexaglycerine monolaurate composition prepared in Comparative Example 4 (by the reaction of a fatty acid with a polyglycerine)
36: SY Glystar ML-500 manufactured by Sakamoto Yakuhin Kogyo, Ltd.
37: SY Glystar MO-750 manufactured by Sakamoto Yakuhin Kogyo, Ltd.

Total weight (100% by weight)

In Application Examples 42 to 44, an oily phase containing a fatty acid esters composition of a polyglycerine and glycerine was dissolved by heating to 75° C. Independently, a water phase containing purified water was heated to 75° C.

The water phase was added into the oily phase to emulsify while mixing with an emulsifier, followed by cooling and adding perfumes at 45° C., and then cooling to 30° C.

In Comparative Application Examples, the same procedures were repeated as employed in Application Examples except that 1,3-butyleneglycol was mixed only in Comparative Application Example 36.

Results are shown in Table 13.

TABLE 13

| | Application Examples | | | Comparative Application Example | | |
|---|---|---|---|---|---|---|
| | 42 | 43 | 44 | 35 | 36 | 37 |
| Property | | | | | | |
| Viscosity immediately after prepared | 1570 | 1830 | 1970 | 2540 | 2430 | 2660 |
| Viscosity after 3 months | 1570 | 1830 | 1970 | 2540 | 2430 | 2660 |
| Stability for a long time of period (3 months) | | | | | | |
| Room temperature | − | − | − | + | − | − |
| −5° C. | − | − | − | − | − | − |
| 40° C. | − | − | − | + | ± | ± |
| Feel in use | + | + | + | + | ± | ± |

In the Table 13, methods and standard for evaluation were according to the following stages.
(a) Viscosity: It was measured with a Brookfield viscometer at 25° C.
(b) Stability after 3 months: It was visually evaluated after placed at various temperatures for several months according to the following stages.
−: presence of a separation in emulsified composition
±: presence of a slight separation in emulsified composition
+: presence of a remarkable separation in emulsified composition
(c) Feel in use: Tackiness, spreadability, and oily touch were evaluated by organoleptic tests of 10 professional panelists.
−: a good feel in use
±: a slightly unsatisfied feel in use
+: a slightly unsatisfied feel in use

APPLICATION EXAMPLES 45 TO 48

Evaluations as a Water-in-oil Type-emulsified Composition for Cosmetics

In Application Example 45, a water-in-oil type-emulsified composition was evaluated as an emulsion for cleansing in which the following components are mixed.
Liquid paraffin (23% by weight)
Vaseline (6.5% by weight)
Micro-crystalline wax (0.2% by weight)
Lanolin (4.0% by weight)
Tri(caprylic-capric)glyceryl (12% by weight)
Bleached bees wax (1.2% by weight)
Glycerine (15% by weight)
Fatty acid esters composition of a polyglycerine prepared in Example 25 (3.5% by weight)
Butyl paraoxybenzoate (0.1% by weight)
Ethyl paraoxybenzoate (0.1% by weight)
Perfume (0.2% by weight)
Purified water (34.2% by weight)
Total (100% by weight)

In Application Example 46, a water-in-oil type-emulsified composition was evaluated as an emulsion for body in which the following components are mixed.
Squalene (15% by weight)
Liquid paraffin (8.0% by weight)
Vaseline (6.5% by weight)
Micro-crystalline wax (0.2% by weight)
Lanolin (4.0% by weight)
Lanolin cholestearyl of a fatty acid (0.5% by weight)
Olive oil (12.0% by weight)
Bleached bees wax (1.2% by weight)
Glycerine (15% by weight)
Fatty acid esters composition of a polyglycerine prepared in Example 25 (3.5% by weight)
Decaglyceryl tristearate (0.5% by weight)
Butyl paraoxybenzoate (0.1% by weight)
Methyl paraoxybenzoate (0.1% by weight)
Perfume (0.2% by weight)
Purified water (34.2% by weight)
Total (100% by weight)

In Application Example 47, a water-in-oil type-emulsified composition was evaluated as an emulsion for preventing rough hands in which the following components are mixed.

APPLICATION EXAMPLES 49 TO 51 AND COMPARATIVE APPLICATION EXAMPLES 38 TO 41

Evaluations as a Transparent Liquid Composition for Cosmetics

There was prepared a transparent liquid composition for cosmetics based on the components and the mixing ratio as described below, respectively.
POE oleylether (15.0% by weight)
1,3-butyleneglycol (19.0% by weight)
Squalene (11.0% by weight)
Tri(caprylic-capric)glycerine (11.0% by weight)
Purified water (29.0% by weight)
Fatty acid esters composition of a polyglycerine or an other additive (15.0% by weight)

Application Examples:
- 49: Fatty acid esters composition of a polyglycerine (a hexaglycerine monolaurate composition) prepared in Example 25
- 50: Fatty acid esters composition of a polyglycerine (an octaglycerine monolaurate composition) prepared in Example 26
- 51: Fatty acid esters composition of a polyglycerine (a decaglycerine monolaurate composition) prepared in Example 27

Comparative Application Examples
- 38: Hexaglycerine monolaurate composition prepared in Comparative Example 4 (by the reaction of a fatty acid with a polyglycerine)
- 39: SY Glystar ML-500 manufactured by Sakamoto Yakuhin Kogyo, Ltd.
- 40: SY Glystar MO-750 manufactured by Sakamoto Yakuhin Kogyo, Ltd.
- 41: Sucrose laurate Total weight (100% by weight)
Results are shown in Table 14.

TABLE 14

|  | Application Examples | | | Comparative Application Example | | | |
|---|---|---|---|---|---|---|---|
|  | 49 | 50 | 51 | 38 | 39 | 40 | 41 |
| Property |  |  |  |  |  |  |  |
| HLB | 10.0 | 10.5 | 11.0 | 10.0 | 10.5 | 10.0 | 10.5 |
| Appearance | T | T | T | ST | T | T | ST |
|  | L | L | L | L | G | L | L |
| Spreadability | G | G | G | G | P | G | G |
| Appearance after 1 month | T | T | T | ST | ST | ST | ST |
|  | L | L | L | L | C | L | L |

In the Table 14, abbreviations are follows:
HLB: Hydrophile lipophile balance
T: Transparent
ST: Semi transparent
L: Liquid-state
C: Cream-state
G: Good
P: Poor

APPLICATION EXAMPLES 52 TO 58

Evaluations as a Transparent Liquid Composition for Cosmetics

In Application Example 52, a transparent liquid composition for cosmetics was evaluated as a lotion for body in which the following components are mixed. The components (a) to (c), components (g) and (h) were homogeneously mixed, followed by dispersing the components (d) to (f).

Subsequently, the component (i) was gradually added to obtain a transparent lotion for body having HLB value of 10.5.

The transparent lotion for body was diluted with a proper amount of warm water, resulting in exhibiting a wet and smooth feel in use on body.

(a) Fatty acid esters composition of a polyglycerine obtained in Example 27 (7.4% by weight)
(b) POE (3) oleylether having HLB value of 6.5 (8.1% by weight)
(c) 1,3-butanediol (19.0% by weight)
(d) Tri(caprylic-capric)glycerine (5.5% by weight)
(e) Squalene (11.0% by weight)
(f) Hohoba oil (1.8% by weight)
(g) Perfumes (0.5% by weight)
(h) Antiseptic (0.4% by weight)
(i) Purified water (46.3% by weight)

In Application Example 53, a transparent liquid composition for cosmetics was evaluated as a lotion for bathing in which the following components are mixed. The components (a) to (c), components (g) and (h) were homogeneously mixed, followed by dispersing the components (d) to (f). Subsequently, the component (i) was gradually added to obtain a transparent lotion for bathing having HLB value of 10.5. The transparent lotion for bathing was quickly dispersed, resulting in forming an emulsified liquid.

(a) Fatty acid esters composition of a polyglycerine obtained in Example 27 (7.6% by weight)
(b) Diglycerine monooleate having HLB value of 6.5 (12.0% by weight)
(c) 1,3-butanediol (13.0% by weight)
(d) Tri(caprylic-capric)glycerine (11.5% by weight)
(e) Squalene (11.0% by weight)
(f) Avocado oil (0.4% by weight)
(g) Perfumes (0.5% by weight)
(h) Antiseptic (0.3% by weight)
(i) Purified water (43.7% by weight)

In Application Example 54, a transparent liquid composition for cosmetics was evaluated as a lotion for cleansing in which the following components are mixed. The components (a) to (c), components (g) and (h) were homogeneously mixed, followed by dispersing the components (d) to (f). Subsequently, the component (i) was gradually added to obtain a transparent lotion for cleansing having HLB value of 10.0 which has a good spreadability and a smooth feel in use on skin. Furthermore, washing with water after cleansing was very readily, and it exhibited a refreshing feel in use.

(a) Fatty acid esters composition of a polyglycerine obtained in Example 27 (11.2% by weight)
(b) Sorbitan monoisostearate having HLB value of 5.0 (12.6% by weight)
(c) 1,3-butanediol (17.5% by weight)
(d) Tri(2-ethylhexanic acid)glyceryl (16.0% by weight)
(e) Squalene (14.0% by weight)
(f) Nuts oil (0.5% by weight)
(g) Perfumes (0.3% by weight)
(h) Antiseptic (0.4% by weight)
(i) Purified water (27.5% by weight)

In Application Example 55, a transparent liquid composition for cosmetics was evaluated as a lotion for massaging in which the following components are mixed. The components (a) to (c), components (g) and (h) were homogeneously mixed, followed by dispersing the components (d) to (f). Subsequently, the component (i) was gradually added to obtain a transparent lotion for massaging having HLB value of 10.7 which has a good spreadability and a smooth feel in use on skin. Furthermore, it was readily washed with water after massaging, and was capable of providing a fresh-looking skin.

(a) Fatty acid esters composition of a polyglycerine obtained in Example 27 (12.0% by weight)

(b) POE(3)oleylether having HLB value of 6.5 (9.6% by weight)
(c) 1,3-butanediol (19.0% by weight)
(d) Liquid paraffin (15.0% by weight)
(e) Squalene (10.0% by weight)
(f) Hohoba oil (2.0% by weight)
(g) Perfumes (0.3% by weight)
(h) Antiseptic (0.3% by weight)
(i) Purified water (31.8% by weight)

In Application Example 56, a transparent liquid composition for cosmetics was evaluated as a lotion for an emollient pack in which the following components are mixed. The components (a) to (c), components (h) and (i) were homogeneously dissolved, followed by dispersing the components (d) to (f). Subsequently, the component (k) was gradually added, followed by adding the components (g) and (j) to obtain a lotion for an emollient pack having HLB value of 10.5 which has a good spreadability, an easy coatability in using on face, and makes skin wet and smooth after use. Furthermore, washing with water was very easy even after packing.

(a) Fatty acid esters composition of a polyglycerine obtained in Example 27 (8.9% by weight)
(b) Diglycerine monooleate having HLB value of 6.5 (14.0% by weight)
(c) 1,3-butanediol (22.0% by weight)
(d) Tri(2-ethylhexanic acid)glyceryl (13.0% by weight)
(e) Squalene (12.0% by weight)
(f) Hohoba oil (2.5% by weight)
(g) Extracts from aloe (1.0% by weight)
(h) Perfumes (0.3% by weight)
(i) Antiseptic (0.3% by weight)
(j) Polyvinylpyrrolidone (0.3% by weight)
(k) Purified water (25.7% by weight)

In Application Example 57, a transparent liquid composition for cosmetics was evaluated as a hair treatment in which the following components are mixed. The components (a) to (d), components (i) and (j) were homogeneously dissolved, followed by dispersing the components (e) to (h). Subsequently, the component (l) was gradually added, followed by adding the component (k) to obtain a hair treatment having HLB value of 8.8 which is a transparent liquid. The hair treatment can be directly employed for wetted hairs, and also it was capable of rinsing with tepid water even after lapse of an appropriate time. Hairs exhibited a neat feel in touch.

(a) Fatty acid esters composition of a polyglycerine obtained in Example 27 (4.6% by weight)
(b) Diglycerine monooleate having HLB value of 6.5 (16.2% by weight)
(c) Dimethylammonium distearyl chloride (1.8% by weight)
(d) 1,3-butanediol (18.0% by weight)
(e) Dodecanol octylate (7.0% by weight)
(f) Squalene (16.0% by weight)
(g) Hohoba oil (2.3% by weight)
(h) Silicon oil (0.3% by weight)
(i) Perfumes (0.3% by weight)
(j) Antiseptic (0.3% by weight)
(k) Dyes (a proper amount)
(l) Purified water (33.3% by weight)

In Application Example 58, a transparent liquid composition for cosmetics was evaluated as a base material for medicines in which the following components are mixed. The components (a) to (c), and the component (g) were homogeneously dissolved, followed by dispersing the components (d) to (f). Subsequently, the component (h) was gradually added to obtain a base material for medicines. It was transparent, liquid, and excellent in spreadability.

(a) Fatty acid esters composition of a polyglycerine obtained in Example 27 (8.3% by weight)
(b) Diglycerine monooleate having HLB value of 6.5 (11.4% by weight)
(c) 1,3-butanediol (13.0% by weight)
(d) Tri(caprylic-capric)glycerine (7.0% by weight)
(e) Squalene (15.0% by weight)
(f) Olive oil (1.0% by weight)
(g) Antiseptic (0.2% by weight)
(h) Purified water (44.1% by weight)

APPLICATION EXAMPLES 59 TO 64 AND COMPARATIVE APPLICATION EXAMPLES 42 TO 44

Evaluations as a Gel-like Emulsified Composition for Cosmetics

In the Application Examples and Comparative Application Examples, methods and standard for evaluation were according to the following stages.

(a) Stability after placing at 40° C. for 60 days: It was visually evaluated according to the following stages.
+: absence of a separation in composition
−: presence of a separation upper or lower layer in composition
(b) Viscosity: It was measured with a Brookfield viscometer (spindle #4) at 25° C.
(c) Feel in use: It was evaluated by organoleptic tests of 5 professional panelists.
+: Good evaluation by all the members
−: Good evaluation by members not exceeding 4

There was prepared a gel-like emulsified composition for cosmetics based on the components and the mixing ratio as described below, respectively.

(a) 1,3-butanediol (3.0% by weight)
(b) Purified water (3.0% by weight)
(c) Liquid paraffin (75.0% by weight)
(d) Glycerine (15.0% by weight)
(e) Perfumes (0.50% by weight)
(g) Fatty acid esters composition of a polyglycerine (3.5% by weight)

Application Example 59:
Composition obtained in Example 25
Application Example 60:
Composition obtained in Example 26
Application Example 61:
Composition obtained in Example 27
Comparative Application Example 42:
Hexaglycerine monolaurate composition prepared in Comparative Example 4 (by the reaction of a fatty acid with a polyglycerine)
Comparative Application Example 43:
SY Glystar ML-500 manufactured by Sakamoto Yakuhin Kogyo, Ltd.
Comparative Application Example 44:
SY Glystar MO-750 manufactured by Sakamoto Yakuhin Kogyo, Ltd.

TABLE 15

|  | Application Examples | | | Comparative Application Example | | |
| --- | --- | --- | --- | --- | --- | --- |
|  | 59 | 60 | 61 | 42 | 43 | 44 |
| Property |  |  |  |  |  |  |
| Stability (for 1 month at 40 C.) | + | + | + | + | + | − |
| Viscosity (cps) | 7000 | 7600 | 8100 | 9000 | 9500 | 9700 |
| Feel in use | + | + | + | − | − | + |

In Application Example 62, there was prepared a gel-like emulsified composition for cosmetics based on the components and the mixing ratio as described below, respectively.
The composition was evaluated as gel for a cleansing.
(a) 1,3-butanediol (2.0% by weight)
(b) Purified water (1.6% by weight)
(c) Liquid paraffin (56.0% by weight)
(d) Glycerine (37.0% by weight)
(e) Sodium hyaluronate (0.002% by weight)
(f) Perfumes (0.20% by weight)
(g) Fatty acid esters composition of a polyglycerine obtained in Example 27 (3.0% by weight)

In Application Example 63, there was prepared a gel-like emulsified composition for cosmetics based on the components and the mixing ratio as described below, respectively.
The composition was evaluated as a gel for massaging.
(a) 1,3-butanediol (2.0% by weight)
(b) Purified water (2.8% by weight)
(c) Liquid paraffin (25.0% by weight)
(d) Trioctanic glyceryl (25.0% by weight)
(e) Glycerine (42.0% by weight)
(f) Sodium hyaluronate (0.002% by weight)
(g) Perfumes (0.20% by weight)
(h) Fatty acid esters composition of a polyglycerine obtained in Example 27 (3.0% by weight)

In Application Example 64, there was prepared a gel-like emulsified composition for cosmetics based on the components and the mixing ratio as described below, respectively.
The composition was evaluated as a wiping liquid for making-up.
(a) Decaglycerylmonomilystate (1.5% by weight)
(b) 1,3-butanediol (2.0% by weight)
(c) Purified water (11.3% by weight)
(d) Liquid paraffin (40.0% by weight)
(e) Glycerine (42.0% by weight)
(f) Sodium hyaluronate (0.001% by weight)
(g) Perfumes (0.20% by weight)
(h) Fatty acid esters composition of a polyglycerine obtained in Example 25 (3.0% by weight)

All the gel-like emulsified compositions for cosmetics in Application Examples 62 to 64 exhibited an excellent stability and excellent feel in use.

<APPLICATION EXAMPLES 65 to 67 AND COMPARATIVE APPLICATION EXAMPLES 45 to 48/

Evaluations as a composition for tooth paste>

In Application Example 65, there was prepared a composition for tooth paste based on the components and the mixing ratio as described below, respectively.

(a) Dihydrate of calcium secondary phosphate (45.00% by weight)
(b) Carboxymethyl cellulose (0.50% by weight)
(c) Carrageenan (0.50% by weight)
(d) Glycerine (10.0% by weight)
(e) Sorbitol (10.0% by weight)
(f) Water (28.70% by weight)
(g) Fatty acid esters composition of a polyglycerine obtained in Example 25 (2.00% by weight)
(h) Perfumes (1.00% by weight)
(i) Sodium saccharide (0.20% by weight)
(j) Sterilizer and Antiseptic (0.10% by weight)

In Application Example 66, the same components in Application Example 65 were employed except that there was employed the fatty acid esters composition of a polyglycerine obtained in Example 26 as the component (g).

In Application Example 67, the same components in Application Example 65 were employed except that there was employed the fatty acid esters composition of a polyglycerine obtained in Example 27 as the component (g).

In Comparative Application Example 45, the same components in Application Example 65 were employed except that there was employed the hexaglycerine monolaurate composition prepared in Comparative Example 4 <by the reaction of a fatty acid with a polyglycerine> as the component (g).

In Comparative Application Example 46, the same components in Application Example 65 were employed except that there was employed SY Glystar ML-500 manufactured by Sakamoto Yakuhin Kogyo, Ltd. as the component (g).

In Comparative Application Example 47, the same components in Application Example 65 were employed except that there was employed SY Glystar ML-750 manufactured by Sakamoto Yakuhin Kogyo, Ltd. as the component (g).

In Comparative Application Example 48, the same components in Application Example 65 were employed except that there was employed a sucrose laurate as the component (g).

Results are shown in Table 16.

TABLE 16

|  | Application Examples | | | Comparative Application Example | | | |
| --- | --- | --- | --- | --- | --- | --- | --- |
|  | 65 | 66 | 67 | 45 | 46 | 47 | 48 |
| Foaming ability | 480 | 500 | 460 | 290 | 300 | 260 | 250 |
| Foamed volume feeling in mouth | G | G | G | SP | P | SP | SP |

In the Application Examples and Comparative Application Examples, methods and standard for evaluation were according to the following stages.

(a) Foaming ability: It was evaluated by measuring volume of foam after agitating at 60V with a National mixer (MX-420) for 90 seconds. Beforehand, samples were prepared by suspending 5g of composition for tooth paste in 50 ml of water warmed at 30° C.
(b) Foamed volume feeling in mouth: It was evaluated by organoleptic tests of 5 panelists.
  G: Presence of foaming
  SP: Presence of slightly foaming
  P: Absence of foaming As shown in Table 16, there can be obtained a composition for tooth paste having excellent foaming ability, a refreshing feel in use, no-irritation at mucous membrane in mouth, no-depression of enzymes by employing the fatty acid esters composition of a polyglycerine specified in the present invention.

<APPLICATION EXAMPLES 68 to 71 AND COMPARATIVE APPLICATION EXAMPLES 49 to 53/

Evaluations as a Cleaning agent composition>

In Application Example 68, there was prepared a cleaning agent composition based on the components and the mixing ratio as described below, respectively.

(a) Glycerine succinate monolaurate (5.0 parts by weight)
(b) Fatty acid esters composition of a polyglycerine obtained in Example 25 (11.0 parts by weight)
(c) Sodium tripolyphosphate (35.0 parts by weight)
(d) Sodium sulfuric anhydride (49.0 parts by weight)
(e) Deionized water (100 parts by weight)

The components (c) and (d) were mixed with a mixture composed of (a) and (b), and further component (e) was added, followed by mixing at 60° C. to obtain a homogeneous liquid.

Subsequently, sulfuric acid was added in order to adjust to PH of 7.0, followed by spray-drying to obtain a cleaning agent composition.

In a 500-ml beaker, 1.3 g of the cleaning agent composition was dissolved in 400 ml of tap water at 25° C. while agitating with a magnetic stirrer to obtain a solution.

Separately, 4 glass plates having 5 cm L×2 cm W×0.5 mm t were coated with 0.03–0.04 g of beef tallow, respectively, followed by immersing into the solution for 5 minutes.

Cleaning ability was evaluated by the ration (%) of area on which beef tallow was washed with respect to total area. Results are shown in Table 17.

TABLE 17

|  | Component (b) | Component (a) | CP (%) |
| --- | --- | --- | --- |
| Application Examples 68 | | | |
| No. 1 | B1 | A1 | 34 |
| 2 | B2 | A1 | 39 |
| 3 | B3 | A1 | 43 |
| 4 | B3 | A2 | 53 |
| Comparative Application Example 49 | | | |
| No. 1 | B4 | A1 | 25 |
| 2 | B5 | A1 | 23 |
| 3 | B6 | A1 | 21 |
| 4 | B6 | A2 | 24 |
| 5 | B7 |  | 2 |

In the Table 17, abbreviations are as follows.

B1: Fatty acid esters composition of a polyglycerine obtained in Example 25
B2: Fatty acid esters composition of a polyglycerine obtained in Example 26
B3: Fatty acid esters composition of a polyglycerine obtained in Example 27
B4: Hexaglycerine monolaurate composition prepared in Comparative Example 4 <by the reaction of a fatty acid with a polyglycerine>
B5: Glystar ML-500 manufactured by Sakamoto Yakuhin Kogyo, Ltd.
B6: SY Glystar ML-750 manufactured by Sakamoto Yakuhin Kogyo, Ltd.
B7: Sucrose laurate
A1: Glycerine succinate monolaurate
A2: Glycerine succinate monodecanate In Application Example 69, there was prepared a cleaning agent composition based on the components and the mixing ratio as described below, respectively.

(a) Glycerine succinate monolaurate (12.0 parts by weight)
(b) Fatty acid esters composition of a polyglycerine obtained in Example 25 (5.0 parts by weight)
(c) Sodium tripolyphosphate (35.0 parts by weight)
(d) citric acid (2.5 parts by weight)
(e) Sodium sulphate (45.5 parts by weight)

The cleaning agent composition was dissolved into water to obtain an aqueous solution having 0.33% by weight.

The solution was employed to wash soy beans, resulting in showing high washing power and sterilizing ability.

In Application Example 70, there as prepared a cleaning agent composition based on the components and the mixing ratio as described below, respectively.

(a) Glycerine succinate monomilystate (15.0 parts by weight)
(b) Fatty acid esters composition of a polyglycerine obtained in Example 25 (2.0 parts by weight)
(b) Fatty acid esters composition of a polyglycerine obtained in Example 27 (5.0 parts by weight)
(c) Sodium pyrophosphate (30.0 parts by weight)
(d) Phosphoric acid (2.0 parts by weight)
(e) Sodium sulphate (46.0 parts by weight)

The cleaning agent composition was dissolved into water to obtain an aqueous solution having 0.20% by weight.

The solution was employed to wash tomatoes, resulting in showing high washing ability.

In Application Example 71, there was prepared a cleaning agent composition based on the components and the mixing ratio as described below, respectively.

There was adjusted PH of an aqueous solution containing 0.10% by weight of glycerine succinate monolaurate and 0.030% by weight of the fatty acid esters composition of a polyglycerine obtained in Example 25 to 4, 5, and 7 with an aqueous solution of sodium hydroxide to obtain three aqueous solutions having different PHs. Sterilizing ability was evaluated as follows concerning the three aqueous solutions having different PHs Triangular flasks containing 10 g of soy beans and 90 ml of the respective aqueous solution were vibrated for 5 minutes.

After vibrated for 5 minutes, respective washed soy beans were mixed with 90 ml of sterilized water in a 100-ml flask, followed by placing in a thermostatically-controlled oven at 38° C. for 20 hours.

After placing for 20 hours, soy beans were minutely crushed together with sterilized water in a homogenizer, followed by filtering with a sterilized gauze to separate solid.

A filtered liquid which is a starting liquid was diluted into ten times, hundred times, and thousand times, respectively, with a sterilized physiological aqueous solution of sodium chloride. 1 ml of the starting liquid and 3 diluted liquid were poured into 4 laboratory dishes, respectively.

Subsequently, there was poured 15–20 ml of a standard agar culture medium which was kept at 50° C. after sterilized in a high pressure, followed by immediately mixing, respectively.

The 4 laboratory dishes were settled until the agar culture media completely coagulate. After coagulated, the 4 laboratory dishes were cultivated at 35° C. for 2 days to count the number of colonies by a conventional method. As a result, the number of microorganisms was less than 10 per 1 g of soy beans in all the laboratory dishes. For references, the same procedures were repeated except that water having Ph of 7 was employed in place of the solution containing the fatty acid esters composition of a polyglycerine to obtain the number of microorganisms of 5.5×106 per 1 g of soy beans.

<APPLICATION EXAMPLES 72 TO 77 AND COMPARATIVE APPLICATION EXAMPLES 54 TO 56/

Evaluations as a foaming composition for cleaning>

TABLE 18

|  | Application Examples | | | Comparative Application Example | | |
| --- | --- | --- | --- | --- | --- | --- |
|  | 72 | 73 | 74 | 54 | 55 | 56 |
| A1 | 1.0 | | | | | |
| A2 | | 1.0 | | | | |
| A3 | | | 1.0 | | | |
| A4 | | | | 1.0 | | |
| A5 | | | | | 1.0 | |
| A6 | | | | | | 1.0 |
| Property | | | | | | |
| Stability | G | G | G | P | G | G |
| Stability (Deterioration ratio of protein): It was | E | E | E | I | E | E |
| Foaming ability | G | G | G | I | I | I |
| Durability of Foam (Stability of Foam) | G | G | G | I | I | I |
| Feel in use | G | G | G | I | G | G |

In the Table 18, A1 to A6 correspond to the following composition, respectively.

A1: Fatty acid esters composition of a polyglycerine obtained in Example 25

A2: Fatty acid esters composition of a polyglycerine obtained in Example 26

A3: Fatty acid esters composition of a polyglycerine obtained in Example 27

A4: Hexaglycerine monolaurate composition prepared in Comparative Example 4 <by the reaction of a fatty acid with a polyglycerine>

A5: SY Glystar ML-500 manufactured by Sakamoto Yakuhin Kogyo, Ltd.

A6: SY Glystar ML-750 manufactured by Sakamoto Yakuhin Kogyo, Ltd.

In Application Examples 72–74 and Comparative Application Examples 54–56, there was prepared a cleaning agent composition based on the components and the mixing ratio as described below, respectively.

Fatty acid esters composition of a polyglycerine (1.0% by weight)

Cetyl alcohol (2.0% by weight)

Ethyl alcohol (50% by weight)

Purified water (42.0% by weight)

Liquified Petroleum Gas/L.P.G. (5.0% by weight)

In Application Example 75, there was prepared a cleaning agent composition based on the components and the mixing ratio as described below, respectively.

Fatty acid esters composition of a polyglycerine obtained in Example 25 (2.5% by weight)

Cetstearyl alcohol (2.5% by weight)

Perfumes (0.2% by weight)

Purified water (53.5% by weight)

Ethyl alcohol (35.0% by weight)

Liquified Petroleum Gas/L.P.G. (7.0% weight)

In Application Example 76, there was prepared a cleaning agent composition based on the components and the mixing ratio as described below, respectively.

Fatty acid esters composition of a polyglycerine obtained in Example 25 (1.5% by weight)

Cetyl alcohol (3.0% by weight)

Saffron oil (0.1% by weight)

Perfumes (0.2% by weight)

Purified water (36.2% by weight)

Ethyl alcohol (55.0% by weight)

Liquified Petroleum Gas/L.P.G. (4.0% by weight)

In Application Example 77, there was prepared a cleaning agent composition based on the components and the mixing ratio as described below, respectively.

Fatty acid esters composition of a polyglycerine obtained in Example 25 (1.2% by weight)

Behenyl alcohol (0.5% by weight)

POE(4) stearylether (1.0% by weight)

Orange oil (0.1% by weight)

Perfumes (0.2% by weight)

Purified water (47.1% by weight)

Ethyl alcohol (45.0% by weight)

Liquified Petroleum Gas/L.P.G. (5.0% by weight)

The cleaning agent composition in Application Examples 75–77 exhibited an excellent stability, foaming ability, durability of foam, and cleaning ability.

In the Application Examples and Comparative Application Examples, methods and standard for evaluation were according to the following stages.

(a) Stability (Deterioration ratio of protein): It was evaluated by deterioration ratio (HDR %) of hemoglobin. It exhibited a good relationship with an irritating intensity for eyes according to a Draze method.

HDR %=[(LAOC−LAOD)/(LAOC)]×100

LAOC: Light absorption degree by a control sample

LAOD: Light absorption degree after deteriorating by a test sample

E: HDR of <5%

G: HDR of 5% to <15%

I: HDR of 15% to <50%

B: HDR of not less than 50%

(b) Cleaning ability: It was measured by a cleaning process in which a fixed amount of artificial fatty skin dirt containing an ultraviolet ray absorbent was coated on a rubber plate, and then rubbing was carried out at three cycles with a paper towel containing a sample liquid under a fixed loading. The artificial fatty skin dirt after cleaning was recovered with a solvent, and then the amount of the ultraviolet ray absorbent was measured to evaluate as follows.

G: Cleaning ability of not less than 60%

I: Cleaning ability of 40% to <60%

B: Cleaning ability of not more than 40%

(c) Foaming ability: It was evaluated by a process that there were mixed an agent for foaming (spraying) a mixture and the mixture in a fixed ratio to prepare an aerosol, and the aerosol was filled in a can for spraying, and then the aerosol was sprayed onto hands at −5° C., 25° C., and 30° C., respectively. Foaming ability was evaluated by organoleptic tests.
G: Good
I: Insufficient
(d) Durability of Foam (Stability of Foam): It was evaluated by a process that the aerosol was sprayed, there was measured a ratio (Fr %) between the volume of foam immediately after spraying and the volume after 30 minutes.
Fr %=[(Volume of foam after 30 minutes)/(Volume of foam immediately after spraying)]×100
G: Fr of not less than 80%
I: Fr of 50% to <80%
B: Fr of <50%
(e) Feel in use: It was evaluated by a method that 5g of respective sample was employed for washing hairs, and then wiped with towels. At 30 minutes after wiping, a refreshing feel in hairs was evaluated by organoleptic tests of 8 panelists according to the following 5 stages.
Excellent: 5
Good: 4
Normal: 3
Slightly poor: 2
Poor: 1
Evaluations were shown by average points of the 8 panelists.
(a) Stability: It was evaluated by a method that samples were preserved at temperatures of −5° C., 0° C., 25° C., and 30° C. for 1 month, and the samples were sprayed, conditions of foam at the temperatures and at the 25° C. were visually observed to evaluate by the following stages.
G: Appropriate as a foaming composition for cleaning
P: Inappropriate as a foaming composition for cleaning

EXAMPLE 28/

Preparation of a highly-purified fatty acid esters composition of a polyglycerine from the composition (a decaglycerine monolaurate composition) obtained in Example 5>

The composition obtained in Example 5 and 2% by weight of water was charged into a flask. Subsequently, the flask was heated to 135° C. while stirring under refluxing, followed by maintaining at the temperature for 2 hours. Subsequently, the flask was heated to 140° C. Distillation in reduced pressures was carried out while maintaining at the temperature in order to remove water for 4 hours to obtain a highly-purified fatty acid esters composition of a polyglycerine. Reduced pressure degree was finally 10 mmHg.

There was carried out HPLC analysis with the analytical condition No. 2 relating to the highly-purified fatty acid esters composition of a polyglycerine. FIG. 24 (ML-10) is a chart obtained by the HPLC analysis. It was identified from the chart that the composition contains a monolaurate of polyglycerine of 81.26% by weight, polyglycerine of 8.20% by weight, and other components of 10.54% by weight by the analytical condition No. 2 in the HPLC analysis as defined hereinabove.

<COMPARATIVE EXAMPLES 16 AND 17/

HPLC Analysis by the analytical Condition No. 2 relating to a fatty acid esters composition of a polyglycerine which is commercially supplied>

As fatty acid esters composition which is commercially supplied prepared by the reaction of a polyglycerine with a fatty acid, SY Glystar ML-750 manufactured by Sakamoto Yakuhin, Ltd. and Sunsoft Q-125 manufactured by Taiyo Kagaku, Ltd. were analyzed by the analytical condition No. 2 in HPLC analysis. FIGS. 25 (HL-750) and 26 (Q-12S) are a respective chart obtained by the HPLC analysis.

It was identified from the charts that the respective compositions contain a monolaurate of polyglycerine of 44.92% by weight, polyglycerine of 14.16% by weight, and other components of 40.82% by weight, and a monolaurate of polyglycerine of 48.80% by weight, polyglycerine of 26.88% by weight, and other components of 24.32% by weight by the analytical condition No. 2 in the HPLC analysis as defined hereinabove.

<COMPARATIVE EXAMPLE 18 /

HPLC Analysis by the analytical condition No. 3 relating to a fatty acid esters composition of a polyglycerine which is commercially supplied>

As fatty acid esters composition which is commercially supplied prepared by the reaction of a polyglycerine with a fatty acid, SY Glystar Ml-500 manufactured by Sakamoto Yakuhin, Ltd. was analyzed by the analytical condition Nn. 3 in HPLC analysis.

Figure 27:
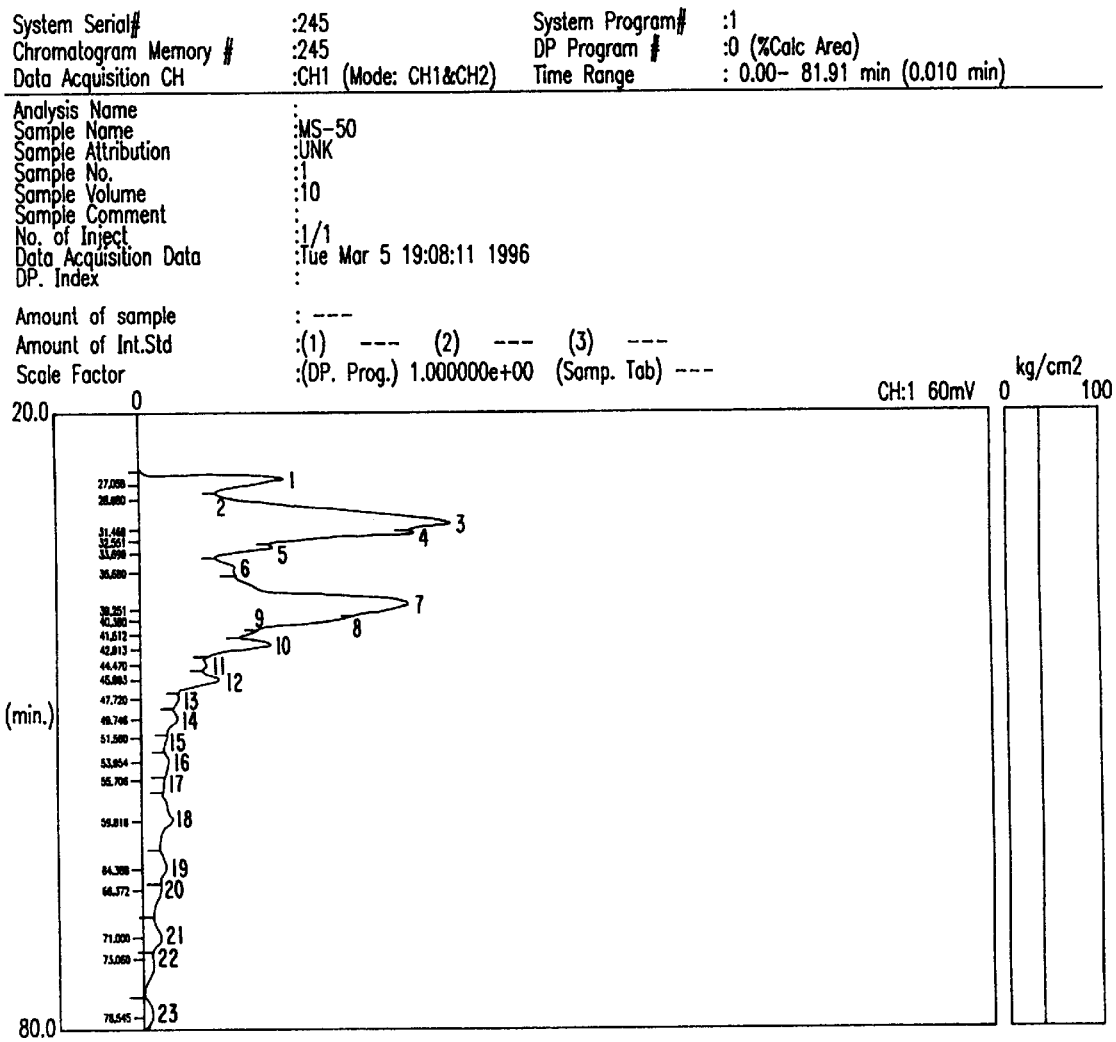
FIG. 27 is a chart obtained by HPLC relating to a commercially supplied fatty acid esters competition of a polyglycerine employed in Comparative Example 18.

FIG. 27 is a chart obtained by the HPLC analysis. It was identified from the charts that the respective compositions contain a monolaurate of polyglycerine of 38.20% by weight, polyglycerine of 6.17% by weight, and other components of 55.64% by weight.

While the invention has been described in detail and with reference to the specific embodiments thereof, it will be apparent to those skilled in the art that various changes and modifications can be made therein without departing from the spirit and scope thereof.

What is claimed is:

1. A water-in-oil type-emulsified composition for cosmetics which comprises the combination of components:
   (i) glycerine,
   (ii) oil, wax, or a combination thereof,
   (iii) water, and
   (iv - a) a fatty acid esters composition of a polyglycerine containing more than 70% of a fatty acid monoester represented by the general formula (1) described below:

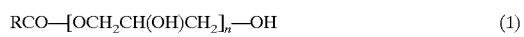

$$RCO-[OCH_2CH(OH)CH_2]_n-OH \quad (1)$$

wherein R is an alkyl group, an alkenyl group, or a hydroxyl group-substituted alkyl group which have a carbon number ranging from 6 to 21, and n is an integer of at least 4, based on a peak area ratio detected using an ultraviolet ray absorption detector in a high performance liquid chromatographic analysis method; or
   (iv - b) a highly-purified fatty acid esters composition of a polyglycerine having an oxirane oxygen concentration of below 100 ppm, said oxirane concentration is defined by the titration method defined in Cd. 9–57 of Journal of American Oil Chemists' Society, or having a ratio of below 0.01%, said ratio is a peak area value of a chemical shift between 2.7 ppm and 2.8 ppm assigned by methylene proton derived from an oxirane group with respect to a peak area value of a chemical shift between 3.4 ppm and 4.4 ppm assigned by methylene proton and methine proton derived from a polyglycerine with a proton NMR.

2. A water-in-oil type=emulsified composition for cosmetics as set forth in claim 1, wherein said component (ii)

comprises a liquid paraffin, vaseline, olive oil, lanolin, squalene, tri(capryl-capric acid)glyceryl, bleached bees wax, or a combination thereof.

3. A transparent liquid composition for cosmetics which comprises the combination of components:
(i) at least one non-ionic surface active agent,
(ii) at least one water-soluble compound having at least two hydroxyl groups,
(iii) at least one oily component,
(iv) water, and
(v - a) a fatty acid esters composition of a polyglycerine containing more than 70% of a fatty acid monoester represented by the general formula (1) described below:

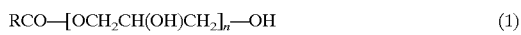

RCO—[OCH₂CH(OH)CH₂]ₙ—OH    (1)

wherein R is an alkyl group, an alkenyl group, or a hydroxyl group-substituted alkyl group which have a carbon number ranging from 6 to 21, and n is an integer of at least 4, based on a peak area ratio detected using an ultraviolet ray absorption detector in a high performance liquid chromatographic analysis method; or
(v - b) a highly-purified fatty acid esters composition of a polyglycerine having an oxirane oxygen concentration of below 100 ppm, said oxirane concentration is defined by the titration method defined in Cd. 9–57 of Journal of American Oil Chemists' Society, or having a ratio of below 0.01%, said ratio is a peak area value of a chemical shift between 2.7 ppm and 2.8 ppm assigned by methylene proton derived from an oxirane group with respect to a peak area value of a chemical shift between 3.4 ppm and 4.4 ppm assigned by methylene proton and methine proton derived from a polyglycerine with a proton NMR.

4. A transparent liquid composition for cosmetics as set forth in claim 3, wherein said oily component (iii) comprises vegetable oil, squalene, a fatty acid ester of sorbitan, a fatty acid ester of diglycerine, tri(2-ethylhexanoic acid) glyceryl, tri(capryl-capric acid)glyceryl, a liquid paraffin, a polysiloxane compound, or a combination thereof.

5. A transparent liquid composition for cosmetics as set forth in claim 3, wherein said water-soluble compound having at least two hydroxyl groups, component (ii), comprises propylene glycol, 1,3-butanediol, dipropylene glycol, glycerine, diglycerine, a polyglycerine, trimethylol propane, erythritol, pentaerythritol, isopreneglycol, sorbitan, glucose, sorbitol, multiotl, saccharose, polyoxy-methylene methylglucoside, diethylene glycol, a polyethyleneglycol, or a combination thereof.

6. A transparent liquid composition for cosmetics as set forth in claim 3, wherein said non-ionic surface active agent, component (i), comprises a fatty acid ester of sorbitan, a fatty acid ester of glycerin, a fatty acid ester of a polyethylene glycol, a polyoxyethylene alkylether, a polyoxyethylene alkylphenylether, a polyopxyethylene sorbitan ester of a fatty acid, a polyoxyethylene sorbitol ester of a fatty acid, or a combination thereof.

7. A gel-like emulsified composition for cosmetics which comprises the combination of components:
(i) glycerine,
(ii) liquid oily component,
(iii) a polyvalent alcohol except glycerine, and
(iv - a) a fatty acid esters composition of a polyglycerine containing more than 70% of a fatty acid monoester represented by the general formula (1) described below:

RCO—[OCH₂CH(OH)CH₂]ₙ—OH    (1)

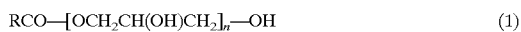

wherein R is an alkyl group, an alkenyl group, or a hydroxyl group-substituted alkyl group which have a carbon number ranging from 6 to 21, and n is an integer of at least 4, based on a peak area ratio detected using an ultraviolet ray absorption detector in a high performance liquid chromatographic analysis method; or
(iv - b) a highly-purified fatty acid esters composition of a polyglycerine having an oxirane oxygen concentration of below 100 ppm, said oxirane concentration is defined by the titration method defined in Cd. 9–57 of Journal of American Oil Chemists' Society, or having a ratio of below 0.01%, said ratio is a peak area value of a chemical shift between 2.7 ppm and 2.8 ppm assigned by methylene proton derived from an oxirane group with respect to a peak area value of a chemical shift between 3.4 ppm and 4.4 ppm assigned by methylene proton and methine proton derived from a polyglycerine with a proton NMR.

8. A gel-like emulsified composition for cosmetics as set forth in claim 7, wherein said liquid oily component (ii) comprises a hydrocarbon oil, a liquid paraffin, squalene, an ester oil, cetyl octanate, isopropyl myristate, a fatty acid triglyceride, tioctanic acid, triglyceride, olive oil, or a combination thereof.

9. A gel-like emulsified composition for cosmetics as set forth in claim 7, wherein said polyvalent alcohol except glycerine, component (iii), comprises propylene glycol, 1,3-butylene glycol, maltitol, sorbitol, or a combination thereof.

10. A foaming composition for cleaning which comprises the combination of components:
(i) at least one of a lower monovalent alcohol having a carbon number ranging from 1 to 3,
(ii) water,
(iii) at least one of a higher alcohol having a carbon number ranging from 12 to 22, and
(iv - a) a fatty acid esters composition of a polyglycerine containing more than 70% of a fatty acid monoester represented by the general formula (1) described below:

RCO—[OCH₂CH(OH)CH₂]ₙ—OH    (1)

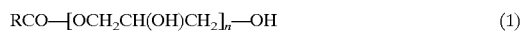

wherein R is an alkyl group, an alkenyl group, or a hydroxyl group-substituted alkyl group which have a carbon number ranging from 6 to 21, an n is an integer of at least 4, based on a peak area ratio detected using an ultraviolet ray absorption detector in a high performance liquid chromatographic analysis method; or
(iv - b) a highly-purified fatty acid esters composition of a polyglycerine having an oxirane oxygen concentration of below 100 ppm, said oxirane concentration is defined by the titration method defined in Cd. 9–47 of Journal of American Oil Chemists' Society, or having a ratio of below 0.01%, said ratio is a peak area value of a chemical shift between 2.7 ppm and 2.8 ppm assigned by methylene proton derived from an oxirane group with respect to a peak area value of a chemical shift between 3.4 ppm and 4.4 ppm assigned by methylene proton and methine proton derived from a polyglycerine with a proton NMR.
(v) a foaming agent.

11. A foaming composition for cleaning as set forth in claim 10, wherein said lower monovalent alcohol having a carbon number ranging from 1 to 3, component (i), com prises ethanol, n-propanol, isopropanol, or a combination thereof.

12. A foaming composition for cleaning as set forth in claim 10, wherein said higher alcohol having a carbon number ranging from 12 to 22, component (iii), comprises lauryl alcohol, myristyl alcohol, palmityl alcohol, stearyl alcohol, oleyl alcohol, cetyl alcohol, behenyl alcohol, or a combination thereof.

* * * * *